United States Patent
Kazakov

(10) Patent No.: US 9,816,130 B2
(45) Date of Patent: Nov. 14, 2017

(54) METHODS OF CONSTRUCTING SMALL RNA LIBRARIES AND THEIR USE FOR EXPRESSION PROFILING OF TARGET RNAS

(71) Applicant: SomaGenics, Inc., Santa Cruz, CA (US)

(72) Inventor: Sergei A. Kazakov, San Jose, CA (US)

(73) Assignee: SOMAGENICS, INC., Santa Cruz, CA (US)

( * ) Notice: Subject to any disclaimer, the term of this patent is extended or adjusted under 35 U.S.C. 154(b) by 422 days.

(21) Appl. No.: 14/367,200

(22) PCT Filed: Dec. 21, 2012

(86) PCT No.: PCT/US2012/071374
§ 371 (c)(1),
(2) Date: Jun. 19, 2014

(87) PCT Pub. No.: WO2013/096839
PCT Pub. Date: Jun. 27, 2013

(65) Prior Publication Data
US 2015/0051099 A1    Feb. 19, 2015

Related U.S. Application Data

(60) Provisional application No. 61/579,340, filed on Dec. 22, 2011.

(51) Int. Cl.
*C12Q 1/68* (2006.01)
*C12N 15/10* (2006.01)

(52) U.S. Cl.
CPC ....... *C12Q 1/6837* (2013.01); *C12N 15/1093* (2013.01); *C12N 15/1096* (2013.01);
(Continued)

(58) Field of Classification Search
None
See application file for complete search history.

(56) References Cited

U.S. PATENT DOCUMENTS 5,516,664 A    5/1996 Hyman
5,714,320 A    2/1998 Kool
(Continued)

FOREIGN PATENT DOCUMENTS

EP    1627925 A1    2/2006
EP    1978104 A1    10/2008
(Continued)

OTHER PUBLICATIONS

Wages et al. (1997) "Affinity Purification of RNA: Sequence-Specific Capture by Nonionic Morpholino Probes" BioTechniques 23(6):1116-1121.*
(Continued)

*Primary Examiner* — Karen S Weiler
(74) *Attorney, Agent, or Firm* — Wilson Sonsini Goodrich & Rosati

(57) ABSTRACT

Methods, compositions, and kits comprising target-specific oligonucleotides (TSOs) are disclosed herein. Methods, compositions, and kits comprising target-specific oligonucleotides (TSOs) can be used to attach adapters and/or linkers to target RNAs. Methods, compositions, and kits comprising target-specific oligonucleotides (TSOs) can be used in reactions, including, but not limited to, ligation reactions, amplification reactions, and sequencing reactions. Additionally, methods, compositions, and kits comprising target-specific oligonucleotides (TSOs) can be used for reducing and/or preventing the formation of secondary structures in target RNAs. These methods, compositions, and kits can also find use in a number of applications, for example, any application that benefits from stabilizing primary RNA structure, such as detecting and quantifying (Continued)

target RNAs in a sample, in the construction of small RNA libraries, in microarray and RT-qPCR applications, etc.

20 Claims, 26 Drawing Sheets

(52) U.S. Cl.
CPC ......... *C12Q 1/6813* (2013.01); *C12Q 1/6846* (2013.01); *C12Q 1/6853* (2013.01); *C12Q 1/6855* (2013.01); *C12Q 2525/207* (2013.01); *C12Q 2539/101* (2013.01)

(56) References Cited

U.S. PATENT DOCUMENTS

| | | | |
|---|---|---|---|
| 5,854,033 A | 12/1998 | Lizardi | |
| 6,077,668 A | 6/2000 | Kool | |
| 2002/0127569 A1* | 9/2002 | Weisburg | C12Q 1/6834 435/6.12 |
| 2004/0171047 A1 | 9/2004 | Dahl et al. | |
| 2005/0277139 A1 | 12/2005 | Bentwich et al. | |
| 2006/0003337 A1 | 1/2006 | Brandis et al. | |
| 2006/0019258 A1 | 1/2006 | Yeakley et al. | |
| 2006/0063181 A1* | 3/2006 | Green | C12Q 1/6855 435/6.16 |
| 2006/0078894 A1 | 4/2006 | Winkler et al. | |
| 2006/0166245 A1 | 7/2006 | Potter et al. | |
| 2006/0188893 A1 | 8/2006 | Kumar et al. | |
| 2007/0292878 A1 | 12/2007 | Raymond | |
| 2008/0160511 A1 | 7/2008 | Dawson et al. | |
| 2008/0241831 A1 | 10/2008 | Fan et al. | |
| 2009/0023151 A1 | 1/2009 | Dawson et al. | |
| 2011/0244523 A1 | 10/2011 | Tuschl et al. | |
| 2012/0164651 A1 | 6/2012 | Kazakov et al. | |

FOREIGN PATENT DOCUMENTS

| | | |
|---|---|---|
| EP | 2419537 B1 | 1/2014 |
| WO | WO 03/002761 A1 | 1/2003 |
| WO | WO 2005/098029 A2 | 10/2005 |
| WO | WO-2006007569 A2 | 1/2006 |
| WO | WO 2006/102309 A2 | 9/2006 |
| WO | WO 2006/108422 A2 | 10/2006 |
| WO | WO 2010/120803 A2 | 10/2010 |
| WO | WO 2013/096839 A1 | 6/2013 |

OTHER PUBLICATIONS

Roeder (1998) "Solid-phase cDNA library construction, a versatile approach" Nucleic Acids Research 26(14):3451-3452.*
Aird et al., Analyzing and minimizing PCR amplification bias in Illumina sequencing libraries, *Genome Biol.*, 2011, 12: R18.
Aravin et al., Identification and characterization of small RNAs involved in RNA silencing, *FEBS Lett.*, 2005, 579: 5830-40.
Basyuk et al., Human let-7 stem-loop precursors harbor features of RNase III cleavage products, *Nucleic Acids Research*, 2003, 31(22):6593-6597.
Bentwich et al., Identification of hundreds of conserved and non-conserved human microRNAs, *Nat. Genet.*, 2005, 37: 766-70.
Burroughs et al., pre-miRNA profiles obtained through application of locked nucleic acids and deep sequencing reveals complex 5'/3' arm variation including concomitant cleavage and polyuridylation pattern, *Nucleic Acids Res.*, 2012, 40:1424-37.
Chammongpol, et al., miRtect-IT: a novel method for small RNA detection, *Biotechniques*, Jan. 2008; 44(1):129-31.
Chen et al., Real-time quantification of microRNAs by stem-loop RT-PCR, *Nucleic Acids Res.*, Nov. 27, 2005;33(20):e179.
Cheng et al., Highly sensitive determination of microRNA using target-primed and branched rolling-circle amplification, *Angew. Chem. Int. Ed.*, 2009, 48:3268-3272.

Demidov et al., Rolling-circle amplification in DNA diagnostics: the power of simplicity, *Expert Rev. Mol. Diagn.*, 2002, 2(6):89-95.
Fang et al., Attomole microarray detection of microRNAs by nanoparticle-amplified SPR imaging measurements of surface polyadenylation reactions, *J. Am. Chem. Soc.*, 2006, 128: 14044-6.
Frieden et al., Tightening the belt on polymerases: evaluating the physical constraints on enzyme substrate size, *Angew. Chem. Int. Ed.*, 1999, 38(24):3654-3657.
Hafner, et al., RNA-ligase-dependent biases in miRNA representation in deep-sequenced small RNA cDNA libraries, *RNA*, 2011, 17: 1697-712.
Harcourt, et al., Amplified microRNA detection by templated chemistry, *Nucleic Acids Res.*, May 2012;40(9):e65. Epub Jan. 25, 2012.
Jayaprakash et al., Identification and remediation of biases in the activity of RNA ligases in small-RNA deep sequencing, *Nucleic Acids Res.*, 2011, 39: e141.
Jiang, et al., Real-time expression profiling of microRNA precursors in human cancer cell lines, *Nucleic Acids Res.*, Sep. 28, 2005;33(17):5394-403.
Jonstrup, et al., A microRNA detection system based on padlock probes and rolling circle amplification, *RNA*, Sep. 2006;12(9):1747-52. Epub Aug. 3, 2006.
Kong et al., PCR hot start using duplex primers, *Biotechnology Letters*, 2004, 26: 277-280.
Kumar, et al., miR-ID: a novel, circularization-based platform for detection of microRNAs, *RNA*, Feb. 2011;17(2):365-80. Epub Dec. 17, 2010.
Kurschat et al., Optimizing splinted ligation of highly structured small RNAs, *RNA*, 2005, 11: 1909-14.
Linsen et al., Limitations and possibilities of small RNA digital gene expression profiling, *Nat. Methods*, 2009, 6: 474-6.
Lizardi et al., Mutation detection and single-molecule counting using isothermal rolling-circle amplification, *Nature Genetics*, 1998, 19:225-232.
Lu, et al. PCR-based expression analysis and identification of microRNAs. *J RNAi Gene Silencing*. Jul. 28, 2005;1(1):44-9.
Maroney, et al., A rapid, quantitative assay for direct detection of microRNAs and other small RNAs using splinted ligation, *RNA*, Jun. 2007;13(6):930-6. Epub Apr. 24, 2007.
Mattie, et al., Optimized high-throughput microRNA expression profiling provides novel biomarker assessment of clinical prostate and breast cancer biopsies, *Mol Cancer*, Jun. 19, 2006;5:24.
McCormick et al., Experimental design, preprocessing, normalization and differential expression analysis of small RNA sequencing experiments, *Silence*, 2011, 2:2.
Munafo et al., Optimization of enzymatic reaction conditions for generating representative pools of cDNA from small RNA, *RNA*, 2010, 16: 2537-52.
Nallur et al., Signal amplification by rolling circle amplification on DNA microarrays, *Nucleic Acid Res.*, 2001, 29 (23): e118, pp. 1-9.
Navarro et al., Reverse transcription polymerase chain reaction protocols for cloning small circular RNAs, *Journal of Virological Methods*, 1998, 73:1-9.
Overhoff et al., Quantitative detection of siRNA and single-stranded oligonucleotides: relationship between uptake and biological activity of siRNA, *Nucleic Acids Res.*, Dec. 2, 2004;32(21):e170.
Raabe et al., The rocks and shallows of deep RNA sequencing: Examples in the Vibrio cholerae RNome, *RNA*, 2011, 17: 1357-66.
Raymond, et al., Simple, quantitative primer-extension PCR assay for direct monitoring of microRNAs and short-interfering RNAs, *RNA*, Nov. 2005;11(11):1737-44.
Saba, et al., Target labelling for the detection and profiling of microRNAs expressed in CNS tissue using microarrays, *BMC Biotechnol.*, Dec. 12, 2006;6:47.
Sharbati-Tehrani, et al., miR-Q: a novel quantitative RT-PCR approach for the expression profiling of small RNA molecules such as miRNAs in a complex sample, *BMC Mol Biol.*, Apr. 10, 2008;9:34.
Silverman et al., Practical and general synthesis of 5'-adenylated RNA (5'-AppRNA), *RNA*, 2004, 10: 731-46.
Sioud, et al., Profiling microRNA expression using sensitive cDNA probes and filter arrays, *Biotechniques*, Oct. 2004;37(4):574-6, 578-80.

(56) References Cited

OTHER PUBLICATIONS

Sun et al., A bias-reducing strategy in profiling small RNAs using Solexa, *RNA*, 2011, 17: 2256-62.

Szymkowiak, et al., Rapid method for the characterization of 3' and 5' UTRs of influenza viruses, *J Virol Methods*, Jan. 2003;107(1):15-20.

Thomas et al., Determination of the ex vivo rates of human immunodeficiency virus type 1 reverse transcription by using novel strand-specific amplification analysis, *J. Virology*, 2007, 81 (9) pp. 4798-4807.

Tian et al., Sequencing bias: comparison of different protocols of microRNA library construction, *BMC Biotechnol*, 2010, 10: 64.

Vigneaultet al., Efficient microRNA capture and bar-coding via enzymatic oligonucleotide adenylation, *Nat. Methods*, 2008, 5: 777-9.

Wang et al., Oligoribonucleotide circularization by 'template-mediated' ligation with T4 RNA ligase: synthesis of circular hammerhead ribozymes, *Nucleic Acids Res*, 1998, 26: 2502-4.

Zhang et al., Amplification of target-specific, ligation-dependent circular probe, *Gene*, 1998, 211:277-285.

EP 10765038.4 Search Report dated Jul. 23, 2012.

EP 10765038.4 Office action dated Mar. 13, 2013.

PCT/US2010/030922 Search Report and Written Opinion dated Jan. 26, 2011.

PCT/US2010/030922 International Preliminary Report on Patentability dated Jan. 25, 2011.

U.S. Appl. No. 13/264,122 Office Action dated May 8, 2014.

U.S. Appl. No. 13/264,122 Office Action dated Oct. 24, 2013.

PCT/US2012/071374 International Search Report dated Apr. 8, 2013.

PCT/US2012/071374 International Preliminary Report on Patentability dated Jun. 24, 2014.

PCT/US2012/071374 Written Opinion dated Apr. 5, 2013.

European Patent No. 2794926 Extended Search Report dated Sep. 29, 2015.

Lu, et al., Construction of Small RNA cDNA libraries for deep sequencing, Methods, Oct. 2007, pp. 110-117, vol. 43, No. 2.

Kawano, Mitsuoki et al., Reduction of non-insert sequence reads by dimer eliminator LNA oligonucleotide for small RNA deep sequencing, Biotechnigues, Informa Healthcase, Oct. 1, 2010, pp. 751-755, vol. 49, No. 4, U.S.

Sridhara, S. et al., RNA-RNA ligation: Methods, Prospects and Applications, GERF Bulletin of Biosciences, Dec. 2011, pp. 32-35,vol. 2, No. 2.

\* cited by examiner

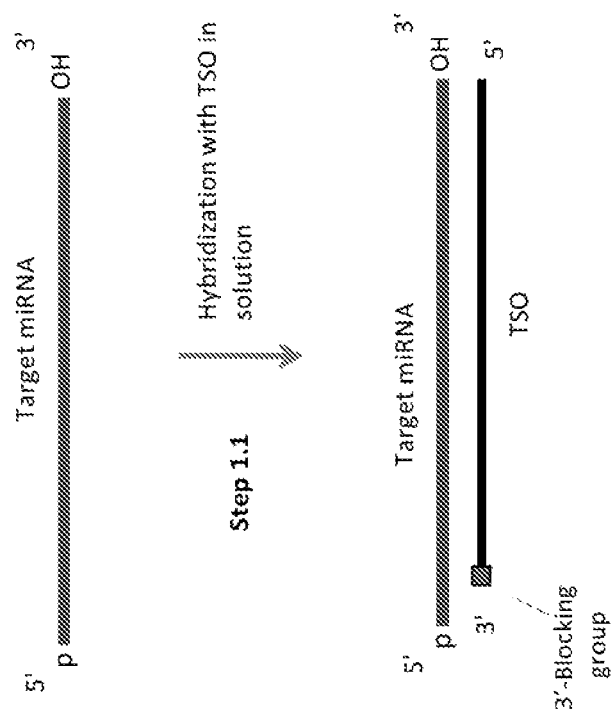

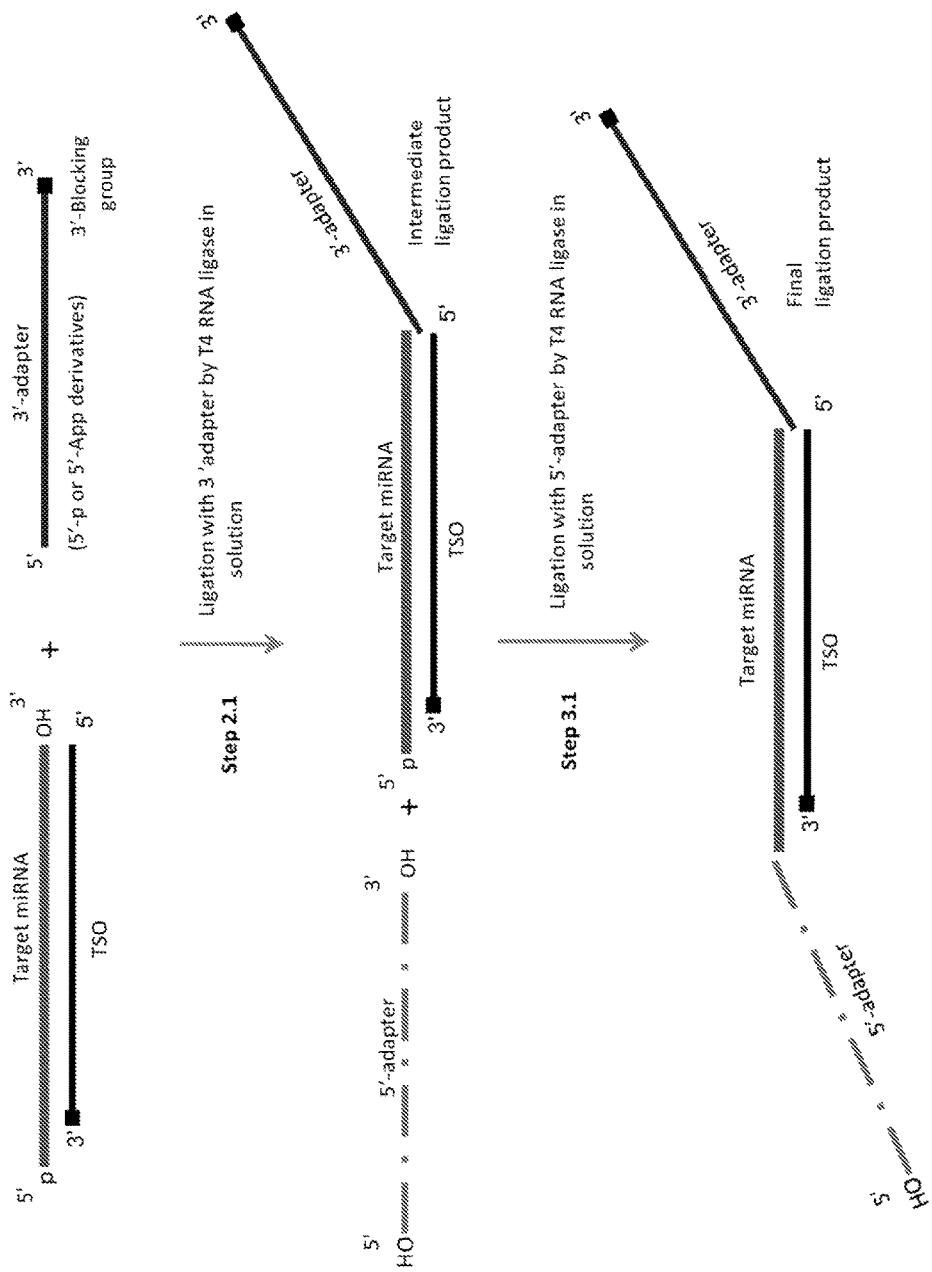

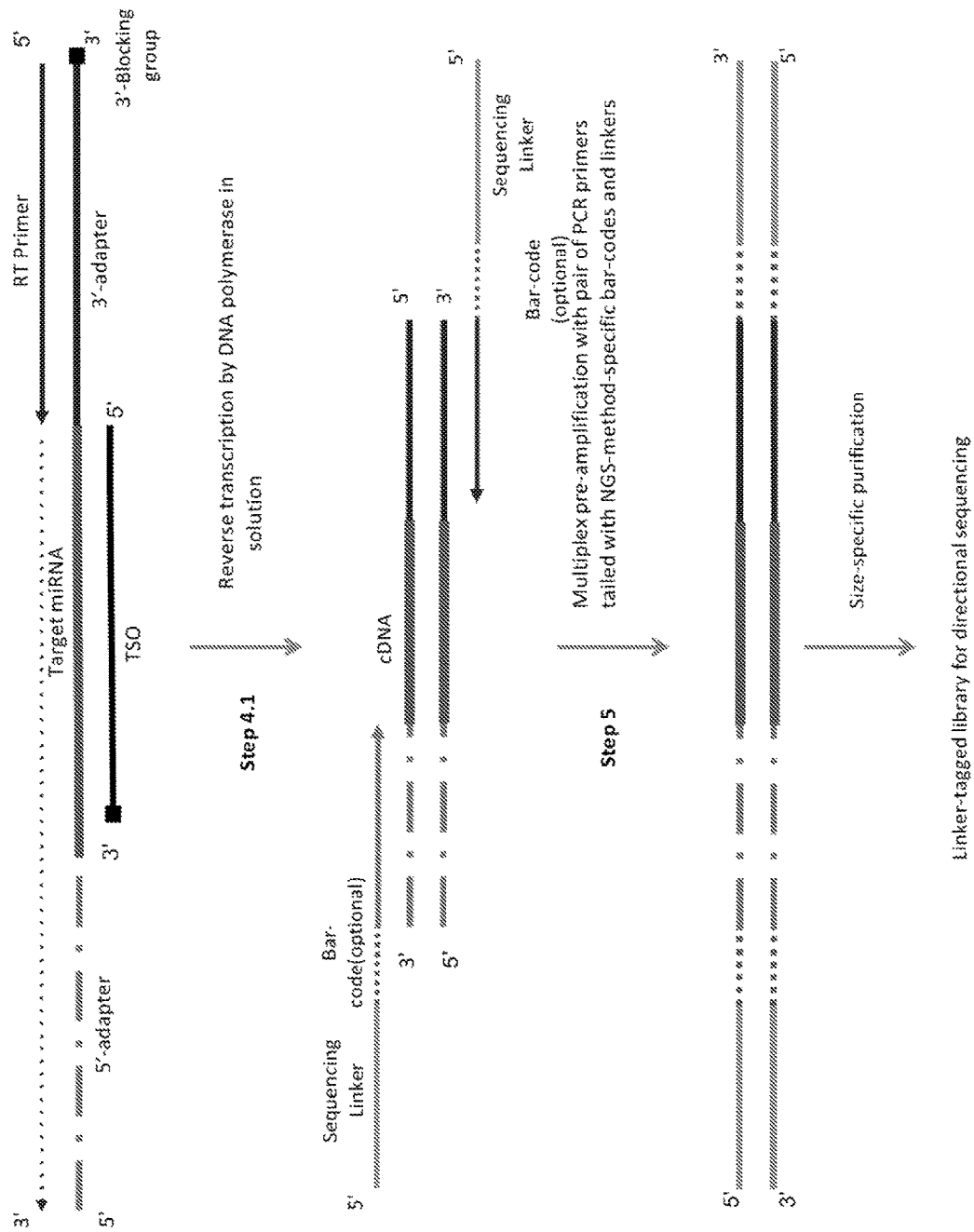

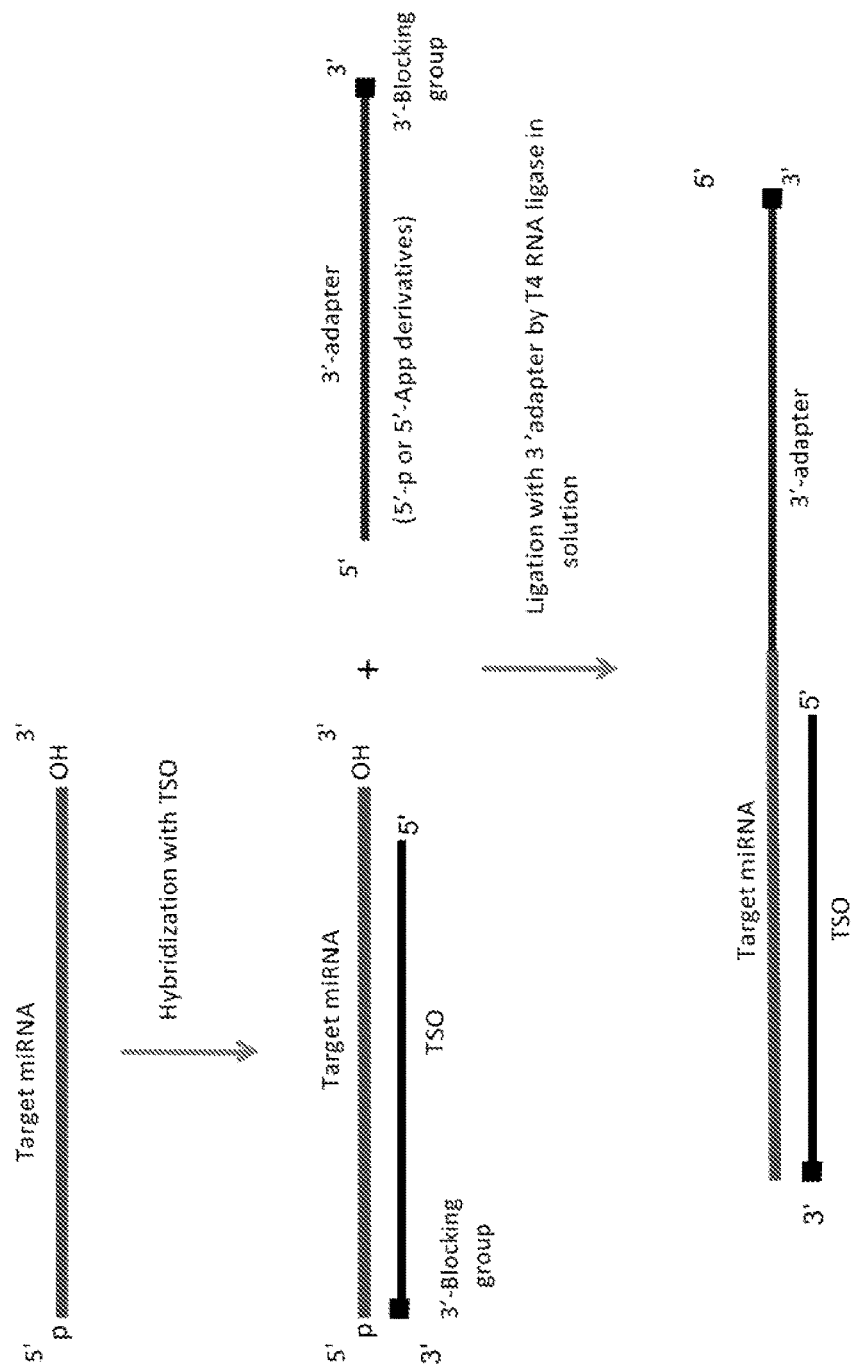

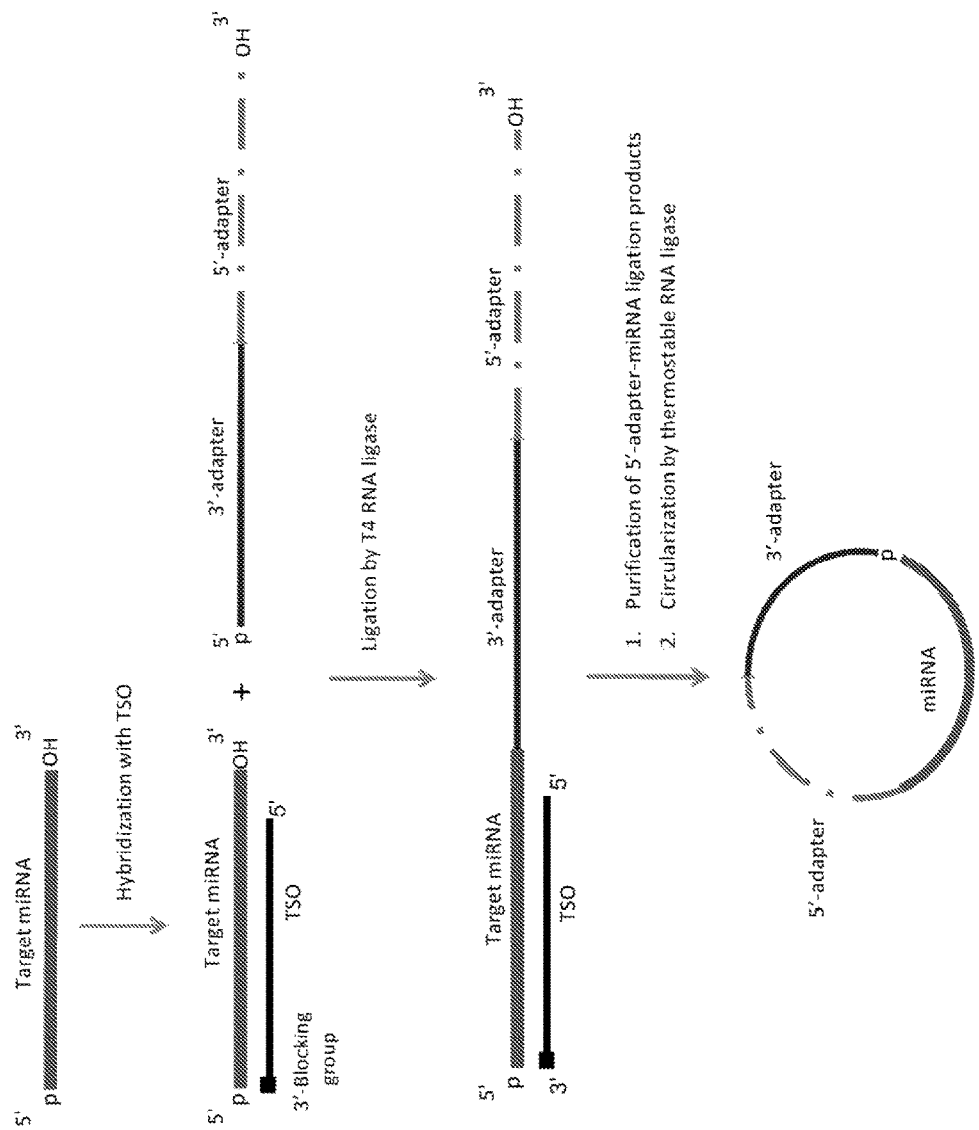

METHODS OF CONSTRUCTING SMALL RNA LIBRARIES AND THEIR USE FOR EXPRESSION PROFILING OF TARGET RNAS

CROSS-REFERENCE

This application is the National Phase entry of International Application No. PCT/US2012/071374, filed Dec. 21, 2012, which claims the benefit of U.S. Provisional Application No. 61/579,340, filed Dec. 22, 2011, both of which application are incorporated herein by references in their entireties.

SEQUENCE LISTING

The instant application contains a Sequence Listing which has been submitted in ASCII format via EFS-Web and is hereby incorporated by reference in its entirety. Said ASCII copy, created on Aug. 19, 2014, is named 40220-707-831-seqlist_ST25.txt and is 14 KB in size.

FIELD OF THE INVENTION

The present invention is in the field of molecular diagnostics. More specifically, it concerns methods and compositions useful for identification, detection, quantification, expression profiling and stabilizing of small RNAs, both naturally occurring and man-made. The present invention finds use in a variety of genomic research and diagnostic applications, in fields including medicine, agriculture, food, and biodefense. The RNA(s) of interest may represent biomarker(s) correlating to specific types of cancer or other diseases such as genetic and metabolic disorders, and viral or bacterial infections.

BACKGROUND OF THE INVENTION

The discovery of microRNAs (miRNAs) and other short RNAs such as small interfering RNAs (siRNA), and short non-coding RNAs (snRNA) has led to a rapid expansion of research elucidating their expression and diverse biological functions.

Recent studies have shown that distinct expression patterns of miRNAs are associated with specific types of cancer and certain other diseases, suggesting that miRNAs could represent a new class of biomarkers and prognostic indicators (Zhang and Farwell 2008). Good biomarkers can facilitate earlier diagnosis, which typically leads to better treatment outcomes.

The ability to distinguish members of small RNA families, such as miRNA isoforms, which differ by single nucleotide polymorphisms, or miRNA isomirs, which differ by nucleotide additions or deletions at the ends, is an important requirement for a successful platform for miRNA-based diagnostics or for monitoring disease progression or response to therapy (Lee et al. 2010).

The majority of current methods for expression profiling (EP) of miRNAs have been adapted from previously established assays for messenger RNAs (mRNAs) with modifications that accommodate the differences between mRNA and miRNA. MiRNAs are much smaller than mRNAs, have 5'-phosphate (5'-p) and 3'-hydroxyl (3'-OH) ends, and are not polyadenylated. Small RNAs that have different ends from miRNAs can be enzymatically converted to 5'-p and 3'-OH ends in order to apply the same methods of analysis as for miRNAs (Lamm et al. 2011; McCormick et al. 2011).

Moreover, long coding and non-coding RNAs may be cleaved into smaller fragments and analyzed similarly to miRNAs, including by RNA sequencing (RNA-seq) methods (Lamm et al. 2011; McCormick et al. 2011). Therefore, the methods described herein for miRNAs are also applicable for other small RNAs as well as for fragments of large RNAs.

Sequencing, which obviously does not require prior knowledge of the RNA sequence, is the only method of RNA analysis that allows discovery of new miRNAs (as well as other naturally occurring RNAs). Sequencing methods can also reveal expression profiles for miRNAs through the frequencies with which individual sequences appear (digital gene expression, DGE) (Linsen et al. 2009). For already known miRNA sequences, expression profiling can also be accomplished by other methods, such as microarrays and RT-PCR, which currently are the standard methods for expression profiling (EP) and molecular diagnostics (Blow 2009; Willenbrock et al. 2009; Benes and Castoldi 2010).

Nevertheless, next generation sequencing (NGS) is increasingly viewed as the future of expression profiling and molecular diagnostics (Su et al. 2011). The NGS methods are good candidates for these jobs, because they combine unlimited multiplexing capability, single-molecule sensitivity, essentially unlimited dynamic range, and unparalleled sequence specificity. NGS provides expression profiles for all miRNAs through the relative frequencies with which individual sequences appear and uses the global mean normalization, which is more accurate than normalization methods using limited numbers of stably expressed small RNA (Mestdagh et al. 2009). Specialized NGS methods have the potential to replace both arrays and RT-qPCR. However, current NGS methods are not suitable for routine miRNA expression profiling and diagnostic assays, primarily because of their high cost and the need for laborious, time-consuming procedures for preparing sequencing libraries. These procedures also include mandatory gel-purification, extraction and ethanol precipitation steps that may significantly affect the accuracy of miRNA quantification (McDonald et al. 2011). Moreover, current NGS methods are not selective for specific miRNA sequences of interest. Therefore, number of sequencing reads for specific miRNA biomarkers can be insignificant due to overwhelming numbers of unrelated sequencing reads.

Knowledge of the absolute and relative expression of miRNAs is important for understanding the biogenesis of miRNAs, regulation of biochemical pathways by miRNAs, and identification of miRNA biomarkers. For a given set of miRNAs, differences in abundance determined for different samples (e.g., differences in miR (miRNA)-16 levels between healthy and diseased tissue) determined by NGS, arrays and RT-qPCR methods are in good correlation. However, the absolute copy numbers of individual miRNAs, as well as the relative copy numbers of various miRNAs detected within the same samples, do not correlate well when determined by the various methods, because each method has its own sequence-associated biases (Nelson et al. 2008; Bissels et al. 2009; Linsen et al. 2009; Git et al. 2010; Lee et al. 2010; Tian et al. 2010). All these methods would significantly benefit from improvements that reduce cost and increase the accuracy of expression profiling of miRNAs of interest.

The present invention addresses these issues.

SUMMARY OF THE INVENTION

Disclosed herein are methods, compositions, and kits comprising one or more target-specific oligonucleotides (TSOs). The methods, compositions, and kits can comprise hybridizing one or more TSOs to one or more target RNAs to form a TSO-hybridized target RNA. The target RNAs comprise small RNA molecules. The methods, compositions, and kits can further comprise attaching one or more adapters to the TSO-hybridized target RNA to form an adapter-ligated target RNA. The methods, compositions, and kits disclosed herein can further comprise quantifying the target RNA by detecting the TSO-hybridized target RNA and/or adapter-ligated target RNA. In some instances, the methods, compositions, and kits further comprise reverse transcribing at least a portion of the target RNA portion of the TSO-hybridized target RNA and/or adapter-ligated target RNA to produce a complementary DNA (cDNA) target RNA. Alternatively, or additionally, the methods, compositions, and kits disclosed herein further comprise amplifying the TSO-hybridized target RNA, adapter-ligated target RNA, or a derivative thereof (e.g., cDNA target RNA) to produce an amplified target RNA. The methods, compositions, and kits disclosed herein can further comprise isolating a TSO-hybridized target RNA, adapter-ligated target RNA, and/or a derivative thereof (e.g., cDNA target RNA, amplified target RNA) to produce an isolated target RNA. In other instances, the methods, compositions, and kits further comprise sequencing the TSO-hybridized target RNA, adapter-ligated target RNA, and/or derivatives thereof (e.g., amplified target RNA, cDNA target RNA, isolated target RNA).

The methods, compositions, and kits disclosed herein can be used to attach an adapter (or linker) to a target RNA via ligation to one or both ends of target RNAs. Alternatively, or additionally, the methods, compositions, and kits disclosed herein can be used for extension of one or both ends of the target RNA. In some instances, the methods, compositions, and kits disclosed are used to reduce ligation bias. Alternatively, or additionally, the methods, compositions, and kits disclosed herein are used to reduce amplification bias. The methods, compositions, and kits disclosed herein can be used to reduce sequencing bias. The methods, compositions, and kits disclosed herein can be used to quantify a target RNA. In some instances, the methods, compositions, and kits disclosed herein can reduce or prevent the formation of secondary structures in the target RNA. In other instances, the methods, compositions, and kits disclosed herein can be used to construct a target RNA library.

Methods, compositions, and kits are provided for preventing the formation of secondary structures in target RNAs and/or in target RNA with attached adapter (or attached linker). Alternatively, or additionally, the methods, compositions, and kits disclosed herein are provided for preventing intramolecular ligation (circularization) in the presence of RNA ligases. Circularization of target RNAs can prevent the attachment of adapters (or linkers) to the target RNAs through intermolecular ligation. These methods and compositions find use in a number of applications; for example, an application that benefits from destabilizing secondary RNA structure, such as detecting and quantifying target RNAs in a sample, in the construction of small RNA libraries, in microarray and RT-qPCR applications, etc.

For example, methods, compositions, and kits provided herein find use in the construction of libraries of target RNAs for RNA sequencing. By "target RNAs" it is meant small non-coding RNAs (ncRNAs), e.g., microRNA (miRNA), small interfering RNA (siRNA), small hairpin RNA (shRNA), piwi-interacting RNA (piRNA), small nuclear RNA (snRNA), small nucleolar RNA (snoRNA), precursor miRNA (pre-miRNA), and short bacterial ncR-NAs as well as fragments of larger coding (such as mRNA and genomic viral RNAs) and non-coding RNAs such as ribosomal RNA, tRNA, non-protein-coding RNA (npcRNA), non-messenger RNA, functional RNA (fRNA), long non-coding RNA (lncRNA, and primary miRNAs (pri-miRNAs). These methods, compositions, and kits can reduce major sources of bias in reactions such as adapter ligation. In some instances, the source of bias is the presence of a secondary structure or a greater tendency toward circularization on the part of some target small RNAs. Such ligation and circularization bias can greatly distort expression profiles of small RNA copy numbers as determined by sequencing. The methods, compositions, and kits disclosed herein can also reduce sequence-dependent bias in adapter ligation. These features can provide increased accuracy in determining absolute copy numbers of target RNAs.

In addition, the methods, compositions, and kits disclosed herein enable expression profiling of selected RNAs of interest rather than all RNAs present in a sample, which can reduce cost and improve throughput of sequencing-based diagnostic assays. Some aspects of the invention are also applicable to probe arrays and RT-qPCR applications that share similar enzymatic steps with library construction protocols, such as adapter ligation to and/or extension of small RNAs.

In addition to reducing bias related to secondary structures of target RNAs and their ligation or extension products, the present invention enables expression profiling of target RNAs. The latter feature is especially important for sequencing applications, since it reduces the number of irrelevant sequencing reads while keeping the same number of total reads. This allows analysis of more libraries or samples simultaneously and facilitates the detection of low-copy miRNAs.

In some aspects of the invention, methods are provided for detecting and quantifying one or more target RNAs in a sample. In some instances, the methods, compositions, and kits disclosed herein comprise hybridizing the one or more target RNA with target-specific oligonucleotides (TSO) to form TSO-hybridized target RNA; and quantitatively detecting the amount of TSO-hybridized target RNA, wherein the amount of TSO-hybridized target RNA detected correlates with the amount of target RNA in the sample. In other instances, the methods, compositions, and kits comprise hybridizing the one or more target RNA with target-specific oligonucleotides (TSO) to form a TSO-hybridized target RNA; ligation of one or more adapters to the ends of the TSO-hybridized target RNA to produce an adapter-ligated target RNA and/or extension of the ends of the TSO-hybridized target RNA to produce a cDNA copy thereof; release of the TSO-hybridized target RNA, the adapter-ligated target, or a cDNA copy thereof into a solution to produced a released target RNA-specific sequence; and quantitatively detecting the amount of the released target RNA-specific sequence, wherein the amount of the target RNA-specific sequence detected correlates with the amount of target RNA in the sample.

In some embodiments, hybridization of a target RNA with a target-specific oligonucleotide (TSO) results in the formation of stable duplexes between the TSO and the target RNA. In some embodiments, hybridization promotes ligation of oligonucleotide adapters to the ends of each of the target RNAs. In some embodiments, hybridization promotes efficient extension of the 3' ends of each of the target RNAs. In some embodiments, the hybridization of the target RNA with the TSO in the sample that also contain non-target RNAs comprises incubating in the presence of T4 RNA ligase 1 (Rnl1). In some instances, hybridization of the target RNA with the TSO in the presence of a Rnl1 comprises circularizing the non-target RNAs. In some instances, at least 50% of the total non-target RNAs in the sample are circularized. In some embodiments, the methods further comprise the step of purifying the TSO-hybridized target RNA and/or the products of ligation of adapter (or adapters) to the TSO-hybridized target RNA by washing under conditions that do not cause dissociation of the TSO-RNA duplexes. The washing procedure permits removal of non-target RNA, non-ligated adapters and other unrelated species.

In some embodiments, quantitatively detecting the amount of TSO-hybridized target RNA comprises enzymatically extending the 3' ends of the target RNA by a nucleotidyl transferase to produce an extended target RNA. In some instances, the extended target RNA comprises additional oligonucleotide tails at the 3' end of the target RNA. Quantitatively detecting can comprise detecting the amount of extended target RNA, wherein the amount of extended target RNA detected correlates with the amount of target RNA in the sample. In some embodiments, the extension of the target RNAs is performed by an RNA-specific nucleotidyl transferase selected from poly(A) polymerase and poly(U) polymerase.

In other embodiments, quantitatively detecting the amount of TSO-hybridized target RNA comprises ligating oligonucleotide adapters to the 5'- and/or 3'-end of the TSO-hybridized target RNA to form adapter-ligated target RNA; and quantitatively detecting the adapter-ligated target RNA, wherein the amount of purified PCR detected correlates with the amount of target RNA in the sample. In some embodiments, the adapter is about 1 100 nucleotides. In some embodiments, the adapter comprises RNA, DNA, or a mix of RNA and DNA, or their chemically modified derivatives or chemical analogs. In some embodiments, the adapter comprises nucleotide sequences that are not homologues (neither complementary nor corresponding) to any nucleotide sequences that are present in or added to the sample. In some embodiments, the adapter comprises a primer sequence for reverse transcription. In some embodiments, the adapter comprises a sequence that is compatible with direct single molecule ("third-generation") RNA sequencing. In some embodiments, the adapter comprises a sequence that is the antisense promoter strand for an RNA polymerase, which can use RNA strand as template, such as bacteriophage T7 and T3 RNA polymerases or their mutants. In some embodiments, the adapter comprises one or more haptens such as biotin or digoxigenin. In some embodiments, the adapter comprises one or more signal moieties. In some embodiments, the adapter comprises one or more tag or probe sequences. In some instances, the one or more tag or probe sequences are useful for one or more reactions. In some instances, the one or more reactions comprise sandwich hybridization with branched DNA probes (bDNA).

In some embodiments, oligonucleotide adapters are ligated to the 5' end of the TSO-hybridized target RNA to form 5'-end adapter-ligated target RNA. In some such embodiments, the 5'-adapters comprise a 3'-end group that is a 3'-hydroxyl (3'-OH). In certain such embodiments, 5'-adapters comprise a 5'-end group that is a 5'-hydroxyl (5'-OH) or 5'-phosphate (5'-p). In certain such embodiments, 5'-adapters having the 5'-OH are ligated first to the target RNAs and then are 5'-phosphorylated by polynucleotide kinase. In some embodiments, oligonucleotide adapters are ligated to the 3' end of the TSO-hybridized target RNA to form 3'-end adapter-ligated target RNA. In some such embodiments, the 3'-adapters comprise a 5'-end group that is a 5'-phosphate (5'-p) or a 5',5'-adenyl pyrophosphoryl cap (5'-App). The latter are also called pre-adenylated adapters (Vigneault et al. 2008; Hafner et al. 2011). In certain such embodiments, the 3'-adapter comprises a chemically blocked 3'-end, e.g., a 3' end comprising a termination group, e.g., a 3'-phosphate (3'-p or Np); a 3'-amino; a 2',3'-dideoxy nucleoside (ddN); a 3'-inverted (3'-3') deoxynucleoside (idN); a 3'-inverted abasic site; or a 3'-non-nucleoside linker (n-linker). Blocking of the 3' end prevents intramolecular self-ligation (circularization) and intermolecular self-ligation (concatamerization) of the 3'-adapters. In certain embodiments, the 3'-adapters represent signal or signal-generating moieties selected from: a [5'-$^{32}$P]-labeled 5'-pNp-3' (pNp); a 5'-pN-3'-n-linker-detectable moiety; a 5'-AppN-3'-n-linker-detectable moiety; and a 5'-pNpN-n-linker-detectable moiety. In some embodiments, oligonucleotide adapters are ligated to both the 5'- and 3'-ends of the TSO-hybridized target RNA to form 5'- and 3'-end adapter-ligated target RNA. In some such embodiments, the 3'-adapter is ligated first and the 5'-adapter is ligated second. In other embodiments, 5'-adapter is ligated first and the 3'-adapter is ligated second. In other embodiments, 5'-adapter and the 3'-adapter are ligated simultaneously. In some embodiments, a single "adapter dimer" comprising the combined sequences of 3'- and 5-adapters, which are compatible with current next generation sequencing (NGS) methods, is ligated to the 5'-p or 3'-OH end of the target RNA.

In some embodiments, the adapter is attached via a template- or splint-independent ligation reaction using an RNA ligase selected from the group consisting of T4 RNA ligase 1 (Rnl1); T4 RNA ligase 2 (Rnl2); and a T4 RNA ligase 2 (Rnl2) derivative; e.g., T4 RNA ligase 2 (1-249) truncated form or RNA ligase 2 (1-249) truncated with the point mutation K227Q. In some instances, the Rnl1 is used for ligation of both 3'- and 5'-adapters, wherein the 3'-adapter is used in 5'-adenylated (5'-App) form in the absence of ATP while the 5'-adapter is ligated in the presence of ATP. In some instances, Rnl2 or an Rnl2 derivative is used in ligation of the 3'-adapter, which is used in 5'-adenylated (5'-App) form in the absence of ATP, while Rnl1 is used in ligation of the 3'-adapter in the presence of ATP. In some instances, only one ligase agent is used. In some instances, multiple ligases are used; e.g., Rnl1 together with Rnl2 or an Rnl2 derivative. In some instances, e.g. when SOLiD 3'-adapter and 5'-adapter are ligated, a T4 DNA ligase or RNA ligase 2 is used for template-dependent ligation.

In some embodiments, the 3'-adapter and/or 5'-adapter (or linkers) comprise sequences used for cloning and sequencing. In some such embodiments, the linker sequences of the 3'-adapter and/or 5'-adapter comprise sequences for cloning and sequences that are compatible with conventional Sanger sequencing methods; or next-generation (second-generation) sequencing technologies such as Illumina's Solexa, Roche's 454, Life Technologies' SOLiD or Ion Torrent; or single-molecule (third-generation) direct RNA sequencing technologies; e.g., from Helicos. In some embodiments, the adapter-ligated target RNA is purified prior to quantitatively detecting the adapter-ligated target RNA; e.g., by gel or capillary electrophoresis, or by washing under conditions that do not cause dissociation of the duplexes; e.g., when ligation reactions are performed in solid state/phase conditions; e.g., when the TSO or TSO-hybridized target RNA is immobilized.

In some embodiments, adapter-ligated target RNA is circularized before PCR amplification. In some embodiments, quantitatively detecting the adapter-ligated target RNA comprises isothermal amplification by linear or hyperbranched rolling circle amplification (RCA).

In some embodiments, the 3'-adapter comprises a sequence of the antisense strand of a promoter and a transcription enhancer for RNA polymerase, and quantitatively detecting the adapter ligated target RNA comprises amplifying the adapter-ligated target RNA by transcription and converting to multiple copies of complementary RNA transcripts (cRNA); and detecting the cRNA, wherein the amount of cRNA detected correlates with the amount of target RNA in the sample.

In some embodiments, quantitatively detecting the adapter-ligated target RNA comprises reverse transcribing (RT) the adapter-ligated target RNA to form an RT product; PCR-amplifying the RT product to form a PCR product; and quantitatively detecting the PCR products, wherein the amount of PCR product detected correlates with the amount of target RNA in the sample. In some embodiments, reverse transcribing comprises extension of an oligonucleotide primer that is fully or partially complementary to the adapter or an extended sequence. In some embodiments, the reverse transcribing comprises the use of a DNA polymerase that has RNA-dependent DNA polymerase activity (e.g., reverse transcriptase) and can use both RNA and DNA templates if any of the adapters contain DNA nucleotides. In some embodiments, the reverse transcribing comprises the use of a DNA polymerase that is a DNA-dependent DNA polymerase accepting both DNA and RNA templates. In some embodiments, the reverse transcribing comprises the use of a DNA polymerase that comprises strand-displacement (helicase) activity, which displaces the TSO hybridized to the target RNA nucleotides. In some embodiments, the reverse transcribing comprises the use of a DNA polymerase that has a high thermostability, which allows the reverse transcribing to be performed at temperatures that are higher than the melting temperature ($T_m$), of the duplexes between the target RNAs and the TSOs. In some embodiments, the DNA polymerase is M-MuLV, SuperScript II, SuperScript III reverse transcriptases, rTth, Hot Multi-Taq thermostable DNA polymerases, or the Klenow Fragment of DNA polymerase I. In some embodiments, the method comprises dissociating the TSO from the adapter-ligated target RNA prior to reverse transcribing. In other embodiments, the method does not comprise dissociating the TSO from the adapter-ligated target RNA prior to reverse transcribing. In some embodiments, the method further comprises degrading the target RNA after reverse transcribing by one or more degradation steps selected from: promoting the internal RNase H activity of a reverse transcriptase during reverse transcribing; additional RNase H treatment; heating at alkaline pH; and heating in the presence of metal ions that can degrade RNA such as $Mn^{2+}$, $Zn^{2+}$, or $Pb^{2+}$.

In some embodiments, the PCR is performed with primers having bar-codes that are usually ≥6 nt long (also known as indexed primers) (Hainer et al. 2011). In some embodiments, the PCR is asymmetric PCR; that is, it is performed using an excess of forward or reverse PCR primers to produce single-stranded amplicons. In some embodiments, the method further comprises purifying the PCR product. In some embodiments, the purifying of PCR product/amplicon comprises size-dependent separation of the PCR product by gel- or capillary electrophoresis; or solid-phase capture of the single-stranded PCR product on immobilized TSO. In some embodiments, the quantitative detection is performed by next-generation (second generation) sequencing. In some embodiments, PCR products are circularized before quantitatively detecting the purified PCR products. In some embodiments, quantitatively detecting the PCR products comprises isothermal amplification by linear or hyperbranched RCA.

In some embodiments, quantitatively detecting the PCR products comprises real-time qPCR with pairs of universal primers that are complementary to the sequences of the 3'- and 5'-adapters; e.g., using TaqMan or similar probes, which are specific to the target RNA sequences and induce signals upon degradation by DNA polymerase with 5'-exonuclease activity. In some such embodiments, real-time PCR is performed using either a single dye such as SYBR Green or EvaGreen dyes.

In some embodiments, the TSO is not immobilized in any step of the methods disclosed herein. In other words, the steps of the methods; e.g., hybridization, extension, adapter ligation, adapter modification, reverse transcription—are performed in solution.

In other embodiments, the TSO is immobilized on a solid phase/support during one or more of the steps in the method. Any of the method steps described above may occur as solid phase reactions, i.e. they may occur while the TSO is immobilized on the solid support. For example, the TSO may be immobilized on the solid support before hybridization with the target RNAs. The TSO may be immobilized on the solid support after hybridization to the target RNAs. In some embodiments, e.g., in some instances when the 3' ends of the target RNA are enzymatically extended, the TSO may be immobilized on the solid after extension. In some embodiments, e.g., in some instances when oligonucleotide adapters are ligated to the 5'- and/or 3'-end of the TSO-hybridized target RNA, the TSO may be immobilized on the solid support after adapter ligation. In some embodiments, e.g., when reverse transcribing is performed, the TSO may be immobilized on the solid support during reverse transcribing. Likewise, any of the method steps described above may occur when the TSO is not immobilized, i.e. the step may occur in solution. For example, the TSO may not be immobilized on the solid support during hybridization. In some embodiments, e.g., in some instances when oligonucleotide adapters are ligated to the 5'- and/or 3'-end of the TSO-hybridized target RNA, the TSO may not be immobilized during adapter ligation. In some embodiments, e.g., when reverse transcribing is performed, the TSO may not be immobilized during reverse transcribing, i.e. the reverse transcribing step is performed in solution. Immobilization may be used in the purification of products prepared while performing any of the above described steps of any of the methods described above or herein. For example, immobilized TSO may be used for purification of TSO-hybridized target RNA, for purification of extension products, for purification of products of adapter ligation, for purification of PCR products, etc.

In some embodiments, the solid phase/support on which the TSO is immobilized is selected from the group consisting of beads; membranes; filters; slides; microtiter plates; and microcapillaries. In some embodiments, the immobilization is by a non-covalent interaction. In some such embodiments, the TSO comprises a hapten group attached to either 5'- or 3'-ends ends of the TSO via non-nucleotide and/or oligonucleotide linkers; or a 5'- or 3'-end oligonucleotide linker complementary to capture oligonucleotides immobilized on the solid support. In certain embodiments, the hapten group is selected from biotin and digoxigenin. In embodiments in which the hapten is biotin, the solid support is coated with streptavidin or with antibodies specific for biotin. In embodiments in which the hapten is digoxigenin, the solid support is coated with antibodies specific for digoxigenin. In other embodiments, the immobilization is by a covalent interaction. In some such embodiments, the covalent interaction is mediated by an oligonucleotide and/or non-nucleotide linker.

In some embodiments, the target RNA is a non-coding RNA or a small fragment of a coding RNA. In some such embodiments, the non-coding RNA is a microRNA. In some embodiments, the target RNA is about 15-to-150 nucleotides in length, e.g., from about 20-to-90 nucleotides in length. In some embodiments, the target RNA comprises a 5' end that comprises a 5'-phospate (5'-p); a 5'-hydroxyl (5'-OH); a 5'-cap; or a 5'-triphosphate (5'-ppp). In instances in which the 5' end comprises a 5'-hydroxyl (5'-OH), 5'-cap, or 5'-triphosphate (5'-ppp), the method further comprises converting the 5' end to a 5'-phospate prior to adapter ligation and/or extension, e.g., by enzymatic conversion. In some embodiments, the target RNA comprises a 3' end that comprises a 3'-hydroxyl (3'-OH); a 3'-phospate (3'-p); or a 2',3'-cyclic phosphate (2',3'>p). In instances in which the 3' end comprises a 3'-phospate (3'-p) or a 2',3'-cyclic phosphate (2',3'>p), the method further comprises the step of converting the 3' end to a 3'-OH prior to adapter ligation and/or extension. In some embodiments, the target RNA comprises a 2' group at the 3' end selected from a 2'-OH or a 2'-oxymethyl (2'-OMe)

In some embodiments, detecting comprises simultaneously detecting and distinguishing variants of the target RNA; e.g., isoforms and isomirs in the case of miRNAs. In some embodiments, the sample is a tissue extract, a cell extract, or an extracellular fluid. In certain embodiments, the sample is a tissue or cell lysate, extracellular fluid, a crude nucleic acid extract, a total RNA extract, or a purified fraction of small RNAs of which length is selected by a method of the purification. In some embodiments, products of the various enzymatic reactions described above, e.g., adapter ligation, extension by nucleotidyl transferase, reverse transcription, rolling circle amplification, or transcription; are labeled during or after the enzymatic reactions with signal (or signal generating/amplifying) moieties and then are detected on arrays.

In some aspects of the invention, one or more TSOs are provided. In some embodiments, the TSOs unfold target RNA intramolecular (secondary) structures that inhibit adapter ligation to (or extension of) target RNA ends. In some embodiments, the TSOs suppress circularization of target RNAs under ligation conditions, while allowing non-target target RNAs to be circularized, preventing adapter ligation to or extension of their ends and thus excluding the non-target target RNAs from subsequent amplification and detection. In some embodiments, the TSOs stabilize the target RNA ends in conformations that allow them to be substrates for template- or splint-independent ligation or extension. In the latter case, the optimal structure of the target RNA-TSO complex depends on the enzymes, enzymatic reaction conditions, and adapters used. In some embodiments, the TSO provides capture of target RNAs on a solid support through either non-covalent or covalent immobilization of the TSO. In some embodiments, the TSO does not produce a single-stranded overhang at the 5' end of TSO when hybridized to the target RNA, and as such cannot serve as template for target RNA 3'-end extension, and cannot serve as a splint in ligation of target RNAs to adapters. In some embodiments, the TSO possess one or more blocking groups at their 3' ends and as such cannot serve as a primer. In some embodiments, the TSO possess one or more blocking groups at both their 3' ends and 5' ends, and as such, cannot be ligated or extended. In some embodiments, the TSO does not have complementarity to any RT (reverse transcription) or PCR primers used, or contains one or more residues that cannot be replicated by DNA polymerase selected from: abasic site(s), nucleoside(s) with 2'-OMe or 2'-F modifications, or by comprising an internal, stable hairpin; and as such cannot serve as a template for amplification.

In some aspects of the invention, the TSO is shorter than target RNA by at least 1 nt. In some embodiments, the TSO is complementary over 70% or more of its sequence with the target RNA. In some embodiments, the TSO is complementary over 80% or more of its sequence with the target RNA. In some embodiments, the TSO binds to different isoforms (forming mismatched/imperfect duplexes) and isomirs of the target RNA. In some embodiments, the TSO sequences are neither complementary to nor correspond to adapters/linkers and/or RT-PCR primers used for adapter ligation and amplification reactions to detect the target RNAs. In some embodiments, the TSO forms intermolecular complexes/duplexes with the target RNA, which have higher stability than intramolecular (secondary) structure of the target RNA under standard ligation and/or extension reaction conditions. In some embodiments, the TSO comprises RNA; DNA; a mix of DNA and RNA residues or their modified analogs such as 2'-OMe, or 2'-fluoro (2'-F), locked nucleic acid (LNA), or abasic sites. In some embodiments, the TSO comprises a blocking group at the 3'-end that prevents the ligation to or extension of the 3' end, e.g., 3'-p, or 3'-amino, or 2',3'-dideoxy nucleoside (ddN), or 3'-inverted 3'-3' deoxy nucleoside (idN). In some embodiments, the TSO comprises a blocking group at 5' end that prevent its phosphorylation, e.g., a 5'-OMe, or non-nucleotide linker. In some embodiments, the TSO comprises one or more residues that cannot be replicated by DNA polymerase, e.g., abasic site(s) or nucleoside(s) with 2'-OMe or 2'-F modifications. In some embodiments, the TSO comprises one or more internal, stable hairpins that cannot be bypassed and replicated by DNA polymerase. In some embodiments, the TSOs provide single-stranded overhangs at target RNA ends ranging from 1-6 nucleotides (nt) at the 5' end and 0-11 nucleotides at the 3' end upon binding with the target small RNA. In some embodiments, the overhang is selected from: 0-3 nt at 3' end; 3-4 nt at 5' end; 4 nt at 5' end and 0 nt at 3' end; 6 nt at both 5' and 3' ends; and 0 nt at 5' end and 1-3 nt at 3' end.

In some aspects of the invention, methods are provided for constructing libraries of target RNAs. In some embodiments, the method comprises hybridizing target RNAs in a sample with target-specific oligonucleotides (TSO) to form TSO-hybridized target RNA, ligating oligonucleotide adapters to the 5'- and/or 3'-end of the TSO-hybridized target RNA to form adapter-ligated target RNA, reverse transcribing (RT) the adapter-ligated target RNA to form an RT product; and PCR-amplifying the RT product to form a PCR product, wherein the PCR product comprises a library of target RNAs.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 5. Scheme of construction of a Solexa- or 454-like "miRNA library" comprising hybridization of target miRNAs with a TSO (A); sequential ligation of adapters to both ends of miRNAs (B); and reverse transcription (C) all in solution. This scheme can be applied to the construction of small RNA libraries for Sanger, Solexa and 454 sequencing platforms.

DETAILED DESCRIPTION OF THE INVENTION

Figure 1:
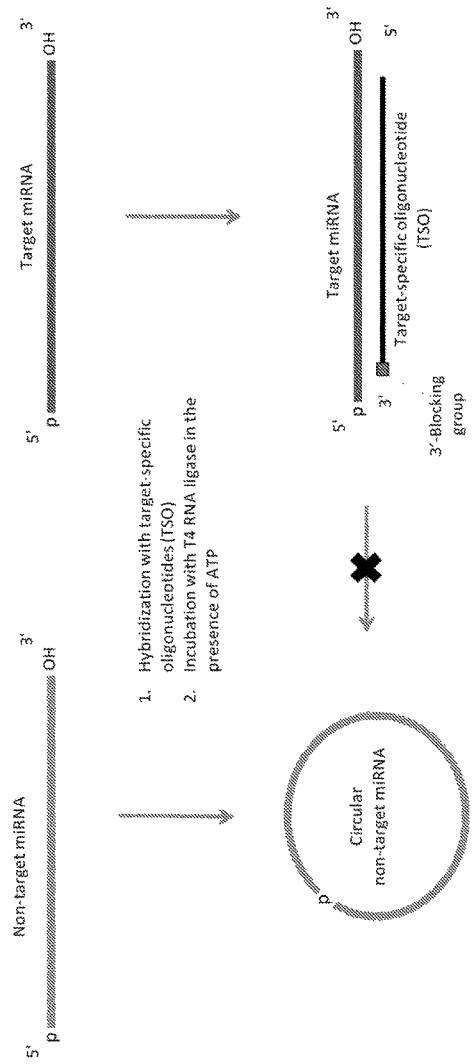
FIG. 1. Hybridization with target-specific oligonucleotides (TSO) suppresses circularization of miRNAs by T4 RNA ligase while making the miRNA ends available for adapter ligation and extension (miRNA is shown as an example). The circularization of unhybridized, non-target miRNAs prevents adapter ligation to or extension of their ends, thus excluding them from detection.

Before the present methods and compositions are described, it is to be understood that this invention is not limited to any particular method or composition described, as such may, of course, vary. It is also to be understood that the terminology used herein is for the purpose of describing particular embodiments only, and is not intended to be limiting, since the scope of the present invention will be limited only by the appended claims. Examples are put forth so as to provide those of ordinary skill in the art with a complete disclosure and description of how to make and use the present invention, and are not intended to limit the scope of what the inventors regard as their invention, nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order, which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g., polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The methods, compositions, and kits disclosed herein find use in a number of applications, such as applications that benefit from utilization of a stabilized primary RNA structure. For example, applications comprising the detection and/or quantification of target RNAs, construction of small RNAs for sequencing, microarray and RT-qPCR can benefit from methods, compositions, and kits for reducing and/or preventing the formation of secondary structures in a target RNA, ligation bias, amplification bias, and sequencing bias. These and other objects, advantages, and features of the invention will become apparent to those persons skilled in the art upon reading the details of the compositions and methods as more fully described herein.

Disclosed herein are methods, compositions, and kits comprising one or more target-specific oligonucleotides (TSOs). The methods, compositions, and kits generally comprise hybridizing one or more TSOs to one or more target RNAs to form a TSO-hybridized target RNA. The target RNAs can comprise small RNA molecules. The methods, compositions, and kits can further comprise attaching one or more adapters to the TSO-hybridized target RNA to form an adapter-ligated target RNA. The methods, compositions, and kits can further comprise attaching one or more adapters to the TSO-hybridized target RNA and/or adapter-ligated target RNA to form an adapter-target RNA. In some instances, the methods, compositions, and kits further comprise reverse transcribing at least a portion of the target RNA portion of the TSO-hybridized target RNA, adapter-ligated target RNA, or a derivative thereof (e.g., adapter-target RNA) to produce a cDNA copy of target RNA template. Alternatively, or additionally, the methods, compositions, and kits disclosed herein further comprise amplifying the TSO-hybridized target RNA, adapter-ligated target RNA, or a derivative thereof (e.g., adapter-target RNA, cDNA target RNA) to produce an amplified target RNA-specific sequence. The methods, compositions, and kits disclosed herein can further comprise isolating a TSO-hybridized target RNA, adapter-ligated target RNA, and/or a derivative thereof (e.g., adapter-target RNA, cDNA target RNA, amplified target RNA) to produce an isolated target RNA. The methods, compositions, and kits disclosed herein can further comprise quantifying the target RNA by detecting the TSO-hybridized target RNA, adapter-ligated target RNA, and/or a derivative thereof (e.g., adapter-target RNA, cDNA target RNA, amplified target RNA). In other instances, the methods, compositions, and kits further comprise sequencing the TSO-hybridized target RNA, adapter-ligated target RNA, and/or a derivative thereof (e.g., linker-target RNA, amplified target RNA, cDNA target RNA, isolated target RNA).

Further disclosed herein are methods, compositions, and kits for attaching one or more adapters to a target RNA or derivative thereof (e.g., TSO-hybridized target RNA). Generally, the methods, compositions, and kits for attaching one or more adapters to a target RNA or derivative thereof comprise: (a) hybridizing one or more TSOs to a target RNA to produce a TSO-hybridized target RNA; and (b) attaching one or more adapters to the target RNA portion of the TSO-hybridized target RNA to produce an adapter-ligated target RNA. In some instances, attachment of the adapters to the target RNA portion is not significantly susceptible to ligation bias.

Alternatively, or additionally, the methods, compositions, and kits disclosed herein can be used to attach a linker to a target RNA or a derivative thereof (e.g., TSO-hybridized target RNA, adapter-ligated target RNA). Generally, the methods, compositions, and kits comprise: (a) hybridizing one or more TSOs to a target RNA to produce a TSO-hybridized target RNA; and (b) attaching one or more linkers to the target RNA portion of the TSO-hybridized target RNA or a derivative thereof to produce linker-target RNA. The methods, compositions, and kits disclosed herein can further comprise attaching one or more adapters to the target RNA portion of the TSO to produce an adapter-ligated target RNA. In some instances, the derivative of the TSO-hybridized target RNA is the adapter-ligated target RNA.

In some instances, the methods, compositions, and kits disclosed are used to reduce ligation bias. The methods, compositions, and kits generally comprise: (a) hybridizing one or more TSOs to a target RNA to produce a TSO-hybridized target RNA; and (b) attaching one or more linkers and/or one or more adapters to the target RNA portion of the TSO-hybridized target RNA or a derivative thereof to produce linker-target RNA or adapter-ligated target RNA, respectively, thereby reducing ligation bias. In some instances, reducing ligation bias comprises improving efficiency of ligation of a linker and/or an adapter to a target RNA.

Alternatively, or additionally, the methods, compositions, and kits disclosed herein are used to reduce amplification bias. Generally, the methods, compositions, and kits comprise: (a) hybridizing one or more TSOs to a target RNA to produce a TSO-hybridized target RNA; and (b) amplifying the TSO-hybridized target RNA or a derivative thereof, thereby reducing amplification bias. In some instances, reducing amplification bias comprises improving amplification efficiency of one or more target RNAs.

In other instances, the methods, compositions, and kits disclosed herein are used to reduce sequence-dependent bias. The methods, compositions, and kits disclosed herein can be used to reduce sequencing bias. The methods, compositions, and kits generally comprise: (a) hybridizing one or more TSOs to a target RNA to produce a TSO-hybridized target RNA; and (b) sequencing the TSO-hybridized target RNA or a derivative thereof, thereby reducing sequence-dependent bias. In some instances, reducing sequence-dependent bias comprises improving sequencing efficiency of one or more target RNAs.

In other instances, the methods, compositions, and kits disclosed herein can be used to amplify a target RNA. The methods, compositions, and kits generally comprise: (a) hybridizing one or more TSOs to a target RNA to produce a TSO-hybridized target RNA; and (b) amplifying the TSO-hybridized target RNA or a derivative thereof.

In other instances, the methods, compositions, and kits disclosed herein can be used to reverse transcribe a target RNA. Generally, the methods, compositions, and kits comprise: (a) hybridizing one or more TSOs to a target RNA to produce a TSO-hybridized target RNA; and (b) reverse transcribing the TSO-hybridized target RNA or a derivative thereof.

In other instances, the methods, compositions, and kits disclosed herein can be used to sequence a target RNA. The methods, compositions, and kits generally comprise: (a) hybridizing one or more TSOs to a target RNA to produce a TSO-hybridized target RNA; and (b) sequencing the TSO-hybridized target RNA or a derivative thereof.

The methods, compositions, and kits disclosed herein can be used to quantify a target RNA. Generally, the methods, compositions, and kits comprise: (a) hybridizing one or more TSOs to a target RNA to produce a TSO-hybridized target RNA; and (b) detecting the TSO-hybridized target RNA or a derivative thereof, thereby quantifying the target RNA.

In some instances, the methods, compositions, and kits disclosed herein can reduce or prevent the formation of a secondary structure in the target RNA. The methods, compositions, and kits generally comprise hybridizing one or more TSOs to a target RNA to produce a TSO-hybridized target RNA, thereby preventing the formation of a secondary structure in the target RNA.

In other instances, the methods, compositions, and kits disclosed herein can be used to construct a target RNA library. Generally, the methods, compositions, and kits comprise: (a) hybridizing one or more TSOs to a target RNA to produce a TSO-hybridized target RNA; and (b) isolating the TSO-hybridized target RNA or a derivative thereof, thereby constructing a target RNA library.

As used herein, the terms "derivative of a target RNA", "target RNA derivative", "product of a target RNA" are used interchangeably and refer to any product or derivative of a target RNA disclosed herein. In some instances, derivatives of target RNA comprise the products of a reaction comprising a target RNA. For example, derivatives of target RNAs include, but are not limited to, TSO-hybridized target RNA, adapter-ligated target RNA, hapten-adapter ligated target RNA, probe-adapter ligated target RNA, tag-adapter ligated target RNA, cRNA, amplified target RNA, sequenced target RNA, etc.

I. Target-Specific Oligonucleotides (TSOs)

The methods, compositions, and kits disclosed herein often comprise a target-specific oligonucleotide. As used herein, a "target-specific oligonucleotide" ("TSO") is an oligonucleotide that can hybridize to a target RNA as disclosed herein. The TSOs disclosed herein can comprise one or more nucleotide residues selected from: deoxyribonucleic acid (DNA), ribonucleic acid (RNA), chemically modified sugar derivatives of DNA or RNA (e.g., 2'-OMe, or 2'-fluoro (2'-F), chemically modified nucleobase derivatives of DNA or RNA, abasic sites, a mimetic of DNA or RNA, and any combination thereof. In some instances, the TSOs further comprise one or more non-natural analogs. The non-natural analogs include, but are not limited to, peptide nucleic acid (PNA) linkages and Locked Nucleic Acid (LNA) linkages.

In some instances, at least one TSO comprises a sequence selected from any of SEQ ID NOs: 22-51, or a portion thereof. In other instances, at least one TSO comprises three or more consecutive sequences selected from any of SEQ ID NOs: 22-51. In other instances, at least one TSO comprises four or more consecutive sequences selected from any of SEQ ID NOs: 22-51. Alternatively, at least one TSO comprises five or more consecutive sequences selected from any of SEQ ID NOs: 22-51. In other instances, at least one TSO comprises ten or more consecutive sequences selected from any of SEQ ID NOs: 22-51. In other instances, at least one TSO comprises fifteen or more consecutive sequences selected from any of SEQ ID NOs: 22-51.

In some instances, at least one TSO comprises a sequence that is at least about 50% complementary to a sequence selected from any of SEQ ID NOs: 22-51, or a portion thereof. In other instances, at least one TSO comprises a sequence that is at least about 60% complementary to a sequence selected from any of SEQ ID NOs: 22-51, or a portion thereof. In other instances, at least one TSO comprises a sequence that is at least about 70% complementary to a sequence selected from any of SEQ ID NOs: 22-51, or a portion thereof. Alternatively, at least one TSO comprises a sequence that is at least about 75% complementary to a sequence selected from any of SEQ ID NOs: 22-51, or a portion thereof. In other instances, at least one TSO comprises a sequence that is at least about 80% complementary to a sequence selected from any of SEQ ID NOs: 22-51, or a portion thereof. In other instances, at least one TSO comprises a sequence that is at least about 85% complementary to a sequence selected from any of SEQ ID NOs: 22-51, or a portion thereof. Alternatively, at least one TSO comprises a sequence that is at least about 90% complementary to a sequence selected from any of SEQ ID NOs: 22-51, or a portion thereof. In other instances, at least one TSO comprises a sequence that is at least about 95% complementary to a sequence selected from any of SEQ ID NOs: 22-51, or a portion thereof. In other instances, at least one TSO comprises a sequence that is at least about 97% complementary to a sequence selected from any of SEQ ID NOs: 22-51, or a portion thereof.

The length of the TSO can be between about 5 nucleotides to one fewer nucleotide than the length of the target RNA. In other instances, the length of the TSO is between about 8 nucleotides to one fewer nucleotide than the length of the target RNA. Alternatively, the length of the TSO is between about 10 nucleotides to one fewer nucleotide than the length of the target RNA. The length of the TSO can be between about 10 nucleotides to one fewer nucleotide than the length of the target RNA. In some instances, the length of the TSO is between about 12 nucleotides to one fewer nucleotide than the length of the target RNA. In other instances, the length of the TSO is between about 14 nucleotides to one fewer nucleotide than the length of the target RNA. Alternatively, the length of the TSO is between about 16 nucleotides to one fewer nucleotide than the length of the target RNA. In some instances, the length of the TSO is between about 13 to about 22 nucleotides. In other instances, the length of the TSO is between about 15 to about 22 nucleotides. The length of the TSO can be between 17 to about 22 nucleotides. In some instances, the length of the TSO is between about 13 to about 20 nucleotides. In other instances, the length of the TSO is between about 15 to about 20 nucleotides. The length of the TSO can be between 17 to about 20 nucleotides. In some instances, the length of the TSO is between about 13 to about 19 nucleotides. In other instances, the length of the TSO is between about 15 to about 19 nucleotides. The length of the TSO can be between 17 to about 19 nucleotides. In some instances, the length of the TSO is between about 13 to about 18 nucleotides. In other instances, the length of the TSO is between about 15 to about 18 nucleotides. The length of the TSO can be between 17 to about 18 nucleotides.

In some instances, the length of TSO is at least about 5, 6, 7, 8, 9, 10, 11, 12, 13, 14, 15, 16, 17, 18, 19, 20, 21, 22, 23, 24, 25, 26, 27, 28, 29, or 30 nucleotides. In other instances, the length of the TSO can be at least about 14 nucleotides. In other instances, the length of the TSO is at least about 15 nucleotides. Alternatively, the length of the TSO is at least about 16 nucleotides. The length of the TSO can be at least about 17 nucleotides. In some instances, the length of the TSO is at least about 18 nucleotides. In other instances, the length of the nucleotide is at least about 19 nucleotides. Alternatively, the length of the TSO is at least about 20 nucleotides.

The length of the TSO can be at least about one fewer nucleotide to at least ten fewer nucleotides than the length of the target RNA. The length of the TSO can be at least about one fewer nucleotide than the length of the target RNA. Alternatively, the length of the TSO is at least about two fewer nucleotides than the length of the target RNA. In some instances, the length of the TSO is at least about three fewer nucleotides than the length of the target RNA. In other instances, the length of the TSO can be at least about four fewer nucleotides than the length of the target RNA. Alternatively, the length of the TSO is at least about five fewer nucleotides than the length of the target RNA. In some instances, the length of the TSO is at least about six fewer nucleotides than the length of the target RNA. In other instances, the length of the TSO is at least about seven fewer nucleotides than the length of the target RNA.

In some embodiments, at least one TSO is hybridized to the target RNA. In other embodiments, two or more TSOs are hybridized to different regions of the same target RNA. Alternatively, three or more TSOs are hybridized to different regions of the same target RNA. In some instances, at least about 4, 5, 6, 7, 8, 9, 10, or more TSOs are hybridized to different regions of the same target RNA.

In some instances, at least about two TSOs are hybridized to the target RNAs. In other instances, at least about three TSOs are hybridized to the target RNAs. Alternatively, or additionally, at least about five TSOs are hybridized to the target RNAs. In some instances, at least about ten TSOs are hybridized to the target RNAs. In other instances, at least about twenty TSOs are hybridized to the target RNAs. Alternatively, or additionally, at least about thirty TSOs are hybridized to the target RNAs. In some instances, at least about 40, 50, 60, 70, 80, 90, 100, 200, 300, 400, 500, 600, 700, 800, 900, 1000 or more TSOs are hybridized to the target RNAs. The TSOs can comprise the same sequence.

Alternatively, at least two TSOs comprise different sequences. The TSOs can hybridize to copies of the same target RNA. Alternatively, the TSOs can hybridize to at least two different target RNAs.

In some instances, the TSO comprises a sequence that is complementary to the sequence of the target RNA. The sequence of the TSO can be at least about 50% to about 100% complementary to the sequence of the target RNA. In some instances, the sequence of the TSO is at least about 70% complementary to the sequence of the target RNA. In other instances, the sequence of the TSO is at least about 75% complementary to the sequence of the target RNA. Alternatively, the sequence of the TSO is at least about 80% complementary to the sequence of the target RNA. The sequence of the TSO can be at least about 85% complementary to the sequence of the target RNA. In some instances, the sequence of the TSO is at least about 87% complementary to the sequence of the target RNA. In other instances, the sequence of the TSO is at least about 90% complementary to the sequence of the target RNA. Alternatively, the sequence of the TSO is at least about 95% complementary to the sequence of the target RNA. The sequence of the TSO can be at least about 97% complementary to the sequence of the target RNA. In some instances, the sequence of the TSO is at least about 98% complementary to the sequence of the target RNA. In other instances, the sequence of the TSO is at least about 99% complementary to the sequence of the target RNA.

The sequence of the TSO can comprise about 5 or fewer mismatches from sequence of the target RNA. In some instances, the sequence of the TSO comprises about 4 or fewer mismatches from sequence of the target RNA. In other instances, the sequence of the TSO comprises about 3 or fewer mismatches from sequence of the target RNA. Alternatively, the sequence of the TSO comprises about 2 or fewer mismatches from sequence of the target RNA. The sequence of the TSO can comprise about 1 or fewer mismatches from sequence of the target RNA. Alternatively, the sequence of the TSO comprises about zero mismatches from sequence of the target RNA.

In some instances, the TSO hybridizes to the target RNA to produce a TSO-hybridized target RNA, wherein the TSO-hybridized target RNA comprises one or more overhangs on the target RNA. In some instances, the overhangs are single-stranded. In some instances, the overhangs comprise non-hybridized regions on the target RNA. In some instances, the TSO-hybridized target RNA comprises an overhang at only one end of the target RNA. In other instances, the TSO-hybridized target RNA comprises overhangs at both ends of the target RNA, The overhang can be at the 5' end of the target RNA (5'-ooverhang). Alternatively, or additionally, the overhang is at the 3' end of the target RNA (3'-overhang). The TSO-hybridized target RNA can comprise an overhang at the 5' end of the target RNA and an overhang at the 3' end of the target RNA.

The overhang can comprise between about 1 to about 14 nucleotides. In some instances, the overhang can comprise between about 1 to about 12 nucleotides. In other instances, the overhang can comprise between about 1 to about 10 nucleotides. Alternatively, the overhang can comprise between about 1 to about 8 nucleotides. The overhang can comprise between about 1 to about 6 nucleotides. In some instances, the overhang can comprise between about 1 to about 5 nucleotides. In other instances, the overhang can comprise between about 1 to about 5 nucleotides. Alternatively, the overhang can comprise between about 1 to about 3 nucleotides. The overhang can comprise between about 1 to about 2 nucleotides.

The overhang can comprise at least about 1 nucleotide. In some instances, the overhang comprises at least about 2 nucleotides. In other instances, the overhang comprises at least about 3 nucleotides. Alternatively, the overhang comprises at least about 4 nucleotides. The overhang can comprise at least about 5 nucleotides. In some instances, the overhang comprises at least about 6 nucleotides. In other instances, the overhang comprises at least about 7 nucleotides. Alternatively, the overhang comprises at least about 8 nucleotides. The overhang can comprise at least about 9 nucleotides. In some instances, the overhang comprises at least about 10 nucleotides. In other instances, the overhang comprises at least about 11 nucleotides. Alternatively, the overhang comprises at least about 12 nucleotides.

In some instances, the number of nucleotides of the 5'-overhang is the same number of nucleotides of the 3'-overhang. For example, the 5'-overhang comprises 2 nucleotides and the 3'-overhang comprises 2 nucleotides. In other instances, the number of nucleotides of the 5'-overhang is less than the number of nucleotides in the 3'-overhang. For example, the 5'-overhang comprises zero nucleotides and the 3'-overhang comprises 4 nucleotides. In another example, the 5'-overhang comprises 1 nucleotide and the 3'-overhang comprises 3 nucleotides. Alternatively, the number of nucleotides of the 5'-overhang is greater than the number of nucleotides in the 3'-overhang. For example, the 5'-overhang comprises 4 nucleotides and the 3'-overhang comprises zero nucleotides. In another example, the 5'-overhang comprises 3 nucleotides and the 3'-overhang comprises 1 nucleotide.

In some instances, the 5'-overhang comprises 6 nucleotides and the 3'-overhang comprises zero nucleotides. In other instances, the 5'-overhang comprises 6 nucleotides and the 3'-overhang comprises 1 nucleotide. Alternatively, the 5'-overhang comprises 6 nucleotides and the 3'-overhang comprises 2 nucleotides. The 5'-overhang can comprise 6 nucleotides and the 3'-overhang can comprise 3 nucleotides. In some instances, the 5'-overhang comprises 6 nucleotides and the 3'-overhang comprises 4 nucleotides. In other instances, the 5'-overhang comprises 6 nucleotides and the 3'-overhang comprises 5 nucleotides. Alternatively, the 5'-overhang comprises 6 nucleotides and the 3'-overhang comprises 6 nucleotides. The 5'-overhang can comprise 6 nucleotides and the 3'-overhang can comprise 7 nucleotides. The 5'-overhang can comprise 6 nucleotides and the 3'-overhang can comprise 8 nucleotides. In some instances, the 5'-overhang comprises 6 nucleotides and the 3'-overhang comprises 9 nucleotides. In other instances, the 5'-overhang comprises 6 nucleotides and the 3'-overhang comprises 10 nucleotides. Alternatively, the 5'-overhang comprises 6 nucleotides and the 3'-overhang comprises 11 nucleotides.

In some instances, the 5'-overhang comprises 5 nucleotides and the 3'-overhang comprises zero nucleotides. In other instances, the 5'-overhang comprises 5 nucleotides and the 3'-overhang comprises 1 nucleotide. Alternatively, the 5'-overhang comprises 5 nucleotides and the 3'-overhang comprises 2 nucleotides. The 5'-overhang can comprise 5 nucleotides and the 3'-overhang can comprise 3 nucleotides. In some instances, the 5'-overhang comprises 5 nucleotides and the 3'-overhang comprises 4 nucleotides. In other instances, the 5'-overhang comprises 5 nucleotides and the 3'-overhang comprises 5 nucleotides. Alternatively, the 5'-overhang comprises 5 nucleotides and the 3'-overhang comprises 6 nucleotides. The 5'-overhang can comprise 5 nucleotides and the 3'-overhang can comprise 7 nucleotides. The 5'-overhang can comprise 5 nucleotides and the 3'-overhang can comprise 8 nucleotides. In some instances, the 5'-overhang comprises 5 nucleotides and the 3'-overhang comprises 9 nucleotides. In other instances, the 5'-overhang comprises 5 nucleotides and the 3'-overhang comprises 10 nucleotides. Alternatively, the 5'-overhang comprises 5 nucleotides and the 3'-overhang comprises 11 nucleotides.

In some instances, the 5'-overhang comprises 4 nucleotides and the 3'-overhang comprises zero nucleotides. In other instances, the 5'-overhang comprises 4 nucleotides and the 3'-overhang comprises 1 nucleotide. Alternatively, the 5'-overhang comprises 4 nucleotides and the 3'-overhang comprises 2 nucleotides. The 5'-overhang can comprise 4 nucleotides and the 3'-overhang can comprise 3 nucleotides. In some instances, the 5'-overhang comprises 4 nucleotides and the 3'-overhang comprises 4 nucleotides. In other instances, the 5'-overhang comprises 4 nucleotides and the 3'-overhang comprises 5 nucleotides. Alternatively, the 5'-overhang comprises 4 nucleotides and the 3'-overhang comprises 6 nucleotides. The 5'-overhang can comprise 4 nucleotides and the 3'-overhang can comprise 7 nucleotides. The 5'-overhang can comprise 4 nucleotides and the 3'-overhang can comprise 8 nucleotides. In some instances, the 5'-overhang comprises 4 nucleotides and the 3'-overhang comprises 9 nucleotides. In other instances, the 5'-overhang comprises 4 nucleotides and the 3'-overhang comprises 10 nucleotides. Alternatively, the 5'-overhang comprises 4 nucleotides and the 3'-overhang comprises 11 nucleotides.

In some instances, the 5'-overhang comprises 3 nucleotides and the 3'-overhang comprises zero nucleotides. In other instances, the 5'-overhang comprises 3 nucleotides and the 3'-overhang comprises 1 nucleotide. Alternatively, the 5'-overhang comprises 3 nucleotides and the 3'-overhang comprises 2 nucleotides. The 5'-overhang can comprise 3 nucleotides and the 3'-overhang can comprise 3 nucleotides. In some instances, the 5'-overhang comprises 3 nucleotides and the 3'-overhang comprises 4 nucleotides. In other instances, the 5'-overhang comprises 3 nucleotides and the 3'-overhang comprises 5 nucleotides. Alternatively, the 5'-overhang comprises 3 nucleotides and the 3'-overhang comprises 6 nucleotides. The 5'-overhang can comprise 3 nucleotides and the 3'-overhang can comprise 7 nucleotides. The 5'-overhang can comprise 3 nucleotides and the 3'-overhang can comprise 8 nucleotides. In some instances, the 5'-overhang comprises 3 nucleotides and the 3'-overhang comprises 9 nucleotides. In other instances, the 5'-overhang comprises 3 nucleotides and the 3'-overhang comprises 10 nucleotides. Alternatively, the 5'-overhang comprises 3 nucleotides and the 3'-overhang comprises 11 nucleotides.

In some instances, the 5'-overhang comprises 2 nucleotides and the 3'-overhang comprises zero nucleotides. In other instances, the 5'-overhang comprises 2 nucleotides and the 3'-overhang comprises 1 nucleotide. Alternatively, the 5'-overhang comprises 2 nucleotides and the 3'-overhang comprises 2 nucleotides. The 5'-overhang can comprise 2 nucleotides and the 3'-overhang can comprise 3 nucleotides. In some instances, the 5'-overhang comprises 2 nucleotides and the 3'-overhang comprises 4 nucleotides. In other instances, the 5'-overhang comprises 2 nucleotides and the 3'-overhang comprises 5 nucleotides. Alternatively, the 5'-overhang comprises 2 nucleotides and the 3'-overhang comprises 6 nucleotides. The 5'-overhang can comprise 2 nucleotides and the 3'-overhang can comprise 7 nucleotides. The 5'-overhang can comprise 2 nucleotides and the 3'-overhang can comprise 8 nucleotides. In some instances, the 5'-overhang comprises 2 nucleotides and the 3'-overhang comprises 9 nucleotides. In other instances, the 5'-overhang comprises 2 nucleotides and the 3'-overhang comprises 10 nucleotides. Alternatively, the 5'-overhang comprises 2 nucleotides and the 3'-overhang comprises 11 nucleotides.

In some instances, the 5'-overhang comprises 1 nucleotide and the 3'-overhang comprises zero nucleotides. In other instances, the 5'-overhang comprises 1 nucleotide and the 3'-overhang comprises 1 nucleotide. Alternatively, the 5'-overhang comprises 1 nucleotide and the 3'-overhang comprises 2 nucleotides. The 5'-overhang can comprise 1 nucleotide and the 3'-overhang can comprise 3 nucleotides. In some instances, the 5'-overhang comprises 1 nucleotide and the 3'-overhang comprises 4 nucleotides. In other instances, the 5'-overhang comprises 1 nucleotide and the 3'-overhang comprises 5 nucleotides. Alternatively, the 5'-overhang comprises 1 nucleotide and the 3'-overhang comprises 6 nucleotides. The 5'-overhang can comprise 1 nucleotide and the 3'-overhang can comprise 7 nucleotides. The 5'-overhang can comprise 1 nucleotide and the 3'-overhang can comprise 8 nucleotides. In some instances, the 5'-overhang comprises 1 nucleotide and the 3'-overhang comprises 9 nucleotides. In other instances, the 5'-overhang comprises 1 nucleotide and the 3'-overhang comprises 10 nucleotides. Alternatively, the 5'-overhang comprises 1 nucleotide and the 3'-overhang comprises 11 nucleotides.

In some instances, the 5'-overhang comprises zero nucleotides and the 3'-overhang comprises zero nucleotides. In other instances, the 5'-overhang comprises zero nucleotides and the 3'-overhang comprises 1 nucleotide. Alternatively, the 5'-overhang comprises zero nucleotides and the 3'-overhang comprises 2 nucleotides. The 5'-overhang can comprise zero nucleotides and the 3'-overhang can comprise 3 nucleotides. In some instances, the 5'-overhang comprises zero nucleotides and the 3'-overhang comprises 4 nucleotides. In other instances, the 5'-overhang comprises zero nucleotides and the 3'-overhang comprises 5 nucleotides. Alternatively, the 5'-overhang comprises zero nucleotides and the 3'-overhang comprises 6 nucleotides. The 5'-overhang can comprise zero nucleotides and the 3'-overhang can comprise 7 nucleotides.

In some instances, the TSO hybridizes to the target RNA to produce a TSO-hybridized target RNA, wherein the TSO ends of the TSO portion of the TSO-hybridized target RNA does not extend beyond the ends of the target RNA portion of the TSO-hybridized target RNA. In some instances, at least one end of the TSO is shorter than the target RNA of the TSO-hybridized target RNA. For example, the 5'-end of the TSO is at least about one nucleotide shorter than the 3'-end of the target RNA. In another example, the 3'-end of the TSO is at least about one nucleotide shorter than the 5'-end of the target RNA. In some instances, the 5'-end and/or the 3'-end of the TSO portion of the TSO-hybridized target RNA is at least about 0, 1, 2, 3, 4, 5, 6, 7, 8, 9, or 10 nucleotides shorter than the 3'-end and/or 5'-end of the target RNA of the TSO-hybridized target RNA.

In other instances, both ends of the TSO are shorter than the target RNA of the TSO-hybridized target RNA. For example, the 5'-end of the TSO is at least about one nucleotide shorter than the 3'-end of the target RNA and the 3'-end of the TSO is at least about one nucleotide shorter than the 5'-end of the target RNA. In some instances, the 5'-end and/or the 3'-end of the TSO portion of the TSO-hybridized target RNA is at least about 1, 2, 3, 4, 5, 6, 7, 8, 9, or 10 nucleotides shorter than the 3'-end and/or 5'-end of the target RNA of the TSO-hybridized target RNA.

The methods, compositions, and kits disclosed herein can comprise a plurality of TSOs. In some instances, the plurality of TSOs comprises identical TSOs. For example, the plurality of TSOs comprises TSOs comprising the same sequence and length.

In other instances, the plurality of TSOs comprises two or more different TSOs. For example, the two or more different TSOs can comprise different sequences. In another example, the two or more different TSOs can comprise different lengths. In some instances, the two or more different TSOs comprise different sequences and different lengths.

The plurality of TSOs can comprise at least about two or more different TSOs. In other instances, the plurality of TSOs comprise at least about three or more different TSOs. Alternatively, the plurality of TSOs comprise at least about four or more different TSOs. In some instances, the plurality of TSOs comprise at least about four or more different TSOs. The plurality of TSOs can comprise at least about five or more different TSOs. In other instances, the plurality of TSOs comprise at least about six or more different TSOs. Alternatively, the plurality of TSOs comprise at least about seven or more different TSOs. In some instances, the plurality of TSOs comprise at least about eight or more different TSOs. The plurality of TSOs can comprise at least about ten or more different TSOs. In other instances, the plurality of TSOs comprise at least about fifteen or more different TSOs. Alternatively, the plurality of TSOs comprise at least about twenty or more different TSOs. In some instances, the plurality of TSOs comprise at least about 25, 30, 35, 40, 45, 50, 55, 60, 65, 70, 75, 80, 85, 90, 95, 100 or more different TSOs. In other instances, the plurality of TSOs comprise at least about 150, 200, 250, 300, 350, 400, 450, 500, 550, 600, 650, 700, 750, 800, 850, 900, 950, 1000 or more different TSOs.

In some instances, the TSOs as disclosed herein comprise one or more internal structures. In some instances, the one or more internal structures comprise a hairpin. In some instances, the one or more internal structures cannot be bypassed and/or replicated by a DNA polymerase. In some instances, the one or more internal structures reduce and/or prevent replication of the TSO. In some instances, the one or more internal structures reduce and/or prevent replication of the TSO by at least about 10%, 20%, 30%, 40%, 50%, 60% or more as compared to a TSO without one or more internal structures. In other instances, the one or more internal structures reduce and/or prevent replication of the TSO by at least about 65%, 70%, 75%, 80%, 85%, 90%, 95%, 97%, or more as compared to a TSO without one or more internal structures.

The TSOs for use in the methods, compositions, and kits disclosed herein can further comprise one or more blocking groups. In some instances, the TSO comprises a blocking group at its 5' end (e.g., 5' blocking group). In other instances, the TSO comprises a blocking group at its 3' end (e.g., 3' blocking group). Alternatively, the TSO comprises a blocking group at its 5' end and its 3' end.

In some instances, the blocking group comprises a termination group that is a 3'-phosphate (3'-p or Np); a 3'-amino; a 2',3'-dideoxy nucleoside (ddN); a 3'-inverted (3'-3') deoxynucleoside (idN); a 3'-inverted abasic site; or a 3'-non-nucleoside linker (n-linker). In some embodiments, the TSO comprises a blocking group at its 5' end that prevents its phosphorylation, e.g., a 5'-OMe or a non-nucleotide linker. In some embodiments, the TSO comprises one or more residues that cannot be replicated by DNA polymerase; e.g., anabasic site(s) or nucleoside(s) with 2'-OMe or 2'-F modifications.

In some instances, the 3' blocking group on the TSO reduces and/or prevents extension of the 3' end of TSO. In some instances, the 3' blocking group on the TSO reduces and/or prevents extension of the 3' end of TSO by a reverse transcriptase. In other instances, the 3' blocking group on the TSO reduces and/or prevents extension of the 3' end of TSO by a DNA polymerase. In some instances, the 3' blocking group on the TSO reduces and/or prevents extension of the 3' end of the TSO by at least about 10%, 20%, 30%, 40%, 50%, 60% or more as compared to a TSO without a 3' blocking group. In other instances, the 3' blocking group on the TSO reduces and/or prevents extension of the 3' end of the TSO by at least about 65%, 70%, 75%, 80%, 85%, 90%, 95%, 97%, or more as compared to a TSO without a 3' blocking group.

In some instances, the blocking group on the TSO reduces and/or prevents ligation to the 5' and/or 3' end of the TSO. The blocking group on the TSO can reduce and/or prevent ligation to the 5' end and/or 3' end of the TSO by at least about 10%, 20%, 30%, 40%, 50%, 60% or more as compared to a TSO without one or more blocking groups. In other instances, the blocking group on the TSO reduces and/or prevents ligation to the 5' end and/or 3' end of the TSO by at least about 65%, 70%, 75%, 80%, 85%, 90%, 95%, 97%, or more as compared to a TSO without one or more blocking groups.

In some instances, the 5' blocking group on the TSO reduces and/or prevents phosphorylation of the 5' end of the TSO. The blocking group on the TSO can reduce and/or prevent phosphorylation of the 5' end of the TSO by at least about 10%, 20%, 30%, 40%, 50%, 60% or more as compared to a TSO without a 5' blocking group. In other instances, the blocking group on the TSO reduces and/or prevents phosphorylation of the 5' end of the TSO by at least about 65%, 70%, 75%, 80%, 85%, 90%, 95%, 97%, or more as compared to a TSO without a 5' blocking group.

II. Target RNAs

The methods, compositions and kits disclosed herein often comprise hybridization of a TSO to a target RNA. As used herein, a "target RNA" is a small RNA molecule. In some instances, a target RNA or a small RNA molecule can also be referred to as a non-coding RNA. A non-limiting list of target RNAs includes microRNAs (miRNAs), siRNA, piRNA, ncRNA, snRNA, snoRNA, pre-miRNAs. Target RNAs can also include fragments of larger coding RNAs (e.g., mRNA or viral RNAs) or non-coding RNAs (e.g., ribosomal RNAs, lncRNAs, pri-miRNAs). In some instances, the target RNA is a miRNA. In other instances, the target RNA is a siRNA or shRNA. The target RNA can be an ncRNA. The target RNA can be a small ncRNA.

Generally, a target RNA molecule disclosed herein comprises an RNA molecule with the following features: (a) size ranging from 15-to-150 nucleotides, and preferably from 20-to-90 nucleotides; (b) 5' ends selected from: 5'-phospate (5'-p); and 5'-hydroxyl (5'-OH), or 5'-cap, or 5'-triphosphate (5'-ppp), which if necessary are enzymatically converted to 5'-p before ligation and/or extension; (c) 3' groups at the 3' ends selected from: 3'-hydroxyl (3'-OH), 3'-phospate (3'-p), or 2',3'-cyclic phosphate (2',3'>p), which if necessary are enzymatically converted to 3'-OH before the ligation and/or extension; and/or (d) 2' groups at the 3' ends selected from: 2'-OH or 2'-oxymethyl (2'-OMe). In some instances, the choice for 5'-p and 3'-OH ends, which can be naturally occurring in miRNAs, is based on substrate requirements for enzymatic ligation and extension reactions.

In some instances, the length of the target RNA is between about 15 to about 150 nucleotides. In other instances, the length of the target RNA is between about 15 to about 125 nucleotides. Alternatively, the length of the target RNA is between about 15 to about 100 nucleotides. The length of the target RNA can be between about 15 to about 90 nucleotides. In some instances, the length of the target RNA is between about 17 to about 80 nucleotides. In other instances, the length of the target RNA is between about 17 to about 70 nucleotides. Alternatively, the length of the target RNA is between about 17 to about 60 nucleotides. The length of the target RNA can be between about 17 to about 50 nucleotides. In some instances, the length of the target RNA is between about 19 to about 40 nucleotides. In other instances, the length of the target RNA is between about 19 to about 30 nucleotides. Alternatively, the length of the target RNA is between about 19 to about 25 nucleotides. The length of the target RNA can be between about 19 to about 23 nucleotides. In some instances, the length of the target RNA is between about 20 to about 25 nucleotides. In other instances, the length of the target RNA is between about 20 to about 24 nucleotides. Alternatively, the length of the target RNA is between about 20 to about 23 nucleotides. The length of the target RNA can be between about 20 to about 22 nucleotides. In some instances, the length of the target RNA is between about 21 to about 25 nucleotides. In other instances, the length of the target RNA is between about 21 to about 24 nucleotides. Alternatively, the length of the target RNA is between about 21 to about 23 nucleotides. The length of the target RNA can be between about 21 to about 22 nucleotides.

The length of the target RNA can be at least about 17 nucleotides. In some instances, the length of the target RNA is at least about 18 nucleotides. In other instances, the length of the target RNA is at least about 19 nucleotides. Alternatively, the length of the target RNA is at least about 20 nucleotides. The length of the target RNA can be at least about 21 nucleotides. In some instances, the length of the target RNA is at least about 22 nucleotides. In other instances, the length of the target RNA is at least about 23 nucleotides. Alternatively, the length of the target RNA is at least about 24 nucleotides. The length of the target RNA can be at least about 25 nucleotides. In some instances, the length of the target RNA is at least about 26 nucleotides. In other instances, the length of the target RNA is at least about 27 nucleotides. Alternatively, the length of the target RNA is at least about 28 nucleotides.

The length of the target RNA can be less than about 30 nucleotides. In some instances, the length of the target RNA is less than about 29 nucleotides. In other instances, the length of the target RNA is less than about 28 nucleotides. Alternatively, the length of the target RNA is less than about 27 nucleotides. The length of the target RNA can be less than about 26 nucleotides. In some instances, the length of the target RNA is less than about 25 nucleotides. In other instances, the length of the target RNA is less than about 24 nucleotides. Alternatively, the length of the target RNA is less than about 23 nucleotides. The length of the target RNA can be less than about 22 nucleotides. In some instances, the length of the target RNA is less than about 21 nucleotides. In other instances, the length of the target RNA is less than about 20 nucleotides. Alternatively, the length of the target RNA is less than about 19 nucleotides. The length of the target RNA can be less than about 18 nucleotides. In some instances, the length of the target RNA is less than about 17 nucleotides. In other instances, the length of the target RNA is less than about 16 nucleotides. Alternatively, the length of the target RNA is less than about 15 nucleotides.

The methods, compositions, and kits disclosed herein can comprise hybridizing a plurality of TSOs to a plurality of target RNAs. In some instances, the plurality of target RNAs comprises target RNAs of identical sequences. In other instances, the plurality of target RNAs comprise different target RNAs. The different target RNAs can comprise different sequences. Alternatively, the different target RNAs comprise different lengths. In other instances, the different target RNAs comprise different isoforms of a target RNA. The different target RNAs can comprise different isomirs of a target RNA. The plurality of target RNAs can comprise the same type of small RNA molecule. For example, the plurality of target RNAs can comprise miRNAs. In another example, the plurality of RNAs can comprise siRNAs. Alternatively, the plurality of RNAs can comprise different types of small RNA molecules. For example, the plurality of target RNAs can comprise miRNAs and siRNAs.

The methods, compositions, and kits disclosed herein can increase the number of samples to be analyzed. In some instances, the number of samples to be analyzed increases by at least about 5%, 10%, 15%, 20%, 25%, 30%, 35%, 40%, 45%, 50%, 55% or more as compared to reactions without TSO. In other instances, the number of samples to be analyzed increases by at least about 60% or more as compared to reactions without TSO. Alternatively, the number of samples to be analyzed increases by at least about 65% or more as compared to reactions without TSO. The number of samples to be analyzed can increase by at least about 70% or more as compared to reactions without TSO. In some instances, the number of samples to be analyzed increases by at least 75% or more as compared to reactions without TSO. In other instances, the number of samples to be analyzed increases by at least about 80% or more as compared to reactions without TSO. Alternatively, the number of samples to be analyzed increases by at least about 85% or more as compared to reactions without TSO. The number of samples to be analyzed can increase by at least about 90% or more as compared to reactions without TSO. In some instances, the number of samples to be analyzed increases by at least about 95% or more as compared to reactions without TSO. In other instances, the number of samples to be analyzed increases by at least about 97% or more as compared to reactions without TSO.

In some instances, the target RNAs are low-copy target RNAs. In some instances, the methods, compositions, and kits facilitate detection of low-copy target RNAs. In some instances, the total number of low-copy target RNAs detected in a reaction comprising one or more TSOs is at least about 10%, 20%, 25%, 30%, 35%, 40%, 45%, 45%, or 50% higher than the total number of low-copy target RNAs detected in a reaction that does not comprise one or more TSOs. In other instances, the total number of low-copy target RNAs detected in a reaction comprising one or more TSOs is at least about 55% higher than the total number of low-copy target RNAs detected in a reaction that does not comprise one or more TSOs. Alternatively, the total number of low-copy target RNAs detected in a reaction comprising one or more TSOs is at least about 60% higher than the total number of low-copy target RNAs detected in a reaction that does not comprise one or more TSOs. The total number of low-copy target RNAs detected in a reaction comprising one or more TSOs can be at least about 65% higher than the total number of low-copy target RNAs detected in a reaction that does not comprise one or more TSOs. In some instances, the total number of low-copy target RNAs detected in a reaction comprising one or more TSOs is at least about 70% higher than the total number of low-copy target RNAs detected in a reaction that does not comprise one or more TSOs. In other instances, the total number of low-copy target RNAs detected in a reaction comprising one or more TSOs is at least about 75% higher than the total number of low-copy target RNAs detected in a reaction that does not comprise one or more TSOs. Alternatively, the total number of low-copy target RNAs detected in a reaction comprising one or more TSOs is at least about 80% higher than the total number of low-copy target RNAs detected in a reaction that does not comprise one or more TSOs. The total number of low-copy target RNAs detected in a reaction comprising one or more TSOs can be at least about 85% higher than the total number of low-copy target RNAs detected in a reaction that does not comprise one or more TSOs. In some instances, the total number of low-copy target RNAs detected in a reaction comprising one or more TSOs is at least about 90% higher than the total number of low-copy target RNAs detected in a reaction that does not comprise one or more TSOs. In other instances, the total number of low-copy target RNAs detected in a reaction comprising one or more TSOs is at least about 95% higher than the total number of low-copy target RNAs detected in a reaction that does not comprise one or more TSOs. Alternatively, the total number of low-copy target RNAs detected in a reaction comprising one or more TSOs is at least about 97% higher than the total number of low-copy target RNAs detected in a reaction that does not comprise one or more TSOs. The total number of low-copy target RNAs detected in a reaction comprising one or more TSOs can be at least about 99% higher than the total number of low-copy target RNAs detected in a reaction that does not comprise one or more TSOs.

III. Adapters

The methods, compositions, and kits disclosed herein can comprise one or more adapters. In some instances, the one or more adapters are attached to the target RNA. Alternatively, or additionally, the one or more adapters are attached to a linker, hapten, tag, probe, label, or a combination thereof. The adapters disclosed herein can comprise one or more deoxyribonucleic acid (DNA), ribonucleic acid (RNA), a chemically modified derivative thereof, a chemical analog thereof, a mimetic thereof, and combinations thereof. In some instances, the adapters further comprise one or more non-natural analogs. The non-natural analogs include, but are not limited to, peptide nucleic acid (PNA) linkages and Locked Nucleic Acid (LNA) linkages.

In some instances, the length of the adapter is between about 1 to about 100 nucleotides. In other instances, the length of the adapter is between about 10 to about 100 nucleotides. Alternatively, the length of the adapter is between about 20 to about 100 nucleotides. The length of the adapter can be between about 30 to about 100 nucleotides. In some instances, the length of the adapter is between about 40 to about 100 nucleotides. In other instances, the length of the adapter is between about 50 to about 100 nucleotides. Alternatively, the length of the adapter is between about 10 to about 90 nucleotides. The length of the adapter is between about 10 to about 80 nucleotides. In some instances, the length of the adapter is between about 10 to about 70 nucleotides. In other instances, the length of the adapter is between about 20 to about 80 nucleotides. Alternatively, the length of the adapter is between about 20 to about 70 nucleotides. The length of the adapter can be between about 20 to about 60 nucleotides. In some instances, the length of the adapter is between about 20 to about 50 nucleotides. In other instances, the length of the adapter is between about 20 to about 40 nucleotides. Alternatively, the length of the adapter is between about 30 to about 60 nucleotides. The length of the adapter is between about 30 to about 50 nucleotides.

In some instances, the length of the adapter is at least about 10 nucleotides. In other instances, the length of the adapter is at least about 20 nucleotides. Alternatively, the length of the adapter is at least about 30 nucleotides. The length of the adapter can be between about 40 nucleotides. In some instances, the length of the adapter is at least about 50 nucleotides. In other instances, the length of the adapter is at least about 60 nucleotides. Alternatively, the length of the adapter is at least about 70, 75, 80, 85, 90, 95, or 100 nucleotides.

In some instances, the length of the adapter is less than about 70 nucleotides. In other instances, the length of the adapter is less than about 60 nucleotides. Alternatively, the length of the adapter is less than about 55 nucleotides. The length of the adapter can be between about 50 nucleotides. In some instances, the length of the adapter is less than about 45 nucleotides. In other instances, the length of the adapter is less than about 30 nucleotides.

The adapters as disclosed herein can comprise a sequence that is not substantially complementary to the sequences of the RNA molecule present in the sample. In some instances, the sequence of the adapter is less than about 50% complementary to the sequence of an RNA molecule present in the sample. In other instances, the sequence of the adapter is less than about 40% complementary the sequence of an RNA molecule present in the sample. Alternatively, the sequence of the adapter is less than about 30% complementary the sequence of an RNA molecule present in the sample. The sequence of the adapter is less than about 20% complementary the sequence of an RNA molecule present in the sample. In some instances, the sequence of the adapter is less than about 15% complementary the sequence of an RNA molecule present in the sample. In other instances, the sequence of the adapter is less than about 10% complementary the sequence of an RNA molecule present in the sample. Alternatively, the sequence of the adapter is less than about 5% complementary the sequence of an RNA molecule present in the sample. The sequence of the adapter is less than about 2% complementary the sequence of an RNA molecule present in the sample.

The sequence of the adapters as disclosed herein can comprise less than about 10 consecutive nucleotides of a nucleic acid molecule present in the sample or of a nucleic acid molecule added to the sample. In some instances, the sequence of the adapters comprises less than about 8 consecutive nucleotides of a nucleic acid molecule present in the sample or of a nucleic acid molecule added to the sample. In other instances, the sequence of the adapters comprises less than about 6 consecutive nucleotides of a nucleic acid molecule present in the sample or of a nucleic acid molecule added to the sample. Alternatively, the sequence of the adapters comprises less than about 5 consecutive nucleotides of a nucleic acid molecule present in the sample or of a nucleic acid molecule added to the sample. The sequence of the adapters comprises less than about 4 consecutive nucleotides of a nucleic acid molecule present in the sample or of a nucleic acid molecule added to the sample. In some instances, the sequence of the adapters comprises less than about 3 consecutive nucleotides of a nucleic acid molecule present in the sample or of a nucleic acid molecule added to the sample. In other instances, the sequence of the adapters comprises less than about 2 consecutive nucleotides of a nucleic acid molecule present in the sample or of a nucleic acid molecule added to the sample. In some instances, the nucleic acid molecule added to the sample is a TSO, linker, label, tag, and/or probe.

In some instances, the adapters as disclosed herein cannot hybridize to a target RNA or a derivative thereof. In some instances, less than about 50% of the adapters can hybridize to the target RNA or derivative thereof. In other instances, less than about 40% of the adapters can hybridize to the target RNA or derivative thereof. Alternatively, less than about 30% of the adapters can hybridize to the target RNA or derivative thereof. In other instances, less than about 20% of the adapters can hybridize to the target RNA or derivative thereof. In some instances, less than about 10% of the adapters can hybridize to the target RNA or derivative thereof. In other instances, less than about 5% of the adapters can hybridize to the target RNA or derivative thereof. Alternatively, less than about 2% of the adapters can hybridize to the target RNA or derivative thereof. In some instances, less than about 1% of the adapters can hybridize to the target RNA or derivative thereof.

In some instances, the adapters as disclosed herein cannot hybridize to a nucleic acid molecule added to the sample. In some instances, less than about 50% of the adapters can hybridize to the nucleic acid molecule added to the sample. In other instances, less than about 40% of the adapters can hybridize to the nucleic acid molecule added to the sample. Alternatively, less than about 30% of the adapters can hybridize to the nucleic acid molecule added to the sample. In other instances, less than about 20% of the adapters can hybridize to the nucleic acid molecule added to the sample. In some instances, less than about 10% of the adapters can hybridize to the nucleic acid molecule added to the sample. In other instances, less than about 5% of the adapters can hybridize to the nucleic acid molecule added to the sample. Alternatively, less than about 2% of the adapters can hybridize to the nucleic acid molecule added to the sample. In some instances, less than about 1% of the adapters can hybridize to the nucleic acid molecule added to the sample. In some instances, the nucleic acid molecule added to the sample is a TSO. In other instances, the nucleic acid molecule added to the sample is a linker, label, tag, and/or probe.

In some instances, the adapters disclosed herein can be single-stranded (e.g., adapters for Solexa and 454 sequencing platforms). In some instances, the adapters can be double-stranded and have terminal overhangs of about 6-to-7 nucleotides that are complementary to target RNA ends (e.g., adapters for SOLiD and ION Torrent sequencing platforms).

The adapters disclosed herein can further comprise a promoter sequence for an RNA polymerase. For example, the adapter can comprise the antisense promoter strand for bacteriophage T7, SP6 or T3 RNA polymerases.

In some instances, the adapters disclosed herein further comprise a sequence for cloning. In some instances, the adapters disclosed herein further comprise a sequence for cloning, concatamerization and conventional Sanger sequencing as previously described (Hainer et al. 2008).

In some instances, the adapters as disclosed herein are for next-generation sequencing methods and further comprise a primer sequence for reverse transcription and/or PCR amplification such as Illumina's Solexa adapters (SEQ ID NO: 1-to-5). In some instances, the primer sequence can be used for reverse transcription. For example, the primer sequence that can be used for reverse transcription comprises SEQ ID NO: 3. In other instances, the primer sequence can be used for PCR amplification. Primer sequences that can be used for amplification include, but are not limited to, SEQ ID NO: 4 and SEQ ID NO: 5. Alternatively, or additionally, the primer sequence can be used sequencing. Examples of primer sequences for use in sequencing include, but are not limited to, SEQ ID NO: 6.

In some instances, the adapters disclosed herein can further comprise a sequence that is compatible with a sequencing reaction. In other instances, the adapters further comprise a sequence that is compatible with an amplification reaction. Alternatively, or additionally, the adapter further comprises a sequence that is compatible with a reverse transcription reaction.

In some instances, the adapters are attached to the target RNA portion of the TSO-hybridized target RNA to produce an adapter-ligated target RNA. The adapters can be attached to the 5' end of the target RNA (e.g., 5'-adapter) to produce a 5'-end adapter-ligated target RNA. Alternatively, or additionally, the adapters are attached to the 3' end of the target RNA (e.g., 3'-adapter) to produce a 3'-end adapter-ligated target RNA. In some instances, the adapters are added to the 5' end and the 3' end of the target RNA to produce a 5'-end and 3'-end adapter ligated target RNA. The 5'-adapter and the 3'-adapter can be attached simultaneously. In other instances, the 5'-adapter and the 3'-adapter are attached sequentially. For example, the 5'-adapter is attached to the target RNA prior to attachment of the 3'-adapter to the target RNA. In another example, the 5'-adapter is attached to the target RNA after attachment of the 3'-adapter to the target RNA. As used herein, the term "adapter-ligated target RNA" refers to a target RNA ligated to an adapter and can comprise 5'-end adapter-ligated target RNAs, 3'-end adapter-ligated target RNAs, and 5'-end and 3'-end adapter-ligated target RNAs.

The methods, compositions, and kits disclosed herein can comprise attachment of one or more adapters to the target RNA portion of the TSO-hybridized target RNA. Attachment of the one or more adapters to the target RNA portion of the TSO-hybridized target RNA can comprise conducting a ligation reaction to attach the one or more adapters to the target RNA.

IV. Haptens, Tags, Probes, and Linkers

In some instances, the methods, compositions, and kits disclosed herein comprise one or more adapters comprising one or more haptens. Haptens can comprise small molecules that can elicit an immune response. In some instances, the adapter comprises one or more haptens, wherein the one or more haptens comprise biotin or digoxigenin. In other instances, the haptens are selected from a list including, but not limited to, dinitrophenol (DNP), fluorescein, aniline, carboxyl derivatives of aniline (e.g., o-, m-, and p-aminobenzoic acid), and uroshiol. The 5'-adapter can further comprise one or more haptens. Alternatively, or additionally, the 3'-adapter further comprises one or more haptens. In some instances, the 5'-adapter and the 3'-adapter further comprise one or more haptens. In some instances, the 5'-adapter and the 3'-adapter comprise different haptens. For example, the 5'-adapter comprises a hapten comprising biotin and the 3'-adapter comprises a hapten comprising digoxigenin. In other instances, the 5'-adapter and the 3'-adapter comprise the same type of hapten. For example, both the 5'-adapter and the 3'-adapter comprise a hapten comprising biotin.

In other instances, the methods, compositions, and kits disclosed herein comprise one or more adapters comprising one or more signal moieties. For example, signal moieties include, but are not limited to, [5'-$^{32}$P]-labeled 5'-pNp-3' (pNp); 5'-pN-3'-n-linker-detectable moiety; 5'-AppN-3'-n-linker-detectable moiety; and 5'-pNpN-n-linker-detectable moiety. The 5'-adapter can further comprise one or more signal moieties. Alternatively, or additionally, the 3'-adapter further comprises one or more signal moieties. In some instances, the 5'-adapter and the 3'-adapter further comprise one or more signal moieties. In some instances, the 5'-adapter and the 3'-adapter comprise different signal moieties. In other instances, the 5'-adapter and the 3'-adapter comprise the same type of signal moiety. Non-limiting examples of signal moieties include fluorescent species (e.g., fluorescein and rhodamine dyes and green fluorescent protein) and nanoparticles (e.g., nanogold as described in U.S. Pat. No. 7,824,863).

Alternatively, or additionally, the methods, compositions and kits disclosed herein comprise one or more adapters comprising one or more tags or probes. A non-limiting list of probes includes molecular probes such as Molecular Beacons, Scorpion probes and TaqMan probes. A non-limiting list of tags includes biotin and digoxigenin. In some instances, the tags or probes comprise sequences that can be used for sandwich hybridization. The 5'-adapter can further comprise one or more tags or probes. Alternatively, or additionally, the 3'-adapter further comprises one or more tags or probes. In some instances, the 5'-adapter and the 3'-adapter further comprise one or more tags or probes. In some instances, the 5'-adapter and the 3'-adapter comprise different tags or probes. In other instances, the 5'-adapter and the 3'-adapter comprise the same type of tag or probe.

The methods, compositions, and kits disclosed herein can further comprise one or more adapters further comprising a linker sequence. A non-limiting list of linker sequences includes homopolynucleotide sequences such as $(A)_{40}$ or repeats such as $(ACA)_{15}$. The 5'-adapter can further comprise one or more linker sequences. Alternatively, or additionally, the 3'-adapter further comprises one or more linker sequences. In some instances, the 5'-adapter and the 3'-adapter further comprise one or more linker sequences. In some instances, the 5'-adapter and the 3'-adapter comprise different linker sequences. In other instances, the 5'-adapter and the 3'-adapter comprise the same type of linker sequence.

The haptens, signal moieties, tags, probes, and/or linker sequences disclosed herein can be located at the 5' end of an adapter. For example, the haptens, signal moieties, tags, probes, and/or linker sequences disclosed herein are located at the 5' end of a 5'-adapter. In another example, haptens, signal moieties, tags, probes, and/or linker sequences disclosed herein are located at the 5' end of a 3'-adapter. Alternatively, or additionally, the haptens, signal moieties, tags, probes, and/or linker sequences disclosed herein are located at the 3' end of an adapter. For example, the haptens, signal moieties, tags, probes, and/or linker sequences disclosed herein are located at the 3' end of a 5'-adapter. In another example, haptens, signal moieties, tags, probes, and/or linker sequences disclosed herein are located at the 3' end of a 3'-adapter. In some instances, the haptens, signal moieties, tags, probes, and/or linker sequences disclosed herein are located between the 5' end and the 3' end of an adapter. For example, the haptens, signal moieties, tags, probes, and/or linker sequences disclosed herein are located between the 5' end and the 3' end of a 5'-adapter. In another example, the haptens, signal moieties, tags, probes, and/or linker sequences disclosed herein are located between the 5' end and the 3' end of a 3'-adapter.

The haptens, signal moieties, tags, probes, and/or linker sequences disclosed herein can be located within the sequence of an adapter. For example, the sequence at the 5' end of a 3'-adapter can comprise a linker sequence. In another example, the sequence at the 3' end of a 5'-adapter can comprise a probe sequence. In another example, the sequence in between the 3' end and the 5' end of an adapter sequence can comprise a linker sequence.

The haptens, signal moieties, tags, probes, and/or linker sequences disclosed herein can be attached to an adapter. For example, a hapten can be attached to the 5' end of a 3'-adapter. In another example, a signal moiety can be attached to the 3' end of a 5'-adapter. In another example, tag can be attached to the region between the 3' end and the 5' end of an adapter sequence.

V. Ligation to Target RNAs

The methods, compositions and kits disclosed herein can comprise attachment of one or more adapters to one or both ends of a target RNA or derivative thereof. In some instances, methods, compositions and kits disclosed herein can comprise attachment of one or more adapters to one or both ends of a target RNA hybridized to a TSO (e.g., TSO-hybridized target RNA). In some instances, attachment of the one or more adapters to the target RNA or derivative thereof comprises conducting one or more ligation reactions. Conducting one or more ligation reactions can comprise ligating one or more adapters to the TSO-hybridized target RNA.

Figure 6:
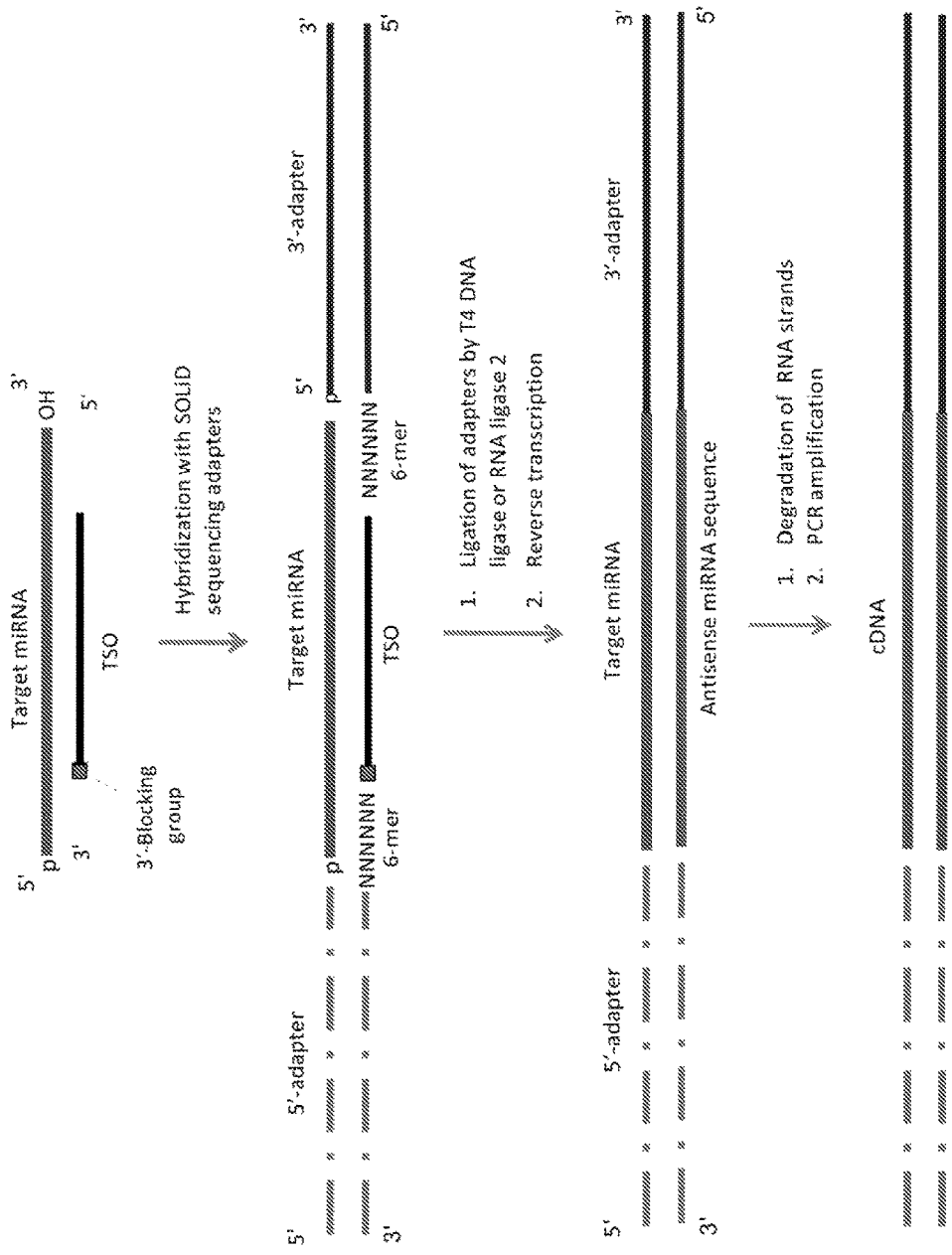
FIG. 6. Scheme of construction of a SOLiD- or ION Torrent-like "miRNA library" comprising hybridization of target miRNAs with TSO; simultaneous ligation of adapters to both ends of miRNAs; and reverse transcription in solution. This scheme can be applied to the construction of small RNA libraries for SOLiD and Ion Torrent sequencing platforms.

In some embodiments of this invention, the ligation reactions are template- or splint-independent (e.g., do not rely on simultaneous hybridization target RNA and adapter to a probe having both target and adapter-binding segments such as is described in U.S. Pat. No. 8,278,035). The TSOs disclosed herein can hybridize only to target RNAs and cannot hybridize to adapters. In some embodiments, the ligation reaction is template-dependent. An example of a template-dependent ligation reaction is ligation of the SOLiD-type adapters, as shown in FIG. 6. In some instances, the adapters hybridize to the TSO-hybridized target RNA.

Conducting one or more ligation reactions can comprise the use of one or more ligases. In some instances, the one or more ligases comprise a T4 RNA ligase or T4 DNA ligase. In some instances, the one or more ligases are selected from a group comprising T4 RNA ligase 1 (Rnl 1), T4 RNA ligase 2 (Rnl2), and a T4 RNA ligase 2 derivative. In some instances, the T4 RNA ligase 2 derivative comprises T4 RNA ligase 2 (1-249) truncated form or T4 RNA ligase 2 (1-249) truncated form with point mutation K227Q.

In some instances, conducting one or more ligation reactions comprise the use of less than about five ligases. In other instances, conducting one or more ligation reactions comprise the use of less than about four different ligases. Alternatively, conducting one or more ligation reactions comprise the use of less than about three different ligases. Conducting one or more ligation reactions comprise the use of less than about two different ligases.

In some instances, conducting one or more ligation reactions comprise the use of at least about one ligase. In other instances, conducting one or more ligation reactions comprise the use of at least about two different ligases. Alternatively, conducting one or more ligation reactions comprise the use of at least about three different ligases. Conducting one or more ligation reactions comprise the use of at least about four different ligases. For example, conducting one or more ligation reactions comprise (a) conducting a first ligation reaction comprising the use of Rnl2 or a derivative thereof in the absence of ATP to ligate a 3'-adapter in the 5'-adenylated (5'-App) form to the 3' end of a TSO-hybridized target RNA; and (b) conducting a second ligation reaction comprising the use of Rnl1 in the presence of ATP to ligate a 5'-adapter to the 5' end of the TSO-hybridized target RNA.

Conducting one or more ligation reactions can comprise the use of one or more ligases in the presence and/or absence of ATP. For example, conducting a ligation reaction comprises the use of Rnl1 in the absence of ATP to ligate a 3'-adapter in the 5'-adenylated (5'-App) form to the 3' end of a TSO-hybridized target RNA. In another example, conducting a ligation reaction comprises the use of Rnl1 in the presence of ATP to ligate a 5'-adapter to the 5' end of a TSO-hybridized target RNA.

In some instances, conducting one or more ligation reactions comprise the use of Rnl1. Conducting one or more ligation reactions can comprise the use of Rnl1 in the absence of ATP to ligate a 3'-adapter in 5'-adenylated (5'-App) form to the 3' end of a TSO-hybridized target RNA. Alternatively, or additionally, conducting one or more ligation reactions can comprise the use of Rnl1 in the presence of ATP to ligate a 3'-adapter to the 3' end of a TSO-hybridized target RNA.

In other instances, conducting one or more ligation reactions comprises the use of Rnl2 For example, conducting one or more ligation reactions comprises the use of Rnl2 in the absence of ATP to ligate a 3'-adapter in 5'-adenylated (5'-App) form to the 3' end of a TSO-hybridized target RNA. In another example, conducting one or more ligation reactions comprise the use of Rnl2 in the presence of ATP to ligate a 3'-adapter in 5'-adenylated (5'-App) form to the 3' end of a TSO-hybridized target RNA.

Alternatively, or additionally, conducting one or more ligation reactions comprises the use of an Rnl2 derivative. For example, conducting one or more ligation reactions comprises the use of Rnl2 derivative in the absence of ATP to ligate a 3'-adapter in 5'-adenylated (5'-App) form to the 3' end of a TSO-hybridized target RNA. In another example, conducting one or more ligation reactions comprise the use of Rnl2 derivative in the presence of ATP to ligate a 3'-adapter in 5'-adenylated (5'-App) form to the 3' end of a TSO-hybridized target RNA.

Further disclosed herein, are methods, compositions, and kits for improving ligation efficiency comprising (a) hybridizing one or more TSOs to one or more target RNAs to produce a TSO-hybridized target RNA; and (b) attaching one or more adapters to the target RNA portion of the TSO-hybridized target RNA to produce an adapter-ligated target RNA, wherein ligation efficiency is dependent upon the hybridization of the one or more TSOs to the one or more target RNAs.

Ligation efficiency can refer to the efficiency by which a nucleotide (e.g., adapter, linker) is ligated to a target (e.g., target RNA or product thereof). In some instances, ligation efficiency refers to the efficiency by which an adapter is ligated to the RNA portion of a TSO-hybridized target RNA. Ligation efficiency can refer to the efficiency by which a second adapter is ligated to a second end of the RNA portion of a TSO-hybridized target RNA. In other instances, ligation efficiency refers to the efficiency by which a linker is ligated to a TSO-hybridized target RNA. Alternatively, or additionally, ligation efficiency refers to the efficiency by which a linker is ligated to the adapter portion of an adapter-ligated target RNA. An increase in ligation efficiency can refer to an increase in the number of TSO-hybridized target RNA that are ligated to one or more adapters. In other instances, an increase in ligation efficiency can refer to an increase in the number of adapter-ligated target RNA that are ligated to one or more linkers. In some instances, buffers, reagents, ligases, and/or other components of a ligation reaction directly or indirectly effect ligation efficiency. In some instances, the methods, compositions, and kits disclosed herein increase a ligation efficiency. In other instances, the methods, compositions, and kits disclosed herein increase the ligation efficiency of a ligase. In some instances, ligation efficiency is increased with the addition of a TSO to the ligation reaction.

In other instances, ligation efficiency is increased by pre-hybridization of a TSO to a target RNA. In some instances, hybridization of the TSO to a target RNA reduces and/or prevents the formation of one or more secondary structures in the target RNA or product thereof. In some instances, reduction and/or prevention of the formation of one or more secondary structures in the target RNA or product thereof increases the ligation efficiency.

In some instances, hybridization of the TSO to the target RNA prior to attachment of the adapter to the target RNA improves and/or increases ligation efficiency of the adapter to the target RNA by at least about 10%, 20%, 30%, 40%, 45%, 50%, 55%, 60% or more as compared to attachment of the adapter to a target RNA without pre-hybridization with a TSO. In other instances, hybridization of the TSO to the target RNA prior to attachment of the adapter to the target RNA improves and/or increases ligation efficiency of the adapter to the target RNA by at least about 65% as compared to attachment of the adapter to a target RNA without pre-hybridization with a TSO. Alternatively, hybridization of the TSO to the target RNA prior to attachment of the adapter to the target RNA improves and/or increases ligation efficiency of the adapter to the target RNA by at least about 70% as compared to attachment of the adapter to a target RNA without pre-hybridization with a TSO. Hybridization of the TSO to the target RNA prior to attachment of the adapter to the target RNA can improve and/or increaseligation efficiency of the adapter to the target RNA by at least about 75% as compared to attachment of the adapter to a target RNA without pre-hybridization with a TSO. In some instances, hybridization of the TSO to the target RNA prior to attachment of the adapter to the target RNA improves and/or increases ligation efficiency of the adapter to the target RNA by at least about 80% as compared to attachment of the adapter to a target RNA without pre-hybridization with a TSO. In other instances, hybridization of the TSO to the target RNA prior to attachment of the adapter to the target RNA improves and/or increases ligation efficiency of the adapter to the target RNA by at least about 85% as compared to attachment of the adapter to a target RNA without pre-hybridization with a TSO. Alternatively, hybridization of the TSO to the target RNA prior to attachment of the adapter to the target RNA improves and/or increases ligation efficiency of the adapter to the target RNA by at least about 90% as compared to attachment of the adapter to a target RNA without pre-hybridization with a TSO. Hybridization of the TSO to the target RNA prior to attachment of the adapter to the target RNA can improve and/or increase-ligation efficiency of the adapter to the target RNA by at least about 95% as compared to attachment of the adapter to a target RNA without pre-hybridization with a TSO.

In some instances, hybridization of the TSO to the target RNA prior to attachment of the adapter to the target RNA improves and/or increases ligation efficiency of the adapter to the target RNA by at least about 2, 3, 5, 10, 15, 20, 30, 40, 50, 60, 70, 80, 90, 100-fold or more as compared to attachment of the adapter to a target RNA without pre-hybridization with a TSO. In some instances, hybridization of the TSO to the target RNA prior to attachment of the adapter to the target RNA improves and/or increases ligation efficiency of the adapter to the target RNA by at least about 200, 300, 400, 500, 600, 700, 800, 900, 1000, 1500, 2000, 3000, 4000, 5000, 6000, 7000, 8000, 9000, 10000-fold or more as compared to attachment of the adapter to a target RNA without pre-hybridization with a TSO. In other instances, hybridization of the TSO to the target RNA prior to attachment of the adapter to the target RNA improves and/or increases ligation efficiency of the adapter to the target RNA by at least about 10-fold as compared to attachment of the adapter to a target RNA without pre-hybridization with a TSO. Alternatively, hybridization of the TSO to the target RNA prior to attachment of the adapter to the target RNA improves and/or increases ligation efficiency of the adapter to the target RNA by at least about 100-fold as compared to attachment of the adapter to a target RNA without pre-hybridization with a TSO. Hybridization of the TSO to the target RNA prior to attachment of the adapter to the target RNA can improve and/or increaseligation efficiency of the adapter to the target RNA by at least about 200-fold as compared to attachment of the adapter to a target RNA without pre-hybridization with a TSO. In some instances, hybridization of the TSO to the target RNA prior to attachment of the adapter to the target RNA improves and/or increases ligation efficiency of the adapter to the target RNA by at least about 300-fold as compared to attachment of the adapter to a target RNA without pre-hybridization with a TSO. In other instances, hybridization of the TSO to the target RNA prior to attachment of the adapter to the target RNA improves and/or increases ligation efficiency of the adapter to the target RNA by at least about 400-fold as compared to attachment of the adapter to a target RNA without pre-hybridization with a TSO. Alternatively, hybridization of the TSO to the target RNA prior to attachment of the adapter to the target RNA improves and/or increases ligation efficiency of the adapter to the target RNA by at least about 500-fold as compared to attachment of the adapter to a target RNA without pre-hybridization with a TSO. Hybridization of the TSO to the target RNA prior to attachment of the adapter to the target RNA can improve and/or increaseligation efficiency of the adapter to the target RNA by at least about 600-fold as compared to attachment of the adapter to a target RNA without pre-hybridization with a TSO. In other instances, hybridization of the TSO to the target RNA prior to attachment of the adapter to the target RNA improves and/or increases ligation efficiency of the adapter to the target RNA by at least about 700-fold as compared to attachment of the adapter to a target RNA without pre-hybridization with a TSO. Alternatively, hybridization of the TSO to the target RNA prior to attachment of the adapter to the target RNA improves and/or increases ligation efficiency of the adapter to the target RNA by at least about 800-fold as compared to attachment of the adapter to a target RNA without pre-hybridization with a TSO. Hybridization of the TSO to the target RNA prior to attachment of the adapter to the target RNA can improve and/or increase-ligation efficiency of the adapter to the target RNA by at least about 900-fold as compared to attachment of the adapter to a target RNA without pre-hybridization with a TSO. In other instances, hybridization of the TSO to the target RNA prior to attachment of the adapter to the target RNA improves and/or increases ligation efficiency of the adapter to the target RNA by at least about 1000-fold as compared to attachment of the adapter to a target RNA without pre-hybridization with a TSO. Alternatively, hybridization of the TSO to the target RNA prior to attachment of the adapter to the target RNA improves and/or increases ligation efficiency of the adapter to the target RNA by at least about 1500-fold as compared to attachment of the adapter to a target RNA without pre-hybridization with a TSO. Hybridization of the TSO to the target RNA prior to attachment of the adapter to the target RNA can improve and/or increaseligation efficiency of the adapter to the target RNA by at least about 2000-fold as compared to attachment of the adapter to a target RNA without pre-hybridization with a TSO.

Further disclosed herein, are methods, compositions, and kits for reducing and/or preventing ligation bias comprising (a) hybridizing one or more TSOs to one or more target RNAs to produce a TSO-hybridized target RNA; and (b) attaching one or more adapters to the target RNA portion of the TSO-hybridized target RNA to produce an adapter-ligated target RNA, wherein attachment of the one or more adapters to the target RNA is significantly independent of ligation bias. In some instances, attachment of the one or more adapters to the RNA portion of the TSO-hybridized target RNA is dependent upon the hybridization of the one or more TSOs to the one or more target RNAs.

In some instances, ligation bias refers to the bias by which a nucleotide (e.g., adapter, linker) is ligated to a target (e.g., target RNA or product thereof). In some instances, ligation bias refers to the preferential ligation of a nucleotide to one or more copies of a target RNA or a product thereof over the ligation of the nucleotide to one more copies of another target RNA. Alternatively, ligation bias refers to the disproportionate ligation of one or more nucleotides to one or more target RNAs. In some instances, the number of ligated target RNAs is not an accurate reflection of the actual number of target RNAs in the sample. For example, a sample comprises similar or equal number of copies of target RNA A and target RNA B, however, after conducting a ligation reaction, there are a substantially greater number (e.g., 2-fold or more, at least about 10% or more) of adapter-ligated target RNA A in the sample than adapter-ligated target RNA B. A decrease in ligation bias can refer to a decrease in the disproportionate ligation of one or more nucleotides to one or more targets. In some instances, the methods, compositions, and kits disclosed herein decrease a ligation bias. In other instances, the methods, compositions, and kits disclosed herein decrease a ligation bias of a ligase. In some instances, ligation bias is decreased with the addition of a TSO to the ligation reaction. In other instances, ligation bias is decreased by pre-hybridization of a TSO to a target RNA. In some instances, hybridization of the TSO to a target RNA reduces and/or prevents the formation of one or more secondary structures in the target RNA or product thereof. In some instances, reduction and/or prevention of the formation of one or more secondary structures in the target RNA or product thereof decreases the ligation bias.

In some instances, hybridization of the TSO to the target RNA prior to attachment of the adapter to the target RNA reduces and/or prevents ligation bias of the adapter to the target RNA by at least about 10%, 20%, 30%, 40%, 45%, 50%, 55%, 60% or more as compared to attachment of the adapter to a target RNA without pre-hybridization with a TSO. In other instances, hybridization of the TSO to the target RNA prior to attachment of the adapter to the target RNA reduces and/or prevents ligation bias of the adapter to the target RNA by at least about 65% as compared to attachment of the adapter to a target RNA without pre-hybridization with a TSO. Alternatively, hybridization of the TSO to the target RNA prior to attachment of the adapter to the target RNA reduces and/or prevents ligation bias of the adapter to the target RNA by at least about 70% as compared to attachment of the adapter to a target RNA without pre-hybridization with a TSO. Hybridization of the TSO to the target RNA prior to attachment of the adapter to the target RNA can reduce and/or prevent ligation bias of the adapter to the target RNA by at least about 75% as compared to attachment of the adapter to a target RNA without pre-hybridization with a TSO. In some instances, hybridization of the TSO to the target RNA prior to attachment of the adapter to the target RNA reduces and/or prevents ligation bias of the adapter to the target RNA by at least about 80% as compared to attachment of the adapter to a target RNA without pre-hybridization with a TSO. In other instances, hybridization of the TSO to the target RNA prior to attachment of the adapter to the target RNA reduces and/or prevents ligation bias of the adapter to the target RNA by at least about 85% as compared to attachment of the adapter to a target RNA without pre-hybridization with a TSO. Alternatively, hybridization of the TSO to the target RNA prior to attachment of the adapter to the target RNA reduces and/or prevents ligation bias of the adapter to the target RNA by at least about 90% as compared to attachment of the adapter to a target RNA without pre-hybridization with a TSO. Hybridization of the TSO to the target RNA prior to attachment of the adapter to the target RNA can reduce ligation bias of the adapter to the target RNA by at least about 95% as compared to attachment of the adapter to a target RNA without pre-hybridization with a TSO.

In some instances, hybridization of the TSO to the target RNA prior to attachment of the adapter to the target RNA reduces and/or prevents ligation bias of the adapter to the target RNA by at least about 2, 3, 5, 10, 15, 20, 30, 40, 50, 60, 70, 80, 90, 100-fold or more as compared to attachment of the adapter to a target RNA without pre-hybridization with a TSO. In some instances, hybridization of the TSO to the target RNA prior to attachment of the adapter to the target RNA reduces and/or prevents ligation bias of the adapter to the target RNA by at least about 200, 300, 400, 500, 600, 700, 800, 900, 1000, 1500, 2000, 3000, 4000, 5000, 6000, 7000, 8000, 9000, 10000-fold or more as compared to attachment of the adapter to a target RNA without pre-hybridization with a TSO. In other instances, hybridization of the TSO to the target RNA prior to attachment of the adapter to the target RNA reduces and/or prevents ligation bias of the adapter to the target RNA by at least about 10-fold as compared to attachment of the adapter to a target RNA without pre-hybridization with a TSO. Alternatively, hybridization of the TSO to the target RNA prior to attachment of the adapter to the target RNA reduces and/or prevents ligation bias of the adapter to the target RNA by at least about 100-fold as compared to attachment of the adapter to a target RNA without pre-hybridization with a TSO. Hybridization of the TSO to the target RNA prior to attachment of the adapter to the target RNA can reduce and/or prevent ligation bias of the adapter to the target RNA by at least about 200-fold as compared to attachment of the adapter to a target RNA without pre-hybridization with a TSO. In some instances, hybridization of the TSO to the target RNA prior to attachment of the adapter to the target RNA reduces and/or prevents ligation bias of the adapter to the target RNA by at least about 300-fold as compared to attachment of the adapter to a target RNA without pre-hybridization with a TSO. In other instances, hybridization of the TSO to the target RNA prior to attachment of the adapter to the target RNA reduces and/or prevents ligation bias of the adapter to the target RNA by at least about 400-fold as compared to attachment of the adapter to a target RNA without pre-hybridization with a TSO. Alternatively, hybridization of the TSO to the target RNA prior to attachment of the adapter to the target RNA reduces and/or prevents ligation bias of the adapter to the target RNA by at least about 500-fold as compared to attachment of the adapter to a target RNA without pre-hybridization with a TSO. Hybridization of the TSO to the target RNA prior to attachment of the adapter to the target RNA can reduce and/or prevent ligation bias of the adapter to the target RNA by at least about 600-fold as compared to attachment of the adapter to a target RNA without pre-hybridization with a TSO. In other instances, hybridization of the TSO to the target RNA prior to attachment of the adapter to the target RNA reduces and/or prevents ligation bias of the adapter to the target RNA by at least about 700-fold as compared to attachment of the adapter to a target RNA without pre-hybridization with a TSO. Alternatively, hybridization of the TSO to the target RNA prior to attachment of the adapter to the target RNA reduces and/or prevents ligation bias of the adapter to the target RNA by at least about 800-fold as compared to attachment of the adapter to a target RNA without pre-hybridization with a TSO. Hybridization of the TSO to the target RNA prior to attachment of the adapter to the target RNA can reduce and/or prevent ligation bias of the adapter to the target RNA by at least about 900-fold as compared to attachment of the adapter to a target RNA without pre-hybridization with a TSO. In other instances, hybridization of the TSO to the target RNA prior to attachment of the adapter to the target RNA reduces and/or prevents ligation bias of the adapter to the target RNA by at least about 1000-fold as compared to attachment of the adapter to a target RNA without pre-hybridization with a TSO. Alternatively, hybridization of the TSO to the target RNA prior to attachment of the adapter to the target RNA reduces and/or prevents ligation bias of the adapter to the target RNA by at least about 1500-fold as compared to attachment of the adapter to a target RNA without pre-hybridization with a TSO. Hybridization of the TSO to the target RNA prior to attachment of the adapter to the target RNA can reduce and/or prevent ligation bias of the adapter to the target RNA by at least about 2000-fold as compared to attachment of the adapter to a target RNA without pre-hybridization with a TSO.

In some instances, attachment of the one or more adapters comprises (a) attachment of a first adapter; and (b) attachment of a second adapter. In some instances, hybridization of the TSO to the target RNA improves and/or increases attachment of the first adapter to the target RNA. Improvement of the attachment of the first adapter to the target RNA can refer to increasing the efficiency of ligation of the first adapter to the target RNA. Alternatively, improving the attachment of the first adapter to the target RNA comprises enhancing the ability of the first adapter to attach to the target RNA. In other instances, improving the attachment of the first adapter to the target RNA refers to the increase in the number of target RNAs attached to the first adapter. In some instances, attachment of the first adapter is improved and/or increased by at least about 10%, 20%, 30%, 40%, 50% or more as compared to attachment of the first adapter to a target RNA without a TSO. In other instances, attachment of the first adapter is improved and/or increased by at least about 60% as compared to attachment of the first adapter to a target RNA without a TSO. Alternatively, attachment of the first adapter is improved and/or increased by at least about 70% as compared to attachment of the first adapter to a target RNA without a TSO. Attachment of the first adapter can improve and/or increase by at least about 75% as compared to attachment of the first adapter to a target RNA without a TSO. In some instances, attachment of the first adapter is improved and/or increased by at least about 80% as compared to attachment of the first adapter to a target RNA without a TSO. In other instances, attachment of the first adapter is improved and/or increased by at least about 85% as compared to attachment of the first adapter to a target RNA without a TSO. Alternatively, attachment of the first adapter is improved and/or increased by at least about 90% as compared to attachment of the first adapter to a target RNA without a TSO. Attachment of the first adapter can improve and/or increase by at least about 95% as compared to attachment of the first adapter to a target RNA without a TSO.

In some instances, hybridization of the TSO to the target RNA improves and/or increases attachment of the second adapter to the target RNA. Improvement of the attachment of the second adapter to the target RNA can refer to increasing the efficiency of ligation of the second adapter to the target RNA. Alternatively, improving the attachment of the second adapter to the target RNA comprises enhancing the ability of the second adapter to attach to the target RNA. In other instances, improving the attachment of the second adapter to the target RNA refers to the increase in the number of target RNAs attached to the second adapter. In some instances, attachment of the second adapter is improved and/or increased by at least about 10%, 20%, 30%, 40%, 50% or more as compared to attachment of the second adapter to a target RNA without a TSO. In other instances, attachment of the second adapter is improved and/or increased by at least about 60% as compared to attachment of the second adapter to a target RNA without a TSO. Alternatively, attachment of the second adapter is improved and/or increased by at least about 70% as compared to attachment of the second adapter to a target RNA without a TSO. Attachment of the second adapter can improve and/or increase by at least about 75% as compared to attachment of the second adapter to a target RNA without a TSO. In some instances, attachment of the second adapter is improved and/or increased by at least about 80% as compared to attachment of the second adapter to a target RNA without a TSO. In other instances, attachment of the second adapter is improved and/or increased by at least about 85% as compared to attachment of the second adapter to a target RNA without a TSO. Alternatively, attachment of the second adapter is improved and/or increased by at least about 90% as compared to attachment of the second adapter to a target RNA without a TSO. Attachment of the second adapter is improved and/or increased by at least about 95% as compared to attachment of the second adapter to a target RNA without a TSO.

The methods, compositions and kits can further comprise reducing and/or inhibiting adapter ligation to non-target RNAs. In some instances, adapter ligation to non-target RNAs is reduced and/or inhibited by at least about 10%, 20%, 30%, 40%, 50% or more as compared to a ligation reaction without a TSO. In other instances, adapter ligation to the non-target RNAs is reduced and/or inhibited by at least about 55% as compared to a ligation reaction without a TSO. Alternatively, adapter ligation to the non-target RNAs is reduced and/or inhibited by at least about 60% as compared to a ligation reaction without a TSO. Adapter ligation to the non-target RNAs can be reduced and/or inhibited by at least about 65% as compared to a ligation reaction without a TSO. In some instances, adapter ligation to the non-target RNAs is reduced and/or inhibited by at least about 70% as compared to a ligation reaction without a TSO. In other instances, adapter ligation to the non-target RNAs is reduced and/or inhibited by at least about 75% as compared to a ligation reaction without a TSO. Alternatively, adapter ligation to the non-target RNAs is reduced and/or inhibited by at least about 80% as compared to a ligation reaction without a TSO. Adapter ligation to the non-target RNAs can be reduced and/or inhibited by at least about 85% as compared to a ligation reaction without a TSO. In some instances, adapter ligation to the non-target RNAs is reduced and/or inhibited by at least about 90% as compared to a ligation reaction without a TSO. In other instances, adapter ligation to the non-target RNAs is reduced and/or inhibited by at least about 95% as compared to a ligation reaction without a TSO. Alternatively, adapter ligation to the non-target RNAs is reduced and/or inhibited by at least about 97% as compared to a ligation reaction without a TSO. Adapter ligation to the non-target RNAs can be reduced and/or inhibited by about 100% as compared to a ligation reaction without a TSO.

In some instances, adapter ligation to the non-target RNAs is reduced and/or inhibited by at least about 2, 3, 4, 5, 10, 15, 20, 25, 30, 40, 50, 60, 70, 80, 90, or 100-fold or more as compared to a ligation reaction without a TSO. In other instances, adapter ligation to the non-target RNAs is reduced and/or inhibited by at least about 200, 300, 400, 500, 600, 700, 800, 900, or 1000-fold or more as compared to a ligation reaction without a TSO. Alternatively, adapter ligation to the non-target RNAs is reduced and/or inhibited by at least about 1100, 1200, 1300, 1400, 1500, 2000, 2500, 3000, 3500, 4000, 4500, 5000, 5500, 6000, 6500, 7000, 7500, 8000, 8500, 9000, 9500, or 10000-fold or more as compared to a ligation reaction without a TSO.

VI. Amplification of Target RNAs

The methods, compositions and kits as disclosed herein can further comprise amplification of at least a portion of a target RNA or target RNA-specific sequence, or derivatives thereof, to produce an amplified target RNA. The methods, compositions and kits as disclosed herein can further comprise amplification of at least a portion of a target RNA or target RNA-specific sequence, or derivatives thereof, to produce an amplified target cRNA. In some instances, a target RNA-specific sequence comprises a sequence that is identical or complementary to a target RNA sequence. In some instances, a derivative of a target RNA comprises an adapter-ligated target RNA. Additional examples of target RNA derivatives include, but are not limited to, isolated target RNA, hapten-adapter-ligated target RNA, probe-adapter-ligated target RNA, or label-adapter-ligated target RNA. In some instances, amplification of the target RNA or derivative thereof comprises conducting a reaction to amplify at least a portion of an adapter-ligated target RNA. In some instances, the amplified target RNA-specific sequences are used for cloning into conventional sequencing vectors or for direct analysis by next-generation sequencing methods. In other instances, the amplified target RNA-specific sequences are used for further amplification and detection of the target RNA-specific sequences by PCR-based methods. In some other instances, the amplified target RNA-specific sequences are used for detection of the amplified sequences by other methods such as probe arrays.

Amplification of at least a portion of a target RNA or target RNA-specific sequence, or derivatives thereof can comprise amplifying the target RNA or a portion thereof. In some instances, amplification of at least a portion of a target RNA or target RNA-specific sequence, or derivatives thereof comprises amplifying the TSO or a portion thereof. In other instances, amplification of at least a portion of a target RNA or target RNA-specific sequence, or derivatives thereof comprises amplifying the adapter or a portion thereof. Alternatively, amplification of at least a portion of a target RNA or target RNA-specific sequence, or derivatives thereof comprises amplifying the linker or a portion thereof. Amplification of at least a portion of a target RNA or target RNA-specific sequence, or derivatives thereof can comprise amplifying a copy of the target RNA.

Amplification of the target RNA or derivative thereof can comprise PCR-based methods. Examples of PCR-based methods include, but are not limited to, RT-PCR, end-point PCR, real-time qPCR, HD-PCR, Next Generation PCR, digital PCR, or any combination thereof. Additional PCR methods include, but are not limited to, droplet PCR, emulsion PCR, overlap extension PCR (OE-PCR), inverse PCR, linear-after-the-exponential (LATE)-PCR, long PCR, Mega-Plex PCR, nested PCR, and touchdown PCR.

Alternatively, amplification of the target RNA or derivative thereof comprises non-PCR-based methods. Examples of non-PCR based methods include, but are not limited to, multiple displacement amplification (MDA), transcription-mediated amplification (TMA), nucleic acid sequence-based amplification (NASBA), strand displacement amplification (SDA), real-time SDA, rolling circle amplification (RCA), hyperbranched RCA (HRCA) or circle-to-circle amplification.

In some instances, amplification of the target RNA or derivative thereof comprises (a) circularizing the target RNA or derivative thereof to produce a circularized target RNA; and (b) conducting a reaction to amplify the circularized target RNA-specific sequences. Conducting a reaction to amplify the circularized target RNA-specific sequences can comprise any of the amplification methods disclosed herein.

In other instances, amplification of the target RNA or derivative thereof comprises (a) conducting a reaction to reverse transcribe the target RNA or derivative thereof to produce a cRNA, wherein the cRNA is a DNA copy of the target RNA or derivative thereof; and (b) conducting a reaction to amplify the cRNA.

Further disclosed herein, are methods, compositions, and kits for improving amplification efficiency comprising (a) hybridizing one or more TSOs to one or more target RNAs to produce a TSO-hybridized target RNA; and (b) amplifying at least a portion of the TSO-hybridized target RNA to produce an amplified target RNA, wherein amplification efficiency is dependent upon the hybridization of the one or more TSOs to the one or more target RNAs.

Amplification efficiency can refer to the efficiency by which a target RNA, portion thereof, or product thereof is amplified. In some instances, amplification efficiency refers to the efficiency by which at least a portion of a TSO-hybridized target RNA is amplified. Amplification efficiency can refer to the efficiency by which at least a portion of an adapter-ligated target RNA is amplified. In other instances, amplification efficiency refers to the efficiency by which at least a portion of a linker-target RNA is amplified. An increase in amplification efficiency can refer to an increase in the number of TSO-hybridized target RNA that are amplified. In other instances, an increase in amplification efficiency can refer to an increase in the number of adapter-ligated target RNA that are amplified. In some instances, buffers, reagents, polymerases, and/or other components of an amplification reaction directly or indirectly effect amplification efficiency. In some instances, the methods, compositions, and kits disclosed herein increase an amplification efficiency. In other instances, the methods, compositions, and kits disclosed herein increase the amplification efficiency of a polymerase. In some instances, amplification efficiency is increased with the addition of a TSO to the amplification reaction. In other instances, amplification efficiency is increased by pre-hybridization of a TSO to a target RNA. In some instances, hybridization of the TSO to a target RNA reduces and/or prevents the formation of one or more secondary structures in the target RNA or product thereof. In some instances, reduction and/or prevention of the formation of one or more secondary structures in the target RNA or product thereof increases the amplification efficiency.

In some instances, hybridization of the TSO to the target RNA prior to amplification of the target RNA improves amplification efficiency of the target RNA by at least about 10%, 20%, 30%, 40%, 45%, 50%, 55%, 60% or more as compared to amplification of a target RNA without pre-hybridization with a TSO. In other instances, hybridization of the TSO to the target RNA prior to amplification of the target RNA improves amplification of the target RNA by at least about 65% as compared to amplification of a target RNA without pre-hybridization with a TSO. Alternatively, hybridization of the TSO to the target RNA prior to amplification of the target RNA improves amplification of the target RNA by at least about 70% as compared to amplification of a target RNA without pre-hybridization with a TSO. Hybridization of the TSO to the target RNA prior to amplification of the target RNA can improve amplification of the target RNA by at least about 75% as compared to amplification of a target RNA without pre-hybridization with a TSO. In some instances, hybridization of the TSO to the target RNA prior to amplification of the target RNA improves amplification of the target RNA by at least about 80% as compared to amplification of a target RNA without pre-hybridization with a TSO. In other instances, hybridization of the TSO to the target RNA prior to amplification of the target RNA improves amplification of the target RNA by at least about 85% as compared to amplification of a target RNA without pre-hybridization with a TSO. Alternatively, hybridization of the TSO to the target RNA prior to amplification of the target RNA improves amplification of the target RNA by at least about 90% as compared to amplification of a target RNA without pre-hybridization with a TSO. Hybridization of the TSO to the target RNA prior to amplification of the target RNA can improve amplification of the target RNA by at least about 95% as compared to amplification of a target RNA without pre-hybridization with a TSO.

In some instances, hybridization of the TSO to the target RNA prior to amplification of the target RNA improves and/or increases amplification efficiency of the at least a portion of a target RNA or product thereof by at least about 2, 3, 5, 10, 15, 20, 30, 40, 50, 60, 70, 80, 90, 100-fold or more as compared to amplification of a target RNA without pre-hybridization with a TSO. In some instances, hybridization of the TSO to the target RNA prior to amplification of the target RNA improves and/or increases amplification efficiency of the at least a portion of a target RNA or product thereof by at least about 200, 300, 400, 500, 600, 700, 800, 900, 1000, 1500, 2000, 3000, 4000, 5000, 6000, 7000, 8000, 9000, 10000-fold or more as compared to amplification of a target RNA without pre-hybridization with a TSO. In other instances, hybridization of the TSO to the target RNA prior to amplification of the target RNA improves and/or increases amplification efficiency of the adapter to the target RNA by at least about 10-fold as compared to amplification of a target RNA without pre-hybridization with a TSO. Alternatively, hybridization of the TSO to the target RNA prior to amplification of the target RNA improves and/or increases amplification efficiency of the adapter to the target RNA by at least about 100-fold as compared to amplification of a target RNA without pre-hybridization with a TSO. Hybridization of the TSO to the target RNA prior to amplification of the target RNA can improve and/or increase amplification efficiency of the adapter to the target RNA by at least about 200-fold as compared to amplification of a target RNA without pre-hybridization with a TSO. In some instances, hybridization of the TSO to the target RNA prior to amplification of the target RNA improves and/or increases amplification efficiency of the adapter to the target RNA by at least about 300-fold as compared to amplification of a target RNA without pre-hybridization with a TSO. In other instances, hybridization of the TSO to the target RNA prior to amplification of the target RNA improves and/or increases amplification efficiency of the adapter to the target RNA by at least about 400-fold as compared to amplification of a target RNA without pre-hybridization with a TSO. Alternatively, hybridization of the TSO to the target RNA prior to amplification of the target RNA improves and/or increases amplification efficiency of the adapter to the target RNA by at least about 500-fold as compared to amplification of a target RNA without pre-hybridization with a TSO. Hybridization of the TSO to the target RNA prior to amplification of the target RNA can improve and/or increase amplification efficiency of the adapter to the target RNA by at least about 600-fold as compared to amplification of a target RNA without pre-hybridization with a TSO. In other instances, hybridization of the TSO to the target RNA prior to amplification of the target RNA improves and/or increases amplification efficiency of the adapter to the target RNA by at least about 700-fold as compared to amplification of a target RNA without pre-hybridization with a TSO. Alternatively, hybridization of the TSO to the target RNA prior to amplification of the target RNA improves and/or increases amplification efficiency of the adapter to the target RNA by at least about 800-fold as compared to amplification of a target RNA without pre-hybridization with a TSO. Hybridization of the TSO to the target RNA prior to amplification of the target RNA can improve and/or increase amplification efficiency of the adapter to the target RNA by at least about 900-fold as compared to amplification of a target RNA without pre-hybridization with a TSO. In other instances, hybridization of the TSO to the target RNA prior to amplification of the target RNA improves and/or increases amplification efficiency of the adapter to the target RNA by at least about 1000-fold as compared to amplification of a target RNA without pre-hybridization with a TSO. Alternatively, hybridization of the TSO to the target RNA prior to amplification of the target RNA improves and/or increases amplification efficiency of the adapter to the target RNA by at least about 1500-fold as compared to amplification of a target RNA without pre-hybridization with a TSO. Hybridization of the TSO to the target RNA prior to amplification of the target RNA can improve and/or increase amplification efficiency of the adapter to the target RNA by at least about 2000-fold as compared to amplification of a target RNA without pre-hybridization with a TSO.

Further disclosed herein, are methods, compositions, and kits for reducing and/or preventing amplification bias comprising (a) hybridizing one or more TSOs to one or more target RNAs to produce a TSO-hybridized target RNA; and (b) amplifying at least a portion of the TSO-hybridized target RNA to produce an amplified target RNA, wherein amplification of the target RNA is significantly independent of amplification bias. In some instances, amplification of at least a portion of the TSO-hybridized target RNA is dependent upon the hybridization of the one or more TSOs to the one or more target RNAs.

In some instances, amplification bias refers to the bias by which a target RNA, a portion thereof, or product thereof is amplified. In some instances, amplification bias refers to the preferential amplification of a target RNA, portion thereof or a product thereof over the amplification of another target RNA, portion thereof or a product thereof. Alternatively, amplification bias refers to the disproportionate amplification of one or more target RNAs. In some instances, the number of amplified target RNAs is not an accurate reflection of the actual number of target RNAs in the sample. For example, a sample comprises similar or equal number of copies of target RNA A and target RNA B, however, after conducting an amplification reaction, there are a substantially greater number (e.g., 2-fold or more, at least about 10% or more) of adapter-amplified target RNA A in the sample than adapter-amplified target RNA B. A decrease in amplification bias can refer to a decrease in the disproportionate amplification of one or more nucleotides to one or more targets. In some instances, the methods, compositions, and kits disclosed herein reduce and/or prevent an amplification bias. In other instances, the methods, compositions, and kits disclosed herein reduce and/or prevent an amplification bias of a polymerase. In some instances, amplification bias is reduced and/or prevented with the addition of a TSO to the amplification reaction. In other instances, amplification bias is reduced and/or prevented by pre-hybridization of a TSO to a target RNA. In some instances, hybridization of the TSO to a target RNA reduces and/or prevents the formation of one or more secondary structures in the target RNA or product thereof. In some instances, reduction and/or prevention of the formation of one or more secondary structures in the target RNA or product thereof reduces and/or prevents the amplification bias.

In some instances, hybridization of the TSO to the target RNA prior to amplification of the target RNA reduces and/or prevents amplification bias of the target RNA by at least about 10%, 20%, 30%, 40%, 45%, 50%, 55%, 60% or more as compared to amplification of a target RNA without pre-hybridization with a TSO. In other instances, hybridization of the TSO to the target RNA prior to amplification of the target RNA reduces and/or prevents amplification bias of the target RNA by at least about 65% as compared to amplification of a target RNA without pre-hybridization with a TSO. Alternatively, hybridization of the TSO to the target RNA prior to amplification of the target RNA reduces and/or prevents amplification bias of the target RNA by at least about 70% as compared to amplification of a target RNA without pre-hybridization with a TSO. Hybridization of the TSO to the target RNA prior to amplification of the target RNA can reduce and/or prevent amplification bias of the target RNA by at least about 75% as compared to amplification of a target RNA without pre-hybridization with a TSO. In some instances, hybridization of the TSO to the target RNA prior to amplification of the target RNA reduces and/or prevents amplification bias of the target RNA by at least about 80% as compared to amplification of a target RNA without pre-hybridization with a TSO. In other instances, hybridization of the TSO to the target RNA prior to amplification of the target RNA reduces and/or prevents amplification bias of the target RNA by at least about 85% as compared to amplification of a target RNA without pre-hybridization with a TSO. Alternatively, hybridization of the TSO to the target RNA prior to amplification of the target RNA reduces and/or prevents amplification bias of the target RNA by at least about 90% as compared to amplification of a target RNA without pre-hybridization with a TSO. Hybridization of the TSO to the target RNA prior to amplification of the target RNA can reduce and/or prevent amplification bias of the target RNA by at least about 95% as compared to amplification of a target RNA without pre-hybridization with a TSO.

In some instances, hybridization of the TSO to the target RNA prior to amplification of the target RNA reduces and/or prevents amplification bias of the target RNA by at least about 2, 3, 5, 10, 15, 20, 30, 40, 50, 60, 70, 80, 90, 100-fold or more as compared to amplification of a target RNA without pre-hybridization with a TSO. In some instances, hybridization of the TSO to the target RNA prior to amplification of the target RNA reduces and/or prevents amplification bias of the target RNA by at least about 200, 300, 400, 500, 600, 700, 800, 900, 1000, 1500, 2000, 3000, 4000, 5000, 6000, 7000, 8000, 9000, 10000-fold or more as compared to amplification of a target RNA without pre-hybridization with a TSO. In other instances, hybridization of the TSO to the target RNA prior to amplification of the target RNA reduces and/or prevents amplification bias of the target RNA by at least about 10-fold as compared to amplification of a target RNA without pre-hybridization with a TSO. Alternatively, hybridization of the TSO to the target RNA prior to amplification of the target RNA reduces and/or prevents amplification bias of the target RNA by at least about 100-fold as compared to amplification of a target RNA without pre-hybridization with a TSO. Hybridization of the TSO to the target RNA prior to amplification of the target RNA can reduce and/or prevent amplification bias of the target RNA by at least about 200-fold as compared to amplification of a target RNA without pre-hybridization with a TSO. In some instances, hybridization of the TSO to the target RNA prior to amplification of the target RNA reduces and/or prevents amplification bias of the target RNA by at least about 300-fold as compared to amplification of a target RNA without pre-hybridization with a TSO. In other instances, hybridization of the TSO to the target RNA prior to amplification of the target RNA reduces and/or prevents amplification bias of the target RNA by at least about 400-fold as compared to amplification of a target RNA without pre-hybridization with a TSO. Alternatively, hybridization of the TSO to the target RNA prior to amplification of the target RNA reduces and/or prevents amplification bias of the target RNA by at least about 500-fold as compared to amplification of a target RNA without pre-hybridization with a TSO. Hybridization of the TSO to the target RNA prior to amplification of the target RNA can reduce and/or prevent amplification bias of the target RNA by at least about 600-fold as compared to amplification of a target RNA without pre-hybridization with a TSO. In other instances, hybridization of the TSO to the target RNA prior to amplification of the target RNA reduces and/or prevents amplification bias of the target RNA by at least about 700-fold as compared to amplification of a target RNA without pre-hybridization with a TSO. Alternatively, hybridization of the TSO to the target RNA prior to amplification of the target RNA reduces and/or prevents amplification bias of the target RNA by at least about 800-fold as compared to amplification of a target RNA without pre-hybridization with a TSO. Hybridization of the TSO to the target RNA prior to amplification of the target RNA can reduce and/or prevent amplification bias of the target RNA by at least about 900-fold as compared to amplification of a target RNA without pre-hybridization with a TSO. In other instances, hybridization of the TSO to the target RNA prior to amplification of the target RNA reduces and/or prevents amplification bias of the target RNA by at least about 1000-fold as compared to amplification of a target RNA without pre-hybridization with a TSO. Alternatively, hybridization of the TSO to the target RNA prior to amplification of the target RNA reduces and/or prevents amplification bias of the target RNA by at least about 1500-fold as compared to amplification of a target RNA without pre-hybridization with a TSO. Hybridization of the TSO to the target RNA prior to amplification of the target RNA can reduce and/or prevent amplification bias of the target RNA by at least about 2000-fold as compared to amplification of a target RNA without pre-hybridization with a TSO.

The methods, compositions and kits can further comprise reducing and/or inhibiting amplification of non-target RNAs. In some instances, amplification of the non-target RNAs is reduced and/or inhibited by at least about 10%, 20%, 30%, 40%, 50% or more as compared to an amplification reaction without a TSO. In other instances, amplification of the non-target RNAs is reduced and/or inhibited by at least about 55% as compared to an amplification reaction without a TSO. Alternatively, amplification of the non-target RNAs is reduced and/or inhibited by at least about 60% as compared to an amplification reaction without a TSO. Amplification of the non-target RNAs can be reduced and/or inhibited by at least about 65% as compared to an amplification reaction without a TSO. In some instances, amplification of the non-target RNAs is reduced and/or inhibited by at least about 70% as compared to an amplification reaction without a TSO. In other instances, amplification of the non-target RNAs is reduced and/or inhibited by at least about 75% as compared to an amplification reaction without a TSO. Alternatively, amplification of the non-target RNAs is reduced and/or inhibited by at least about 80% as compared to an amplification reaction without a TSO. Amplification of the non-target RNAs can be reduced and/or inhibited by at least about 85% as compared to an amplification reaction without a TSO. In some instances, amplification of the non-target RNAs is reduced and/or inhibited by at least about 90% as compared to an amplification reaction without a TSO. In other instances, amplification of the non-target RNAs is reduced and/or inhibited by at least about 95% as compared to an amplification reaction without a TSO. Alternatively, amplification of the non-target RNAs is reduced and/or inhibited by at least about 97% as compared to an amplification reaction without a TSO. Amplification of the non-target RNAs can be reduced and/or inhibited by about 100% as compared to an amplification reaction without a TSO.

In some instances, amplification of the non-target RNAs is reduced and/or inhibited by at least about 2, 3, 4, 5, 10, 15, 20, 25, 30, 40, 50, 60, 70, 80, 90, or 100-fold or more as compared to an amplification reaction without a TSO. In other instances, amplification of the non-target RNAs is reduced and/or inhibited by at least about 200, 300, 400, 500, 600, 700, 800, 900, or 1000-fold or more as compared to an amplification reaction without a TSO. Alternatively, amplification of the non-target RNAs is reduced and/or inhibited by at least about 1100, 1200, 1300, 1400, 1500, 2000, 2500, 3000, 3500, 4000, 4500, 5000, 5500, 6000, 6500, 7000, 7500, 8000, 8500, 9000, 9500, or 10000-fold or more as compared to an amplification reaction without a TSO.

VII. Isolation and/or Purification of Target RNAs

The methods, compositions, and kits disclosed herein can further comprise isolation and/or purification of a target RNA or derivative thereof. The target RNA derivatives can be any of the forms or products of a target RNA as disclosed herein. In some instances, a target RNA derivative comprises a TSO-hybridized target RNA, adapter-ligated target RNA, amplified target RNA, amplified target RNA-specific sequence, sequenced target RNA, or any combination thereof. In some instances, isolation and/or purification of a target RNA or derivative thereof can comprise electrophoresis. In some instances, electrophoresis comprises gel electrophoresis or capillary electrophoresis.

In some instances, isolation and/or purification of a target RNA or derivative thereof comprises the use of one or more substrates. In other instances, isolation and/or purification of a target RNA or derivative thereof comprises attachment of the target RNA or derivative thereof to one or more substrates. As used herein, the term "substrate" refers to a material or group of materials having a rigid or semi-rigid surface or surfaces. The substrate can be a solid support. Alternatively, the substrate is a non-solid support. In some instances, the support comprises a membrane, paper, plastic, coated surface, flat surface, glass, slide, chip, or any combination thereof. In some instances, at least one surface of the solid support will be substantially flat. Alternatively, the substrate comprises physically separate synthesis regions for different compounds with, for example, wells, raised regions, pins, etched trenches, or the like. In other instances, the substrate comprises beads, resins, gels, microspheres, or other geometric configurations. Alternatively, the substrates comprise silica chips, microparticles, nanoparticles, plates, and arrays. In some instances, isolation and/or purification of the target RNA or derivative thereof comprises hybridization of the target RNA or derivative thereof to the substrate. In some instances, isolation and/or purification of the target RNA or derivative thereof comprises the use of one or more beads. In some instances, the beads are magnetic and/or streptavidin-coated beads. In some instances, the beads are beads coated by antibodies specific to a hapten group attached to the TSO.

Alternatively, or additionally, isolation and/or purification of the target RNA or derivative thereof comprises one or more wash buffers. In some instances, isolation and/or purification of the target RNA or derivative thereof comprises one or more wash steps. For example, isolation and/or purification can comprise (a) immobilizing the target RNA or derivative thereof to a substrate; (b) applying a wash buffer to the substrate; and (c) removing the wash buffer and unbound molecules, thereby isolating and/or purifying the target RNA or derivative thereof.

VIII. Detection and/or Quantification of Target RNAs

The methods, compositions, and kits disclosed herein further comprise detection and/or quantification of a target RNA or derivative thereof. In some instances, detection and/or quantification of the target RNA or derivative thereof comprises conducting a hybridization reaction, ligation reaction, reverse transcription reaction, amplification reaction, sequencing reaction, or any combination thereof. Detection and/or quantification of the target RNA or derivative thereof can comprise detection of the derivative of the target RNA. In some instances, the derivative of the target RNA comprises a TSO-hybridized target RNA, adapter-ligated target RNA, amplified target RNA, amplified target RNA-specific sequence, cRNA, sequenced target RNA, or any combination thereof. In some instances, the number of the derivative of the target RNAs detected directly corresponds to the number of target RNAs.

Detection and/or quantification of the target RNA or derivative thereof can comprise electrophoresis, spectroscopy, microscopy, fluorescence, immunofluorescence, colorimetry, chemiluminescence, and/or electrochemiluminescence methods. Alternatively, detection and/or quantification of the target RNA or derivative thereof comprises the use of an array detector, fluorescence reader, non-fluorescent detector, CR reader, luminometer, or scanner.

In some instances, detection and/or quantification of the target RNA or derivative thereof comprises conducting a sequencing reaction to determine the sequence of at least a portion of the target RNA or derivative thereof. Conducting a sequencing reaction can comprise next (or second) generation sequencing (NGS) technologies. In other instances, conducting a sequencing reaction can comprise third-generation sequencing such as direct, single-molecule sequencing. In some instances, conducting a sequencing reaction comprises Solexa sequencing (Illumina), 454 pyrosequencing (Roche), SOLiD sequencing and Ion Torrent™ (both from Life Technologies), Nanopore DNA sequencing, Lynx Therapeutics' Massively Parallel Signature Sequencing (MPSS), Single Molecule real time (RNAP) sequencing, Ion semiconductor sequencing, Single Molecule SMRT sequencing, Polony sequencing, DNA nanoball sequencing, and real-time single molecule sequencing. Alternatively, conducting a sequencing reaction uses one or more sequencing instruments, including, but not limited to, Genome Analyzer IIx, HiSeq, and MiSeq offered by Illumina, Single Molecule Real Time (SMRT™) technology, such as the PacBio RS system (Pacific Biosciences) and the Solexa Sequencer, and True Single Molecule Sequencing (tSMS™) technology such as the HeliScope™ single molecule sequencing (Helicos).

Conducting a sequencing reaction can comprise paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the labeled molecule or any product thereof can be determined by electron microscopy or a chemical-sensitive field effect transistor (chemFET) array.

Further disclosed herein, are methods, compositions, and kits for improving sequencing efficiency of a target RNA comprising (a) hybridizing one or more TSOs to one or more target RNAs to produce a TSO-hybridized target RNA; and (b) sequencing at least a portion of the TSO-hybridized target RNA or product thereof, wherein sequencing efficiency is dependent upon the hybridization of the one or more TSOs to the one or more target RNAs.

Sequencing efficiency can refer to the efficiency by which a target RNA, portion thereof, or product thereof is sequenced. In some instances, sequencing efficiency refers to the efficiency by which at least a portion of a TSO-hybridized target RNA is sequenced. Sequencing efficiency can refer to the efficiency by which at least a portion of an adapter-ligated target RNA is sequenced. In other instances, sequencing efficiency refers to the efficiency by which at least a portion of a linker-target RNA is sequenced. An increase in sequencing efficiency can refer to an increase in the number of TSO-hybridized target RNA that are sequenced. In other instances, an increase in sequencing efficiency can refer to an increase in the number of adapter-ligated target RNA that are sequenced. Increasing a sequencing efficiency can comprise increasing the number of sequencing reads of a target RNA or product thereof. Alternatively, or additionally, an increase in sequencing efficiency refers to a decrease in the number of sequencing reads of a non-target RNA. In some instances, increasing a sequencing efficiency refers to decrease in the number of non-target RNAs that are sequenced. In some instances, buffers, reagents, primers, and/or other components of an sequencing reaction directly or indirectly effect sequencing efficiency. In some instances, the methods, compositions, and kits disclosed herein increase a sequencing efficiency. In some instances, sequencing efficiency is increased with the addition of a TSO to the sequencing reaction. In other instances, sequencing efficiency is increased by pre-hybridization of a TSO to a target RNA. In some instances, hybridization of the TSO to a target RNA reduces and/or prevents the formation of one or more secondary structures in the target RNA or product thereof. In some instances, reduction and/or prevention of the formation of one or more secondary structures in the target RNA or product thereof increases the sequencing efficiency.

In some instances, hybridization of the TSO to the target RNA prior to sequencing of the target RNA improves sequencing efficiency of the target RNA by at least about 10%, 20%, 30%, 40%, 45%, 50%, 55%, 60% or more as compared to sequencing of a target RNA without pre-hybridization with a TSO. In other instances, hybridization of the TSO to the target RNA prior to sequencing of the target RNA improves sequencing of the target RNA by at least about 65% as compared to sequencing of a target RNA without pre-hybridization with a TSO. Alternatively, hybridization of the TSO to the target RNA prior to sequencing of the target RNA improves sequencing of the target RNA by at least about 70% as compared to sequencing of a target RNA without pre-hybridization with a TSO. Hybridization of the TSO to the target RNA prior to sequencing of the target RNA can improve sequencing of the target RNA by at least about 75% as compared to sequencing of a target RNA without pre-hybridization with a TSO. In some instances, hybridization of the TSO to the target RNA prior to sequencing of the target RNA improves sequencing of the target RNA by at least about 80% as compared to sequencing of a target RNA without pre-hybridization with a TSO. In other instances, hybridization of the TSO to the target RNA prior to sequencing of the target RNA improves sequencing of the target RNA by at least about 85% as compared to sequencing of a target RNA without pre-hybridization with a TSO. Alternatively, hybridization of the TSO to the target RNA prior to sequencing of the target RNA improves sequencing of the target RNA by at least about 90% as compared to sequencing of a target RNA without pre-hybridization with a TSO. Hybridization of the TSO to the target RNA prior to sequencing of the target RNA can improve sequencing of the target RNA by at least about 95% as compared to sequencing of a target RNA without pre-hybridization with a TSO.

In some instances, hybridization of the TSO to the target RNA prior to sequencing of the target RNA improves and/or increases sequencing efficiency of the target RNA by at least about 2, 3, 5, 10, 15, 20, 30, 40, 50, 60, 70, 80, 90, 100-fold or more as compared to sequencing of a target RNA without pre-hybridization with a TSO. In some instances, hybridization of the TSO to the target RNA prior to sequencing of the target RNA improves and/or increases sequencing efficiency of the target RNA by at least about 200, 300, 400, 500, 600, 700, 800, 900, 1000, 1500, 2000, 3000, 4000, 5000, 6000, 7000, 8000, 9000, 10000-fold or more as compared to sequencing of a target RNA without pre-hybridization with a TSO. In other instances, hybridization of the TSO to the target RNA prior to sequencing of the target RNA improves and/or increases sequencing efficiency of the target RNA by at least about 10-fold as compared to sequencing of a target RNA without pre-hybridization with a TSO. Alternatively, hybridization of the TSO to the target RNA prior to sequencing of the target RNA improves and/or increases sequencing efficiency of the target RNA by at least about 100-fold as compared to sequencing of a target RNA without pre-hybridization with a TSO. Hybridization of the TSO to the target RNA prior to sequencing of the target RNA can improve and/or increase sequencing efficiency of the target RNA by at least about 200-fold as compared to sequencing of a target RNA without pre-hybridization with a TSO. In some instances, hybridization of the TSO to the target RNA prior to sequencing of the target RNA improves and/or increases sequencing efficiency of the target RNA by at least about 300-fold as compared to sequencing of a target RNA without pre-hybridization with a TSO. In other instances, hybridization of the TSO to the target RNA prior to sequencing of the target RNA improves and/or increases sequencing efficiency of the target RNA by at least about 400-fold as compared to sequencing of a target RNA without pre-hybridization with a TSO. Alternatively, hybridization of the TSO to the target RNA prior to sequencing of the target RNA improves and/or increases sequencing efficiency of the target RNA by at least about 500-fold as compared to sequencing of a target RNA without pre-hybridization with a TSO. Hybridization of the TSO to the target RNA prior to sequencing of the target RNA can improve and/or increase sequencing efficiency of the target RNA by at least about 600-fold as compared to sequencing of a target RNA without pre-hybridization with a TSO. In other instances, hybridization of the TSO to the target RNA prior to sequencing of the target RNA improves and/or increases sequencing efficiency of the target RNA by at least about 700-fold as compared to sequencing of a target RNA without pre-hybridization with a TSO. Alternatively, hybridization of the TSO to the target RNA prior to sequencing of the target RNA improves and/or increases sequencing efficiency of the target RNA by at least about 800-fold as compared to sequencing of a target RNA without pre-hybridization with a TSO. Hybridization of the TSO to the target RNA prior to sequencing of the target RNA can improve and/or increase sequencing efficiency of the target RNA by at least about 900-fold as compared to sequencing of a target RNA without pre-hybridization with a TSO. In other instances, hybridization of the TSO to the target RNA prior to sequencing of the target RNA improves and/or increases sequencing efficiency of the target RNA by at least about 1000-fold as compared to sequencing of a target RNA without pre-hybridization with a TSO. Alternatively, hybridization of the TSO to the target RNA prior to sequencing of the target RNA improves and/or increases sequencing efficiency of the target RNA by at least about 1500-fold as compared to sequencing of a target RNA without pre-hybridization with a TSO. Hybridization of the TSO to the target RNA prior to sequencing of the target RNA can improve and/or increase sequencing efficiency of the target RNA by at least about 2000-fold as compared to sequencing of a target RNA without pre-hybridization with a TSO.

Further disclosed herein, are methods, compositions, and kits for reducing and/or preventing sequencing bias comprising (a) hybridizing one or more TSOs to one or more target RNAs to produce a TSO-hybridized target RNA; and (b) sequencing at least a portion of the TSO-hybridized target RNA, wherein sequencing of the target RNA is significantly independent of sequencing bias. In some instances, sequencing at least a portion of the TSO-hybridized target RNA is dependent upon the hybridization of the one or more TSOs to the one or more target RNAs.

In some instances, sequencing bias refers to the bias by which a target (e.g., target RNA or product thereof) is sequenced. In some instances, sequencing bias refers to the preferential sequencing of a target RNA, portion thereof or a product thereof over the sequencing of another target RNA, portion thereof or a product thereof. Alternatively, sequencing bias refers to the disproportionate sequencing of one or more target RNAs. In some instances, the number of target RNAs sequenced or the number of sequence reads for a target RNA is not an accurate reflection of the actual number of target RNAs in the sample. For example, a sample comprises similar or equal number of copies of target RNA A and target RNA B, however, after conducting a sequencing reaction, there are a substantially greater number (e.g., 2-fold or more, at least about 10% or more) sequencing reads of adapter-sequenced target RNA A in the sample than adapter-sequenced target RNA B. A decrease in sequencing bias can refer to a decrease in the disproportionate sequencing of one or more nucleotides to one or more targets. In some instances, the methods, compositions, and kits disclosed herein reduce and/or prevent a sequencing bias. In some instances, sequencing bias is reduced and/or prevented with the addition of a TSO to the sequencing reaction. In other instances, sequencing bias is reduced and/or prevented by pre-hybridization of a TSO to a target RNA. In some instances, hybridization of the TSO to a target RNA reduces and/or prevents the formation of one or more secondary structures in the target RNA or product thereof. In some instances, reduction and/or prevention of the formation of one or more secondary structures in the target RNA or product thereof reduces and/or prevents the sequencing bias.

In some instances, hybridization of the TSO to the target RNA prior to sequencing of the target RNA reduces and/or prevents sequencing bias of the target RNA by at least about 10%, 20%, 30%, 40%, 45%, 50%, 55%, 60% or more as compared to sequencing of a target RNA without pre-hybridization with a TSO. In other instances, hybridization of the TSO to the target RNA prior to sequencing of the target RNA reduces and/or prevents sequencing bias of the target RNA by at least about 65% as compared to sequencing of a target RNA without pre-hybridization with a TSO. Alternatively, hybridization of the TSO to the target RNA prior to sequencing of the target RNA reduces and/or prevents sequencing bias of the target RNA by at least about 70% as compared to sequencing of a target RNA without pre-hybridization with a TSO. Hybridization of the TSO to the target RNA prior to sequencing of the target RNA can reduce and/or prevent sequencing bias of the target RNA by at least about 75% as compared to sequencing of a target RNA without pre-hybridization with a TSO. In some instances, hybridization of the TSO to the target RNA prior to sequencing of the target RNA reduces and/or prevents sequencing bias of the target RNA by at least about 80% as compared to sequencing of a target RNA without pre-hybridization with a TSO. In other instances, hybridization of the TSO to the target RNA prior to sequencing of the target RNA reduces and/or prevents sequencing bias of the target RNA by at least about 85% as compared to sequencing of a target RNA without pre-hybridization with a TSO. Alternatively, hybridization of the TSO to the target RNA prior to sequencing of the target RNA reduces and/or prevents sequencing bias of the target RNA by at least about 90% as compared to sequencing of a target RNA without pre-hybridization with a TSO. Hybridization of the TSO to the target RNA prior to sequencing of the target RNA can reduce and/or prevent sequencing bias of the target RNA by at least about 95% as compared to sequencing of a target RNA without pre-hybridization with a TSO.

In some instances, hybridization of the TSO to the target RNA prior to sequencing of the target RNA reduces and/or prevents sequencing bias of the target RNA by at least about 2, 3, 5, 10, 15, 20, 30, 40, 50, 60, 70, 80, 90, 100-fold or more as compared to sequencing of a target RNA without pre-hybridization with a TSO. In some instances, hybridization of the TSO to the target RNA prior to sequencing of the target RNA reduces and/or prevents sequencing bias of the target RNA by at least about 200, 300, 400, 500, 600, 700, 800, 900, 1000, 1500, 2000, 3000, 4000, 5000, 6000, 7000, 8000, 9000, 10000-fold or more as compared to sequencing of a target RNA without pre-hybridization with a TSO. In other instances, hybridization of the TSO to the target RNA prior to sequencing of the target RNA reduces and/or prevents sequencing bias of the target RNA by at least about 10-fold as compared to sequencing of a target RNA without pre-hybridization with a TSO. Alternatively, hybridization of the TSO to the target RNA prior to sequencing of the target RNA reduces and/or prevents sequencing bias of the target RNA by at least about 100-fold as compared to sequencing of a target RNA without pre-hybridization with a TSO. Hybridization of the TSO to the target RNA prior to sequencing of the target RNA can reduce and/or prevent sequencing bias of the target RNA by at least about 200-fold as compared to sequencing of a target RNA without pre-hybridization with a TSO. In some instances, hybridization of the TSO to the target RNA prior to sequencing of the target RNA reduces and/or prevents sequencing bias of the target RNA by at least about 300-fold as compared to sequencing of a target RNA without pre-hybridization with a TSO. In other instances, hybridization of the TSO to the target RNA prior to sequencing of the target RNA reduces and/or prevents sequencing bias of the target RNA by at least about 400-fold as compared to sequencing of a target RNA without pre-hybridization with a TSO. Alternatively, hybridization of the TSO to the target RNA prior to sequencing of the target RNA reduces and/or prevents sequencing bias of the target RNA by at least about 500-fold as compared to sequencing of a target RNA without pre-hybridization with a TSO. Hybridization of the TSO to the target RNA prior to sequencing of the target RNA can reduce and/or prevent sequencing bias of the target RNA by at least about 600-fold as compared to sequencing of a target RNA without pre-hybridization with a TSO. In other instances, hybridization of the TSO to the target RNA prior to sequencing of the target RNA reduces and/or prevents sequencing bias of the target RNA by at least about 700-fold as compared to sequencing of a target RNA without pre-hybridization with a TSO. Alternatively, hybridization of the TSO to the target RNA prior to sequencing of the target RNA reduces and/or prevents sequencing bias of the target RNA by at least about 800-fold as compared to sequencing of a target RNA without pre-hybridization with a TSO. Hybridization of the TSO to the target RNA prior to sequencing of the target RNA can reduce and/or prevent sequencing bias of the target RNA by at least about 900-fold as compared to sequencing of a target RNA without pre-hybridization with a TSO. In other instances, hybridization of the TSO to the target RNA prior to sequencing of the target RNA reduces and/or prevents sequencing bias of the target RNA by at least about 1000-fold as compared to sequencing of a target RNA without pre-hybridization with a TSO. Alternatively, hybridization of the TSO to the target RNA prior to sequencing of the target RNA reduces and/or prevents sequencing bias of the target RNA by at least about 1500-fold as compared to sequencing of a target RNA without pre-hybridization with a TSO. Hybridization of the TSO to the target RNA prior to sequencing of the target RNA can reduce and/or prevent sequencing bias of the target RNA by at least about 2000-fold as compared to sequencing of a target RNA without pre-hybridization with a TSO.

The methods, compositions and kits can further comprise reducing and/or inhibiting sequencing to non-target RNAs. In some instances, sequencing to the non-target RNAs is reduced and/or inhibited by at least about 10%, 20%, 30%, 40%, 50% or more as compared to a sequencing reaction without a TSO. In other instances, sequencing to the non-target RNAs is reduced and/or inhibited by at least about 55% as compared to a sequencing reaction without a TSO. Alternatively, sequencing to the non-target RNAs is reduced and/or inhibited by at least about 60% as compared to a sequencing reaction without a TSO. Sequencing to the non-target RNAs can be reduced and/or inhibited by at least about 65% as compared to a sequencing reaction without a TSO. In some instances, sequencing to the non-target RNAs is reduced and/or inhibited by at least about 70% as compared to a sequencing reaction without a TSO. In other instances, sequencing to the non-target RNAs is reduced and/or inhibited by at least about 75% as compared to a sequencing reaction without a TSO. Alternatively, sequencing to the non-target RNAs is reduced and/or inhibited by at least about 80% as compared to a sequencing reaction without a TSO. Sequencing to the non-target RNAs can be reduced and/or inhibited by at least about 85% as compared to a sequencing reaction without a TSO. In some instances, sequencing to the non-target RNAs is reduced and/or inhibited by at least about 90% as compared to a sequencing reaction without a TSO. In other instances, sequencing to the non-target RNAs is reduced and/or inhibited by at least about 95% as compared to a sequencing reaction without a TSO. Alternatively, sequencing to the non-target RNAs is reduced and/or inhibited by at least about 97% as compared to a sequencing reaction without a TSO. Sequencing to the non-target RNAs can be reduced and/or inhibited by about 100% as compared to a sequencing reaction without a TSO.

In some instances, sequencing to the non-target RNAs is reduced and/or inhibited by at least about 2, 3, 4, 5, 10, 15, 20, 25, 30, 40, 50, 60, 70, 80, 90, or 100-fold or more as compared to a sequencing reaction without a TSO. In other instances, sequencing to the non-target RNAs is reduced and/or inhibited by at least about 200, 300, 400, 500, 600, 700, 800, 900, or 1000-fold or more as compared to a sequencing reaction without a TSO. Alternatively, sequencing to the non-target RNAs is reduced and/or inhibited by at least about 1100, 1200, 1300, 1400, 1500, 2000, 2500, 3000, 3500, 4000, 4500, 5000, 5500, 6000, 6500, 7000, 7500, 8000, 8500, 9000, 9500, or 10000-fold or more as compared to a sequencing reaction without a TSO.

The methods, compositions, and kits can reduce the amount of irrelevant sequencing reads. The methods, compositions, and kits can reduce the amount of irrelevant sequencing reads by at least about 10%, 20%, 30%, 40%, 50% or more as compared to sequencing reactions without a TSO. In some instances, the methods, compositions, and kits reduce the amount of irrelevant sequencing reads by at least about 60% as compared to sequencing reactions without a TSO. In other instances, the methods, compositions, and kits reduce the amount of irrelevant sequencing reads by at least about 65% as compared to sequencing reactions without a TSO. Alternatively, the methods, compositions, and kits reduce the amount of irrelevant sequencing reads by at least about 70% as compared to sequencing reactions without a TSO. The methods, compositions, and kits can reduce the amount of irrelevant sequencing reads by at least about 75% as compared to sequencing reactions without a TSO. In some instances, the methods, compositions, and kits reduce the amount of irrelevant sequencing reads by at least about 80% as compared to sequencing reactions without a TSO. In other instances, the methods, compositions, and kits reduce the amount of irrelevant sequencing reads by at least about 85% as compared to sequencing reactions without a TSO. Alternatively, the methods, compositions, and kits reduce the amount of irrelevant sequencing reads by at least about 90% as compared to sequencing reactions without a TSO. The methods, compositions, and kits can reduce the amount of irrelevant sequencing reads by at least about 95% as compared to sequencing reactions without a TSO. In some instances, the methods, compositions, and kits reduce the amount of irrelevant sequencing reads by at least about 97% as compared to sequencing reactions without a TSO. In other instances, the methods, compositions, and kits reduce the amount of irrelevant sequencing reads by at least about 99% as compared to sequencing reactions without a TSO. Alternatively, the methods, compositions, and kits reduce the amount of irrelevant sequencing reads by 100% as compared to sequencing reactions without a TSO.

IX. Exemplary Embodiments

A detailed description regarding various aspects of the invention is provided herein using miRNAs as examples. However, these embodiments can be applied equally well to other small RNAs such as siRNA, piRNA, ncRNA, snRNA, snoRNA, pre-miRNAs, or fragments of larger RNAs, i.e. collectively, "target RNAs".

Methods, compositions, and kits are provided herein for reducing and/or preventing the formation of secondary structures in target RNAs. In some instances, the methods, compositions and kits comprise hybridizing one or more TSOs to one or more target RNAs to produce a TSO-hybridized target RNA, thereby reducing and/or preventing the formation of one or more secondary structures in the target RNA.

Alternatively, the methods, compositions, and kits comprise contacting a sample comprising a plurality of molecules with one or more target-specific oligonucleotides (TSO) to produce a TSO-hybridized target RNA, wherein (i) the TSO comprises a sequence that is at least partially complementary to one or more target RNA molecules; (ii) the sequence of the TSO comprises at least one fewer nucleotide than the sequence of the target RNA molecule; (iii) a TSO-hybridized target RNA is produced from hybridization of the TSO to the target RNA molecule; and (iv) formation of the TSO-hybridized target RNA reduces or prevents the formation of intramolecular folding (e.g., one or more secondary structures) in the target RNA.

In some instances, the formation of one or more secondary structures in the target RNA is reduced by at least about 10%, 20%, 30%, 40%, 45%, 50%, or more as compared to without pre-hybridization with a TSO. In other instances, the formation of one or more secondary structures in the target RNA is reduced by at least about 55%. Alternatively, the formation of one or more secondary structures in the target RNA is reduced by at least about 60%. The formation of one or more secondary structures in the target RNA can be reduced by at least about 65%. In some instances, the formation of one or more secondary structures in the target RNA is reduced by at least about 70%. In other instances, the formation of one or more secondary structures in the target RNA is reduced by at least about 75%. Alternatively, the formation of one or more secondary structures in the target RNA is reduced by at least about 80%. The formation of one or more secondary structures in the target RNA can be reduced by at least about 85%. In some instances, the formation of one or more secondary structures in the target RNA is reduced by at least about 90%. In other instances, the formation of one or more secondary structures in the target RNA is reduced by at least about 95%. Alternatively, the formation of one or more secondary structures in the target RNA is reduced by at least about 97%. The formation of one or more secondary structures in the target RNA can be reduced by at least about 99%. In some instances, the formation of one or more secondary structures in the target RNA is reduced by 100%.

Further disclosed herein are methods, compositions and kits for reducing and/or preventing the formation of secondary structures by both target RNAs and adapter-ligated target RNA products. In some instances, the adapter-ligated target RNA products comprise 3'-adapter-ligated target RNA and/or 5'-adapter-ligated target RNA. In some instances, reducing and/or preventing the formation of such structures can result in a significant reduction in sequence-dependent biases for multiplex detection of different target RNAs. Alternatively, or additionally, reducing or preventing the formation of secondary structures in the target RNA and/or adapter-ligated target RNA allows for more accurate determination of the absolute copy numbers of the target RNA.

Further provided herein are methods, compositions and kits for expression profiling of a target RNA comprising (a) hybridizing a TSO to a target RNA to produce a TSO-hybridized target RNA; and (b) conducting a ligation reaction comprising one or more ligases, wherein (i) conducting a ligation reaction comprises circularization of one or more RNA molecules to produce a circularized RNA molecule; and (ii) the circularized RNA molecules do not comprise the TSO-hybridized target RNA. In some instances, the methods, compositions, and kits further comprise attachment of one or more adapters to the TSO-hybridized target RNA to produce an adapter-ligated target RNA. The methods, compositions and kits can further comprise reducing and/or inhibiting adapter ligation to non-target RNAs. In some instances, adapter ligation to the non-target RNAs is reduced and/or inhibited by at least about 50%. In some instances, the methods, compositions, and kits further comprise conducting a sequence reaction on the target RNA or derivative thereof. The methods, compositions, and kits can reduce the amount of irrelevant sequencing reads. The methods, compositions, and kits can reduce the amount of irrelevant sequencing reads by at least about 50%. In some instances, the methods, compositions, and kits disclosed herein improve analysis of the samples. In some instances, the methods, compositions, and kits facilitate detection of low-copy target RNAs.

In some embodiments are methods, compositions, and kits for attaching one or more adapters to a target RNA comprising (a) hybridizing a TSO to a target RNA to produce a TSO-hybridized target RNA; and (b) attaching one or more adapters to the target RNA portion of the TSO-hybridized target RNA to produce an adapter-ligated target RNA. In some instances, attachment of the one or more adapters to the target RNA is dependent on the efficiency of hybridization of the TSO to the target RNA.

In some instances, attachment of the one or more adapters to the target RNA is improved by at least about 70% as compared to a reaction without pre-hybridization with a TSO. In some instances, attachment of the one or more adapters comprises (a) attachment of a first adapter; and (b) attachment of a second adapter. Attachment of the first adapter can improve by at least about 70% as compared to attachment of a first adapter to a target RNA without a TSO. In some instances, attachment of the second adapter is improved by at least about 70% as compared to attachment of a second adapter to a target RNA without a TSO.

Disclosed herein, in some embodiments, is a method comprising contacting a sample comprising a plurality of target and non-target RNA molecules with one or more target-specific oligonucleotides (TSO) to produce a TSO-hybridized target RNA, wherein (i) the TSO comprises a sequence that is at least partially complementary to one or more target RNA molecules; (ii) the sequence of the TSO comprises at least one fewer nucleotide than the sequence of the target RNA molecule; (iii) a TSO-hybridized target RNA is produced from hybridization of the TSO to the target RNA molecule; and/or (iv) formation of the TSO-hybridized target RNA reduces or prevents the formation of one or more secondary structures in the target RNA. In some instances, the method further comprises attaching one or more adapters to the target RNA portion of the TSO-hybridized target RNA to produce an adapter-ligated RNA. In other instances, the method further comprises attaching a first adapter to the target RNA portion of the TSO-hybridized target RNA to produce an adapter-ligated RNA. Alternatively, or additionally, the method further comprises attaching a second adapter to the target RNA portion of the TSO-hybridized target RNA to produce a double-adapter-ligated RNA. The method can further comprise reverse transcribing at least a portion of the target RNA or a product thereof. In some instances, the method further comprises amplifying at least a portion of the target RNA. In other instances, the method further comprises isolating the target RNA or a product thereof. Alternatively, or additionally, the method further comprises enriching the target RNA or a product thereof. The method can further comprise detecting a product of the target RNA. In some instances, the method further comprises sequencing at least a portion of the target RNA or a product thereof. In other instances, the method further comprises cloning the target RNA or product thereof.

Further disclosed herein is a method comprising (a) contacting a sample comprising a plurality of molecules with one or more target-specific oligonucleotides (TSO) to produce a TSO-hybridized target RNA, wherein (i) the TSO comprises a sequence that is at least partially complementary to one or more target RNA molecules; (ii) the sequence of the TSO comprises at least one fewer nucleotide than the sequence of the target RNA molecule; and (iii) a TSO-hybridized target RNA is produced from hybridization of the TSO to the target RNA molecule; and (b) attaching one or more adapters to the target RNA portion of the TSO-hybridized target RNA to produce an adapter-ligated target RNA, wherein attachment of the adapters to the target RNA molecule is not significantly susceptible to ligation bias. The method can further comprise reverse transcribing at least a portion of the target RNA or a product thereof. In some instances, the method further comprises amplifying at least a portion of the target RNA. In other instances, the method further comprises isolating the target RNA or a product thereof. Alternatively, or additionally, the method further comprises enriching the target RNA or a product thereof. The method can further comprise detecting a product of the target RNA. In some instances, the method further comprises sequencing at least a portion of the target RNA or a product thereof. In other instances, the method further comprises cloning the target RNA or product thereof.

In some embodiments is a method comprising (a) contacting a sample comprising a plurality of molecules with one or more target-specific oligonucleotides (TSO) to produce a TSO-hybridized target RNA, wherein: (i) the TSO comprises a sequence that is at least partially complementary to one or more target RNA molecules; (ii) the sequence of the TSO comprises at least one fewer nucleotide than the sequence of the target RNA molecule; and (iii) a TSO-hybridized target RNA is produced from hybridization of the TSO to the target RNA molecule; (b) attaching one or more adapters to the target RNA portion of the TSO-hybridized target RNA to produce an adapter-ligated target RNA; and (c) detecting the adapter-ligated target RNA, thereby determining the number of target RNA molecules. The method can further comprise reverse transcribing at least a portion of the target RNA or a product thereof. In some instances, the method further comprises amplifying at least a portion of the target RNA. In other instances, the method further comprises isolating the target RNA or a product thereof. Alternatively, or additionally, the method further comprises enriching the target RNA or a product thereof. In some instances, the method further comprises sequencing at least a portion of the target RNA or a product thereof. In other instances, the method further comprises cloning the target RNA or product thereof.

Disclosed herein, in some embodiments, is a method comprising (a) contacting a sample comprising a plurality of molecules with one or more target-specific oligonucleotides (TSO) to produce a TSO-hybridized target RNA, wherein: (i) the TSO comprises a sequence that is at least partially complementary to one or more target RNA molecules; (ii) the sequence of the TSO comprises at least one fewer nucleotide than the sequence of the target RNA molecule; and (iii) a TSO-hybridized target RNA is produced from hybridization of the TSO to the target RNA molecule; (b) attaching one or more adapters to the target RNA portion of the TSO-hybridized target RNA to produce an adapter-ligated target RNA; and (c) amplifying the adapter-ligated target RNA, wherein amplification of the adapter-ligated target RNA is not significantly susceptible to amplification bias. The method can further comprise reverse transcribing at least a portion of the target RNA or a product thereof. In other instances, the method further comprises isolating the target RNA or a product thereof. Alternatively, or additionally, the method further comprises enriching the target RNA or a product thereof. The method can further comprise detecting a product of the target RNA. In some instances, the method further comprises sequencing at least a portion of the target RNA or a product thereof. In other instances, the method further comprises cloning the target RNA or product thereof.

Further disclosed herein, in some embodiments, is a method comprising (a) contacting a sample comprising a plurality of molecules with one or more target-specific oligonucleotides (TSO) to produce a TSO-hybridized target RNA, wherein: (i) the TSO comprises a sequence that is at least partially complementary to one or more target RNA molecules; (ii) the sequence of the TSO comprises at least one fewer nucleotide than the sequence of the target RNA molecule; and (iii) a TSO-hybridized target RNA is produced from hybridization of the TSO to the target RNA molecule; (b) attaching one or more adapters to the target RNA portion of the TSO-hybridized target RNA to produce an adapter-ligated target RNA; and (c) sequencing the adapter-ligated target RNA, wherein sequencing of the adapter-ligated target RNA is not significantly susceptible to sequencing bias. The method can further comprise reverse transcribing at least a portion of the target RNA or a product thereof. In some instances, the method further comprises amplifying at least a portion of the target RNA. In other instances, the method further comprises isolating the target RNA or a product thereof. Alternatively, or additionally, the method further comprises enriching the target RNA or a product thereof. The method can further comprise detecting a product of the target RNA. In other instances, the method further comprises cloning the target RNA or product thereof.

Provided herein, in some embodiments, is a method comprising (a) contacting a sample comprising a plurality of molecules with one or more target-specific oligonucleotides (TSO) to produce a TSO-hybridized target RNA, wherein: (i) the TSO comprises a sequence that is at least partially complementary to one or more target RNA molecules; (ii) the sequence of the TSO comprises at least one fewer nucleotide than the sequence of the target RNA molecule; and (iii) a TSO-hybridized target RNA is produced from hybridization of the TSO to the target RNA molecule; (b) attaching one or more adapters to the target RNA portion of the TSO-hybridized target RNA to produce an adapter-ligated target RNA; and (c) conducting a reverse transcription reaction on the adapter-ligated target RNA to produce a cRNA, wherein the cRNA comprises a DNA copy of the adapter-ligated target RNA. In some instances, the method further comprises amplifying at least a portion of the target RNA. In other instances, the method further comprises isolating the target RNA or a product thereof. Alternatively, or additionally, the method further comprises enriching the target RNA or a product thereof. The method can further comprise detecting a product of the target RNA. In some instances, the method further comprises sequencing at least a portion of the target RNA or a product thereof. In other instances, the method further comprises cloning the target RNA or product thereof.

Disclosed herein, in some embodiments, is a method comprising (a) contacting a sample comprising a plurality of molecules with one or more target-specific oligonucleotides (TSO) to produce a TSO-hybridized target RNA, wherein: (i) the TSO comprises a sequence that is at least partially complementary to one or more target RNA molecules; (ii) the sequence of the TSO comprises at least one fewer nucleotide than the sequence of the target RNA molecule; and (iii) a TSO-hybridized target RNA is produced from hybridization of the TSO to the target RNA molecule; (b) attaching one or more adapters to the target RNA portion of the TSO-hybridized target RNA to produce an adapter-ligated target RNA; and (c) isolating the adapter-ligated target, thereby producing a target RNA library. The method can further comprise reverse transcribing at least a portion of the target RNA or a product thereof. In some instances, the method further comprises amplifying at least a portion of the target RNA. In other instances, the method further comprises cloning the target RNA or product thereof. Alternatively, or additionally, the method further comprises enriching the target RNA or a product thereof. The method can further comprise detecting a product of the target RNA. In some instances, the method further comprises sequencing at least a portion of the target RNA or a product thereof.

Figure 2:
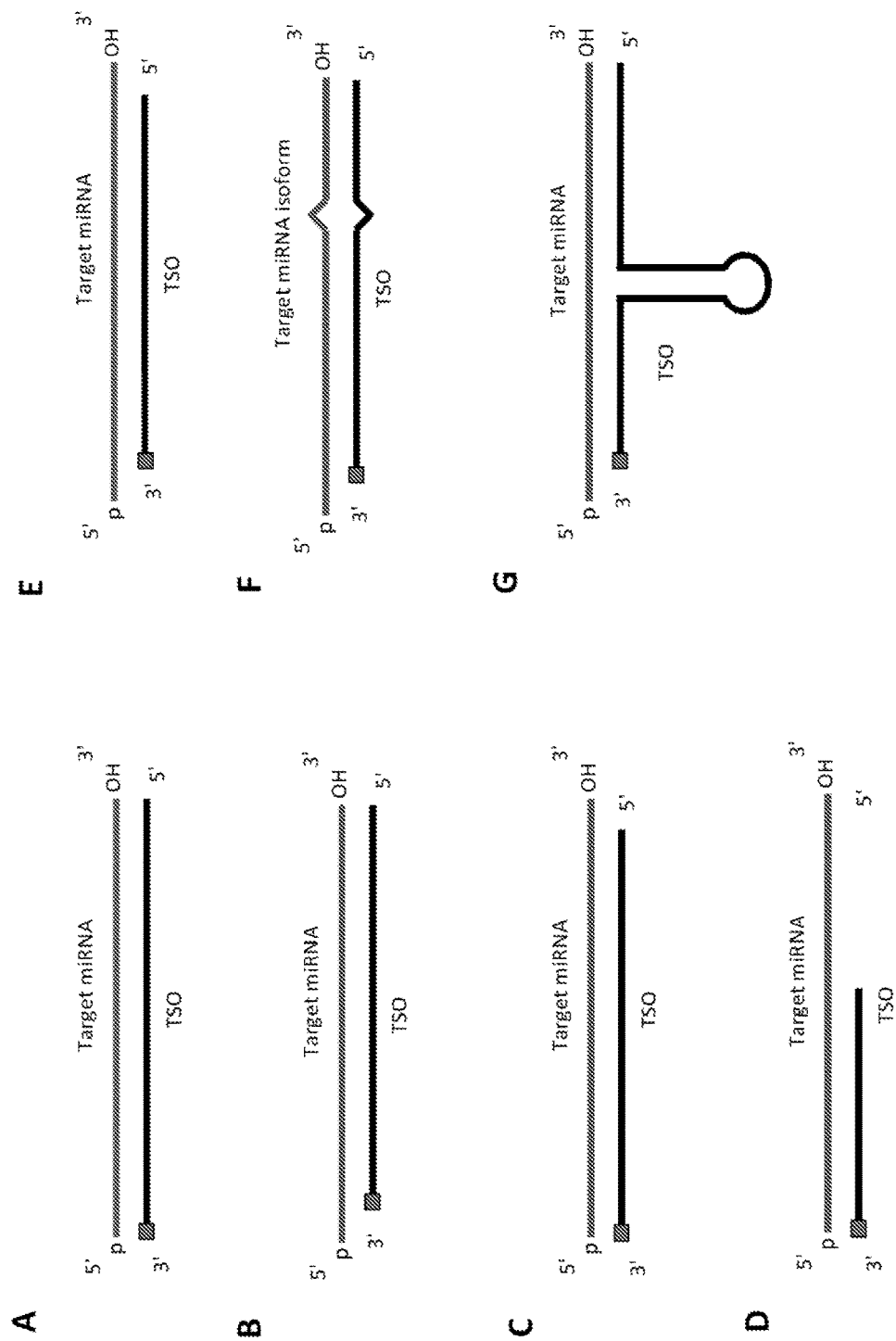
FIG. 2. Examples of miRNA-TSO hybridization complexes that satisfy the substrate requirements for enzymatic reactions used for the ligation or extension of the miRNA ends. The optimal structure of miRNA-TSO complexes may vary depending on the enzymes, enzymatic reaction conditions, and adapters used.
Figure 3:
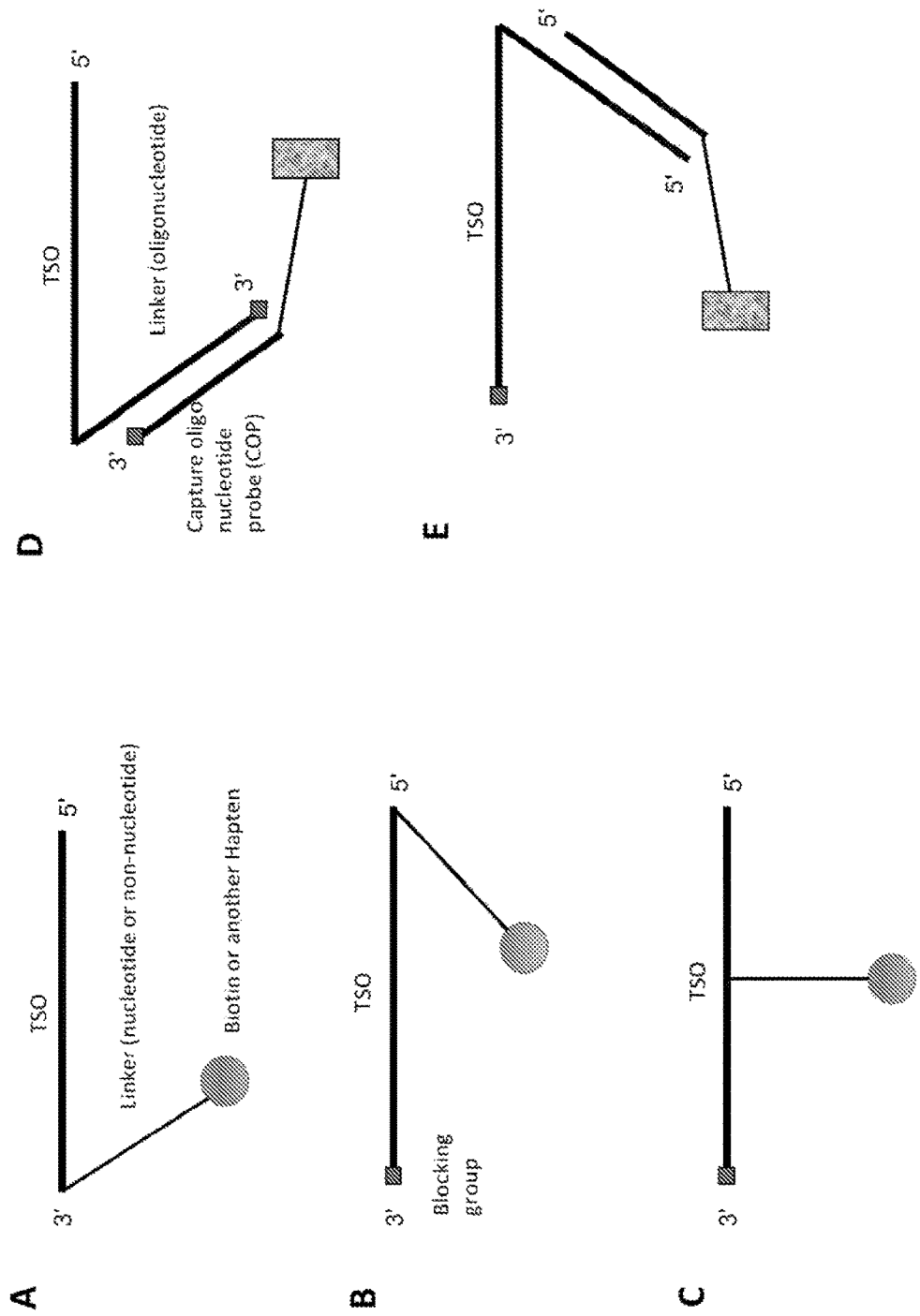
FIG. 3. Schematic representations of target-specific oligonucleotides (TSO) comprising modifications that allow their non-covalent immobilization to a solid phase. A-C: Examples of TSO carrying a hapten group such as biotin or digoxigenin attached to one of the TSO ends or internally via non-nucleotide and/or oligonucleotide linkers, that can bind with high affinity to surface-bound hapten-specific proteins such as streptavidin or a hapten-specific antibody. D-E: Examples of TSO extended at one end by an oligonucleotide linker that is complementary to a capture oligonucleotide probe (COP) immobilized on a solid support.
Figure 4:
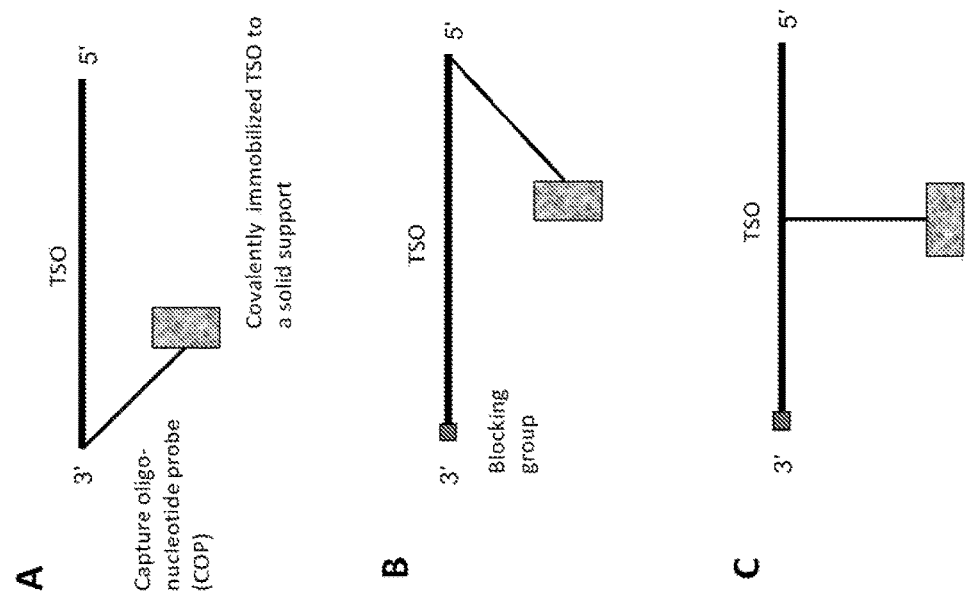
FIG. 4. Schematic representations of target-specific oligonucleotides (TSO) covalently immobilized onto a solid support. Examples of TSO attached to a solid support via non-nucleotide and/or oligonucleotide linkers are shown.

In aspects of the invention, a new platform technology called miR-ABLE (miRNA affinity binding before ligation and/or extension) is provided. In miR-ABLE, miRNAs bind to target-specific oligonucleotides (TSOs), which are designed to target known or predicted miRNAs or a group of related miRNAs (or other small RNAs or fragments of large RNAs), from various species or a specific group of species. In some instances, TSOs are specifically designed to perform some or all of the following functions: (1) unfold miRNA intramolecular (secondary) structures that inhibit adapter ligation to or extension of miRNA ends; (2) suppress circularization of target miRNAs under ligation conditions, while allowing non-target miRNAs to be circularized (FIG. 1) (circularization prevents adapter ligation to or extension of their ends, thus excluding them from subsequent amplification and detection.); (3) maintain the target miRNA ends in forms that are substrates for ligation or extension (the optimal structure of a miRNA-TSO complex depends on the relevant enzymatic reaction; examples are provided in FIG. 2.); and/or (4) provide capture of target miRNAs on a solid support through either non-covalent or covalent immobilization of the TSO (examples are provided in FIGS. 3-4).

In some instances, to avoid possible interference with ligation, extension or amplification reactions, TSOs are also designed in the ways that they cannot: (a) serve as template for miRNA 3'-end extension—by not producing a single-stranded overhang at the 5' end of the TSO when hybridized to the miRNA; (b) serve as a splint in ligation of miRNAs to adapters—by not producing a single-stranded overhang at the 5' end of the TSO when hybridized to the miRNA and also by avoiding accidental complementarity of TSO to the adapters/linkers; (c) serve as a primer—by possessing a blocking group at their 3' ends; (d) be ligated or extended—by possessing a blocking group at their 3' ends and/or by possessing a blocking group at their 5' ends that prevents 5' phosphorylation, such as: 5'-OMe (Chen et al. 2008b), a non-nucleotide linker, or other modifications known in the art; and/or (e) serve as a template for amplification—by avoiding complementarity to RT (reverse transcription) or PCR primers used, or by containing one or more residues that cannot be replicated by DNA polymerase, such as abasic site(s) or nucleoside(s) with 2'-OMe or 2'-F modifications (Stump et al. 1999; Knott et al. 2004), or by comprising an internal, stable hairpin.

In some instances, to provide these specific functions, TSOs comprise some or all of the following features: (a) their sequences are substantially complementary to target miRNAs, wherein the numbers of complementary base pairs (bp) between TSO and miRNA are equal to or less than the full length of miRNA, providing (single-stranded) overhangs of 0-6 nt at the miRNA 5' ends and 0-11 nt at the miRNA 3' ends (examples are provided in FIG. 2, with blunt ends marked as 0-nt overhang); (b) they can bind to more than one isoform (forming mismatched/imperfect duplexes) and/or isomir of a target miRNA (perfect sequence-specificity is not necessary since the captured miRNAs will be either sequenced or detected by sequence-specific methods such as arrays or by RT-qPCR); (c) their sequences are neither complementary to nor corresponding to sequences of adapters/linkers or RT-PCR primers used in the adapter ligation and amplification reactions; (d) they form duplexes with target miRNAs that have higher stability than any internal secondary structure of the miRNA under conditions of the ligation or extension reactions; (e) they consist of nucleotides selected from: RNA; DNA; a mix of DNA and RNA residues, or modified nucleotides such as 2'-OMe, or 2'-fluoro (2'-F), locked nucleic acid (LNA), abasic sites or any other nucleic acid modifications known in the art; and/or (f) they have blocked 3'-ends such as 3'-p, or 3'-amino, or 2',3'-dideoxy nucleoside (ddN), 3'-inverted (3'-3') deoxy nucleoside (idN), or any other modification known in the art that prevents ligation to or extension of the 3' end.

The specific designs of the TSO may vary depending on the type of adapters and enzymes that are used for the ligation, extension by nucleotidyl transferase, reverse transcription, and/or sequencing reactions. In some embodiments of the invention, TSOs have specific alignments with target miRNAs that upon binding to each other provide the following lengths of single-stranded overhangs at the miRNA ends: (1) 0 nt at 3' end—for ligation of a 5'-adenylated 3'-adapter by T4 RNA ligase 2 (Rnl2) or its derivatives (truncated or mutated versions) in the absence of ATP; (2) 0-2 nt at 3' end—for ligation of a 5'-adenylated 3'-adapter by T4 RNA ligase 1 (Rnl1) in the absence of ATP or a 5'-phosphorylated 3'-adapter by Rnl1 in the presence of ATP; (3) 3-4 nt at the 5' end—for ligation of a 5'-adapter by Rnl1 in the presence of ATP; (4) 4 nt at the 5' end and 0 nt at the 3' end—for sequential or simultaneous ligation of 3'- and 5'-adapters by Rnl1 in the presence of ATP; (5) 4 nt at the 5' end and 0 nt at the 3' end—for sequential ligation of a 5'-adenylated 3'-adapter by Rnl2 or its derivatives (truncated or mutated versions) in the absence of ATP and a 5'-adapter by Rnl1 in the presence of ATP for the Solexa and 454 NGS platforms; (6) 6 nt at both the 5' and 3' ends for simultaneous ligation by Rnl2 (or ligase) of 3'- and 5'-adapters for specific for the SOLiD or Ion Torrent NGS platforms; (7) 0 nt at 5' end and 1-3 nt at 3' end—for the ligation of a single 5'-phosphorylated 3'-adapter by Rnl1 in the presence of ATP; (8) 0 nt at the 5' end and 0 nt at the 3' end—for the ligation of a single 5'-adenylated 3'-adapter by Rnl2 or its derivatives (truncated or mutated versions) in the absence of ATP; (9) 0 nt at the 5' end and 1-3 nt at the 3' end—for the labeling of the 3' end with 5'-phosphorylated derivatives of mono- and dinucleotide signal moieties known in art by Rnl1 in the presence of ATP; (10) 0 nt at the 3' end for the labeling of the 3' end with 5'-adenylated derivatives of the mono- and dinucleotide signal moieties by Rnl2 or its derivatives (truncated and mutated versions) in the absence of ATP; and/or (11) 1-3 nt at the 3' end—for the extension by an RNA-specific nucleotidyl transferase such as poly(A) polymerase (PAP) or poly(U) polymerase as previously described (Sun et al. 2007; Yehudai-Resheff and Schuster 2000; Hafner et al. 2011).

In some embodiments of the invention, pools of synthetic TSOs targeting any desired number of known and/or predicted miRNAs are added to a sample and hybridized in solution with target miRNAs (Step 1.1, FIG. 5A) before the adapter ligation or extension steps. The samples may represent extracts from biologically and clinically relevant tissues, or cells, or extracellular fluids and are selected from: tissue or cell lysates, extracellular fluids, crude nucleic acid extracts; total RNA extracts; purified fractions of small RNAs whose length is limited by a method of the purification; or pools of synthetic miRNAs. The sequences of the adapters are dictated by the requirements of the specific NGS platform. The adapter sequences can be customized by incorporation of appropriate bar-codes (or indexes), restriction sites, primer sites, or promoters for RNA polymerases. The preparations of small RNA libraries can include either sequential (FIG. 5B) or simultaneous (FIG. 6) ligation of 3'- and 5'-adapters/linkers to miRNAs.

In some embodiments for the sequential ligation of adapters, Rnl1 is used for the ligation of both 3'- and 5'-adapters, wherein the 3'-adapter is 5'-preadenylated (5'-App) and ligated in the absence of ATP (FIG. 5B, Step 2.1/−ATP), after which the 5'-adapter is ligated in the presence of ATP (FIG. 5B, Step 3.1). In another embodiment of this invention, the 3'-adapter is 5'-phosphorylated (5'-p) and ligated in the presence of ATP (FIG. 5B, Step 2.1/+ATP). In other embodiments, Rnl2 or one of its derivatives (such as truncated and/or mutated versions) is used in Step 2.1/−ATP (FIG. 5B) instead of Rnl1 or in combination with Rnl1. In yet another embodiment of this invention, Rnl2 or one of its derivatives is used in both Steps 2.1 and 3.1, instead of Rnl1 or in combination with Rnl1. Use of a combination of Rnl1 and Rnl2 in the adapter-ligation reactions may reduce the biases that these enzymes may have (if used separately) toward different nucleotides and secondary structures at the ends of miRNAs and their isoforms/isomirs. The advantages of using Rnl1 (in comparison to Rnl2 or its derivatives) can include: (a) lower cost; (b) faster and more efficient ligation of adapters to target miRNAs; and (c) rapid circularization of the majority of non-target miRNAs, which can prevent their ligation with oligonucleotide adapters and, therefore, thereby providing enrichment of the sequencing libraries for the target miRNAs.

In another embodiment of this invention, the Solexa- or 454-style adapters are mixed and ligated to miRNAs simultaneously (rather than sequentially) by using Rnl1 or an Rnl1-Rnl2 combination in the presence of ATP as discussed above. In another embodiment of the invention, either Rnl2 or T4 DNA ligase is used for simultaneous ligation of SOLiD-style adapters to miRNAs (FIG. 6).

Figure 7B:
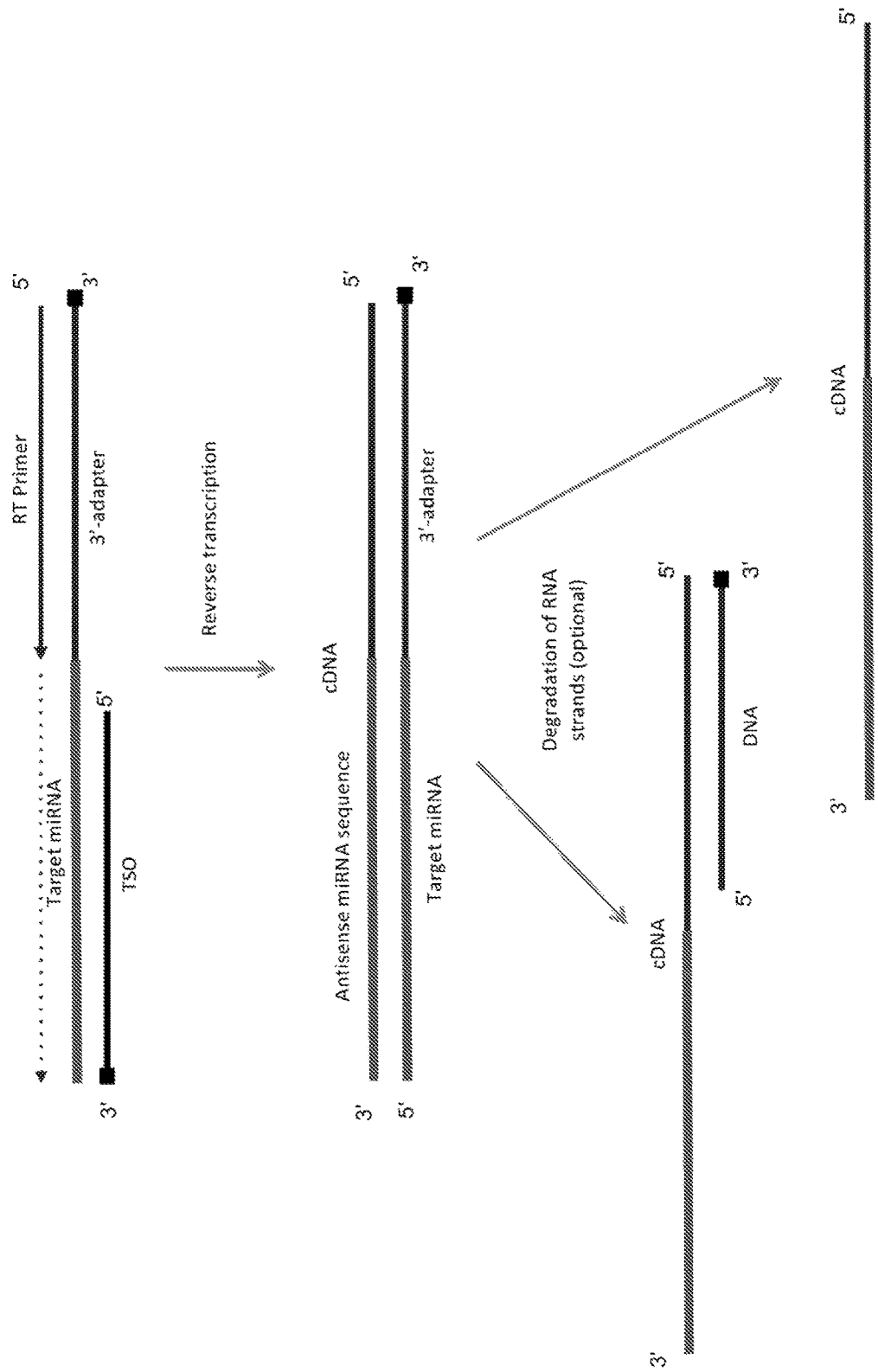
FIG. 7. Scheme of construction of an "miRNA library" comprising hybridization of target miRNAs with TSO and ligation of a single 3'-adapter to the miRNA 3' end (A), and optional reverse transcription (B) or transcription (C) of the ligation products. Degradation of RNA strands in the RT product generates single stranded cDNAs complementary to the target miRNAs (as shown in B).
Figure 7C:
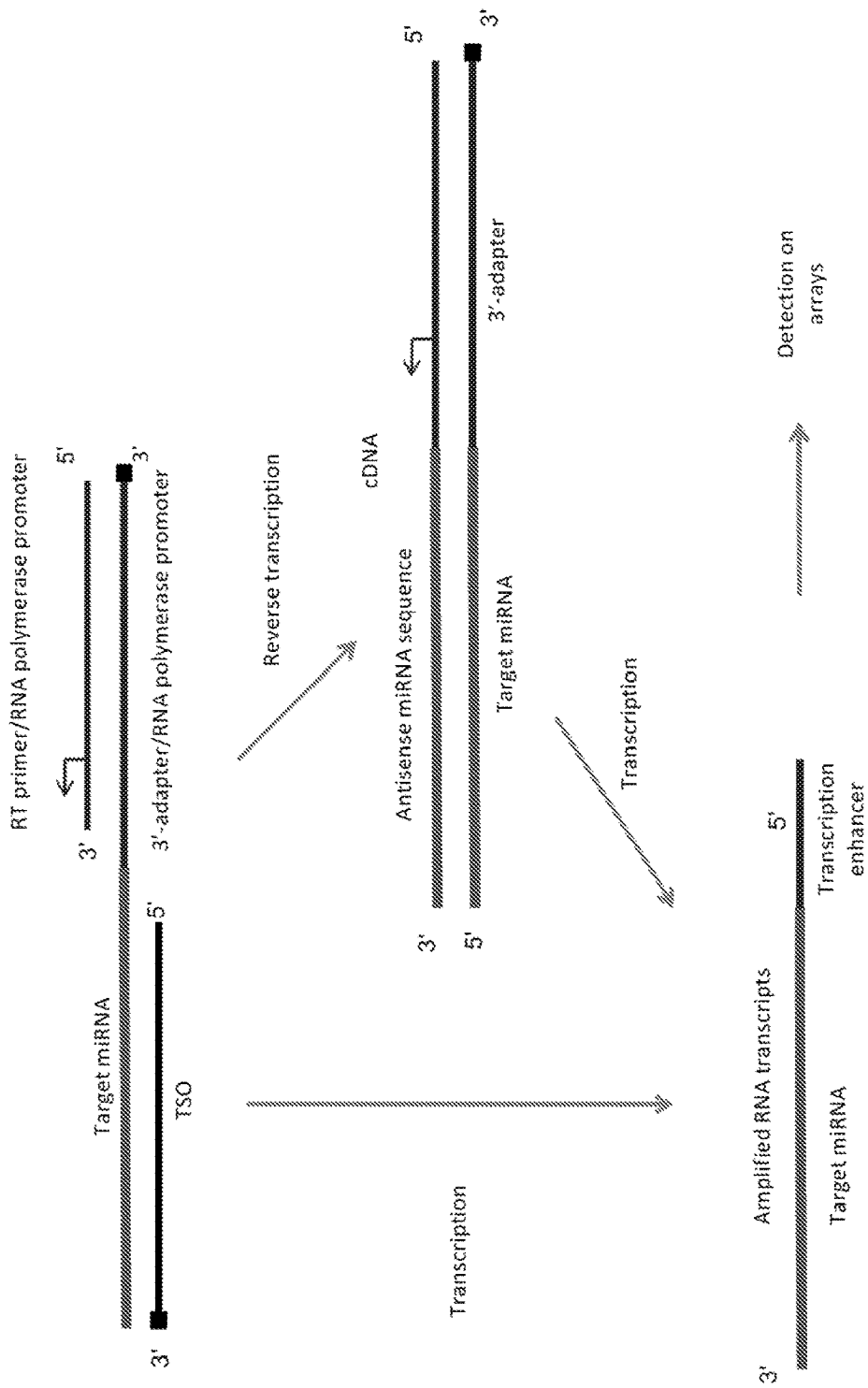

In another embodiment of the invention, a single 3'-adapter is ligated to the miRNAs by Rnl1 (FIG. 7A) according to one of the following schemes: (a) 5'-adenylated (5'-App) form of the adapter is ligated by Rnl1 in the absence of ATP (FIG. 5B, Step 2.1/−ATP); (b) 5'-phosphorylated (5'-p) form of the adapter is ligated by Rnl1 in the presence of ATP (FIG. 5B, Step 2.1/+ATP); (c) Rnl2 or one of its derivatives (such as truncated and mutated versions) is used in FIG. 5B, Step 2.1/−ATP instead of Rnl1; or (d) Rnl2 or one of its derivatives (such as truncated and mutated versions) is used in FIG. 5B, Step 2.1/−ATP in combination with Rnl1.

In some aspects of this invention, the 3'-adapters comprise one of more of the following features: (a) antisense primer sequences for RT; (b) promoter and transcriptional enhancer sequences for RNA polymerases that can use an RNA strand as template, such as bacteriophage T7 or T3 RNA polymerases or their mutants; (c) combined 3'-adapter (upstream) and 5'-adapter (downstream) sequences compatible with next-generation (second-generation) sequencing technologies such as Solexa, 454 or SOLiD; (d) single or multiple haptens such as biotin or digoxigenin; (e) single or multiple signal moieties; and/or (f) antisense tag or probe sequences that are appropriate for (sandwich) hybridization with bDNA.

In some other aspects of this invention, the 3'-adapters represent signal or signal-generating moieties selected from: [5'-*P]-labeled 5'-pNp-3' (pNp), where *P is a $^{32}$P or $^{33}$P radioisotope; 5'-pN-3'-n-linker-detectable moiety; 5'-AppN-3'-n-linker-detectable moiety; 5'-pNpN-n-linker-detectable moiety (Igloi 1996; Cole et al. 2004; Wang et al. 2007; Thomson et al., 2007b; Cole et al. 2009, 2010; Tuschl et al. 2011).

Figure 8A:
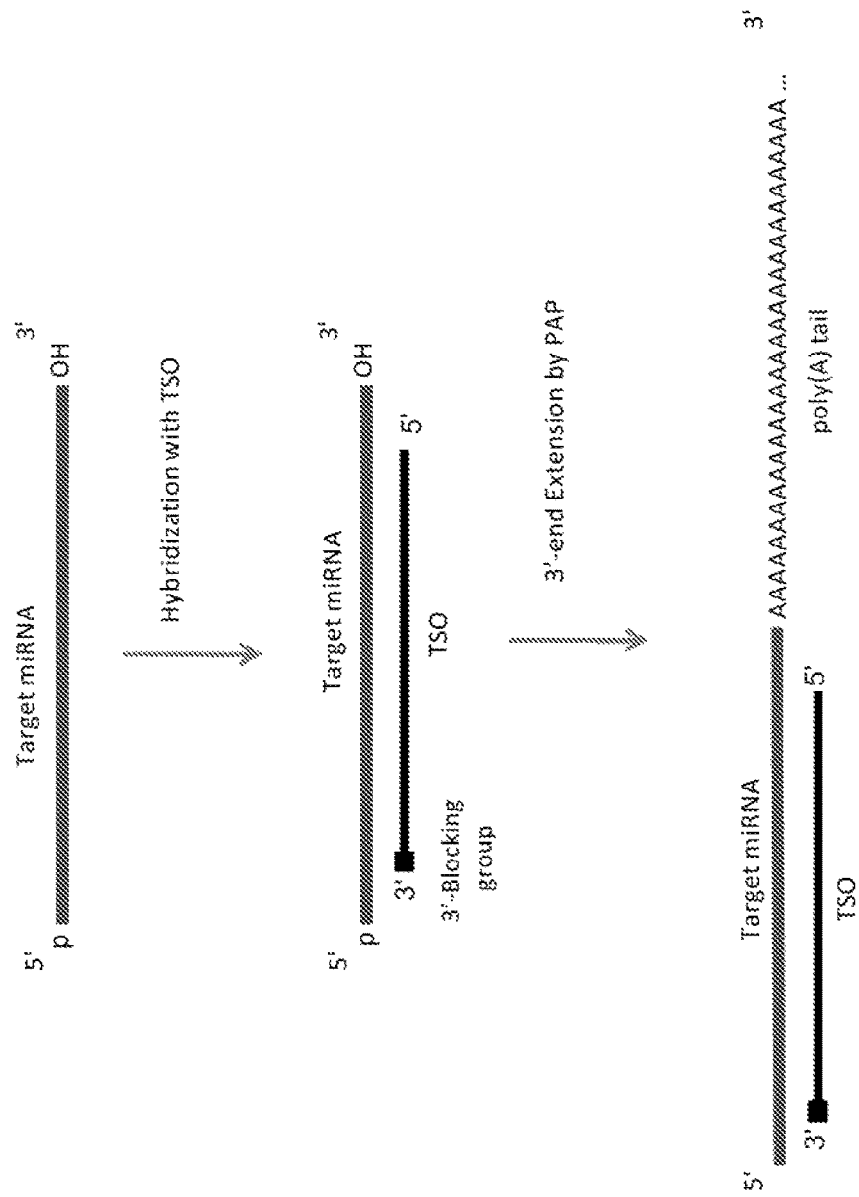
FIG. 8. Scheme of construction of an "miRNA library" comprising hybridization of target miRNAs with TSO and extension of the 3' end of the miRNA by a nucleotidyl transferase such as poly(A) polymerase (A); optional reverse transcription and degradation of RNA strands (B).
Figure 8B:
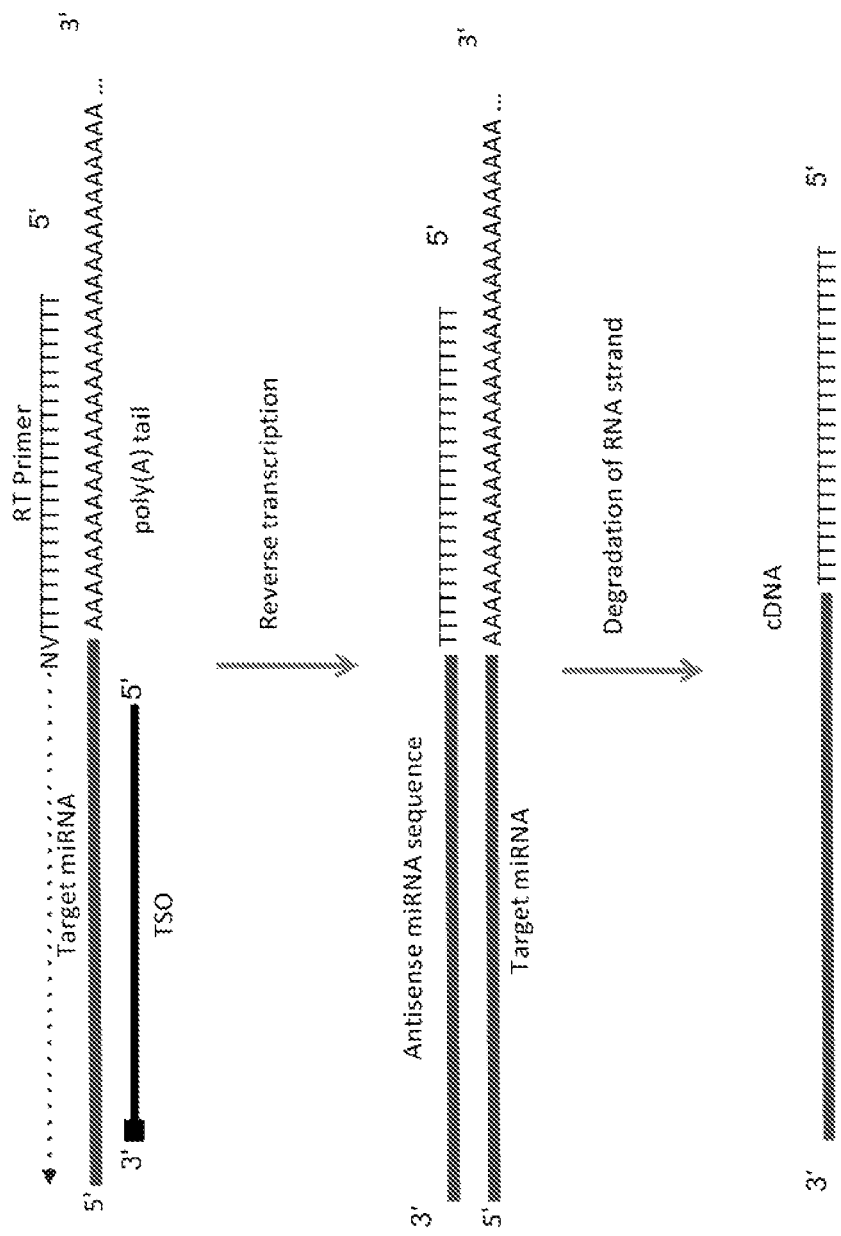

In another embodiment of this invention, 3' ends of miRNAs are extended by an RNA-specific nucleotidyl transferase such as poly(A) polymerase (PAP) (FIG. 8A) or poly(U) polymerase using an NTP selected from: ATP, UTP, CTP, GTP, ITP or derivatives of these NTP labeled by detectable moieties known in art such as radioactive isotopes, fluorophore, chemiluminescent groups, haptens or gold nanoparticles.

Figure 9A:
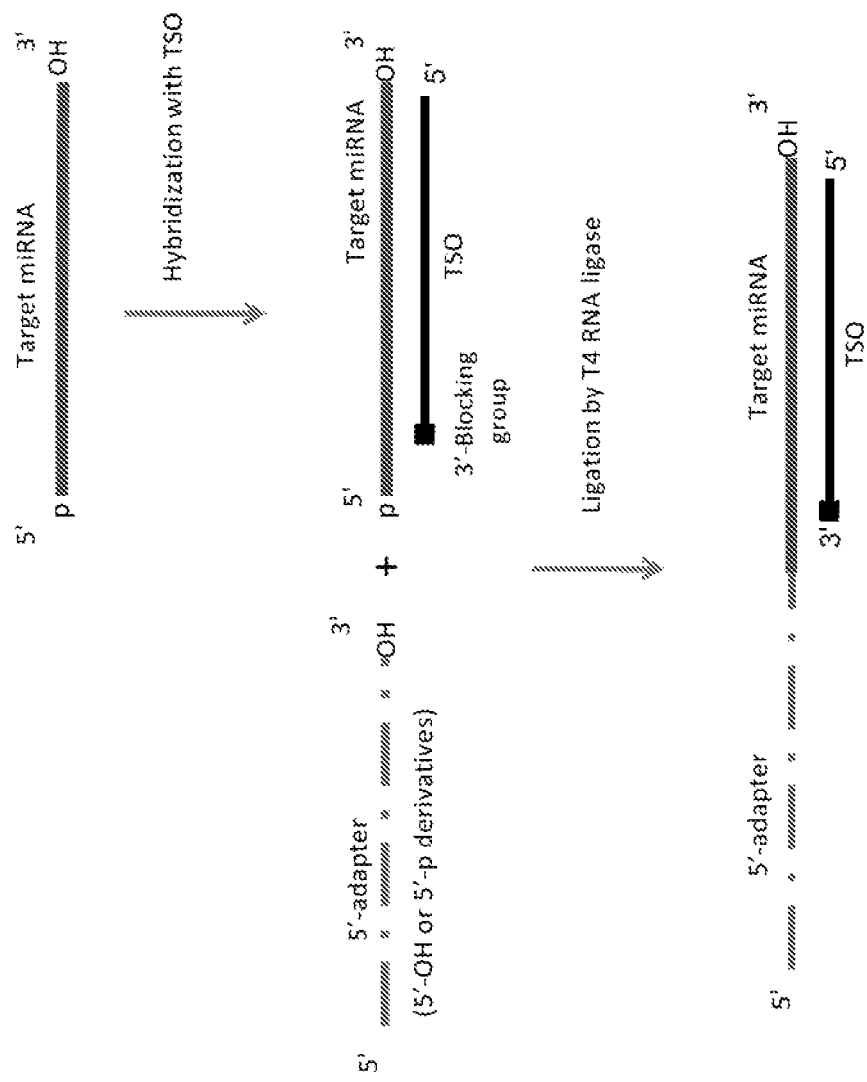
FIG. 9. Scheme of construction of an "miRNA library" comprising hybridization of target miRNAs with TSO and ligation of a single 5'-adapter to the 5' end of the miRNA (A); optional circularization of the ligation product and reverse transcription of the circular template (B).
Figure 10A:
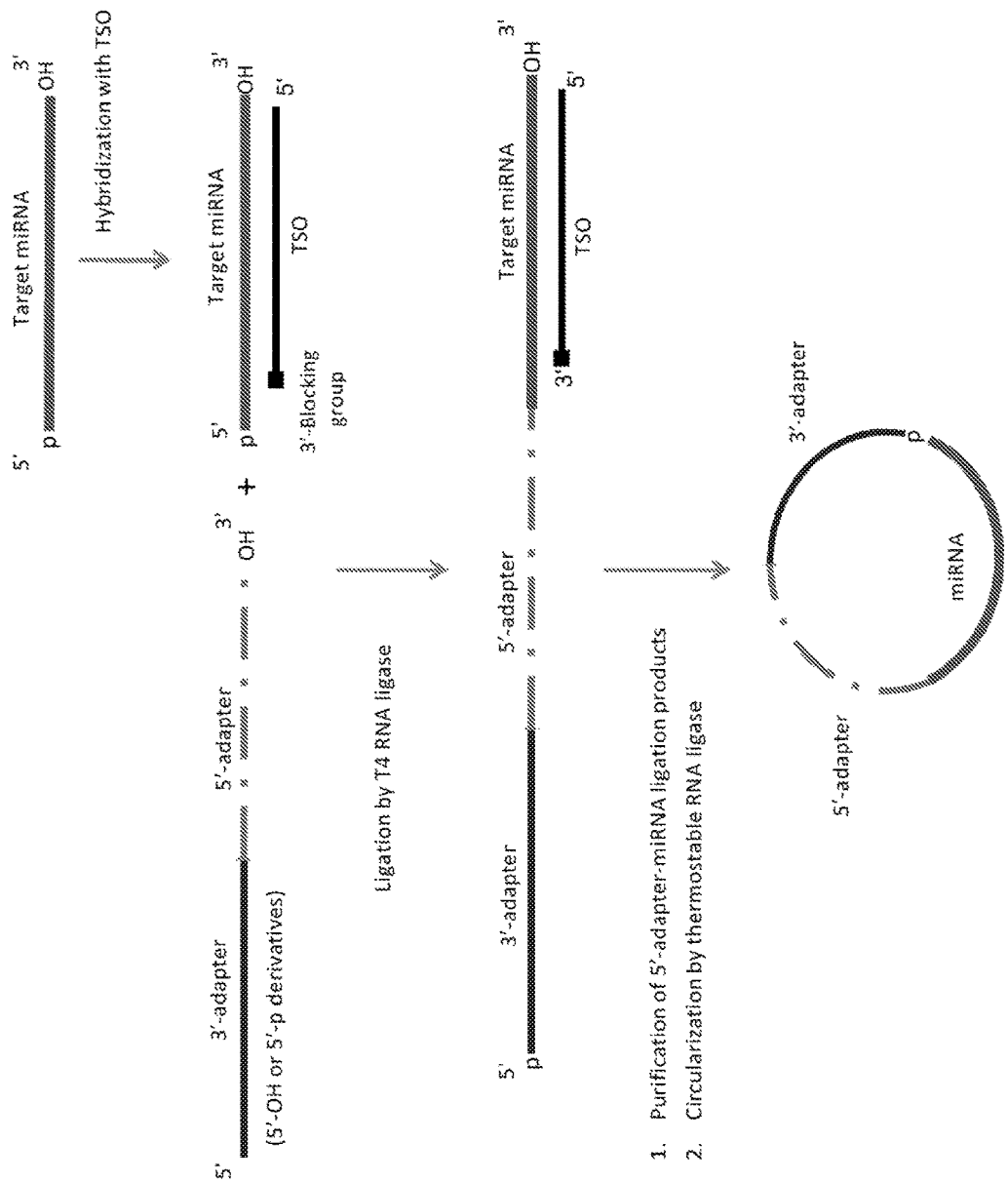
FIG. 10. Scheme of construction of an "miRNA library" comprising hybridization of target miRNAs with a TSO and ligation of a single adapter that encodes both the 3'- and 5'-adapters described in FIGS. 5 to 6 to the 5' end of the miRNA (A); optional circularization of the ligation product and subsequent RT-PCR amplification of the circular ligation product (B).

In other embodiments of this invention, a single 5'-adaper is ligated to miRNAs by Rnl1 in the presence of ATP (FIG. 5B, Step 2.1/+ATP) (see examples in FIGS. 9A and 10A). In some aspects of this invention, the 5'-adapters have one of more of the following features: (a) they encode sequences compatible with direct single-molecule (third-generation) RNA sequencing methods such as HeliScope (Helicos Biosciences); (b) they comprise both 3'-adapter (upstream) and 5'-adapter (downstream) sequences compatible with next-generation (second-generation) sequencing technologies such as Solexa, 454 or SOLiD (see FIG. 10A); (e) they carry single or multiple haptens such as biotin or digoxigenin; (f) they carry single or multiple signal moieties; and/or (g) they encode tag or probe sequences for (sandwich) hybridization with bDNA.

Figure 9B:
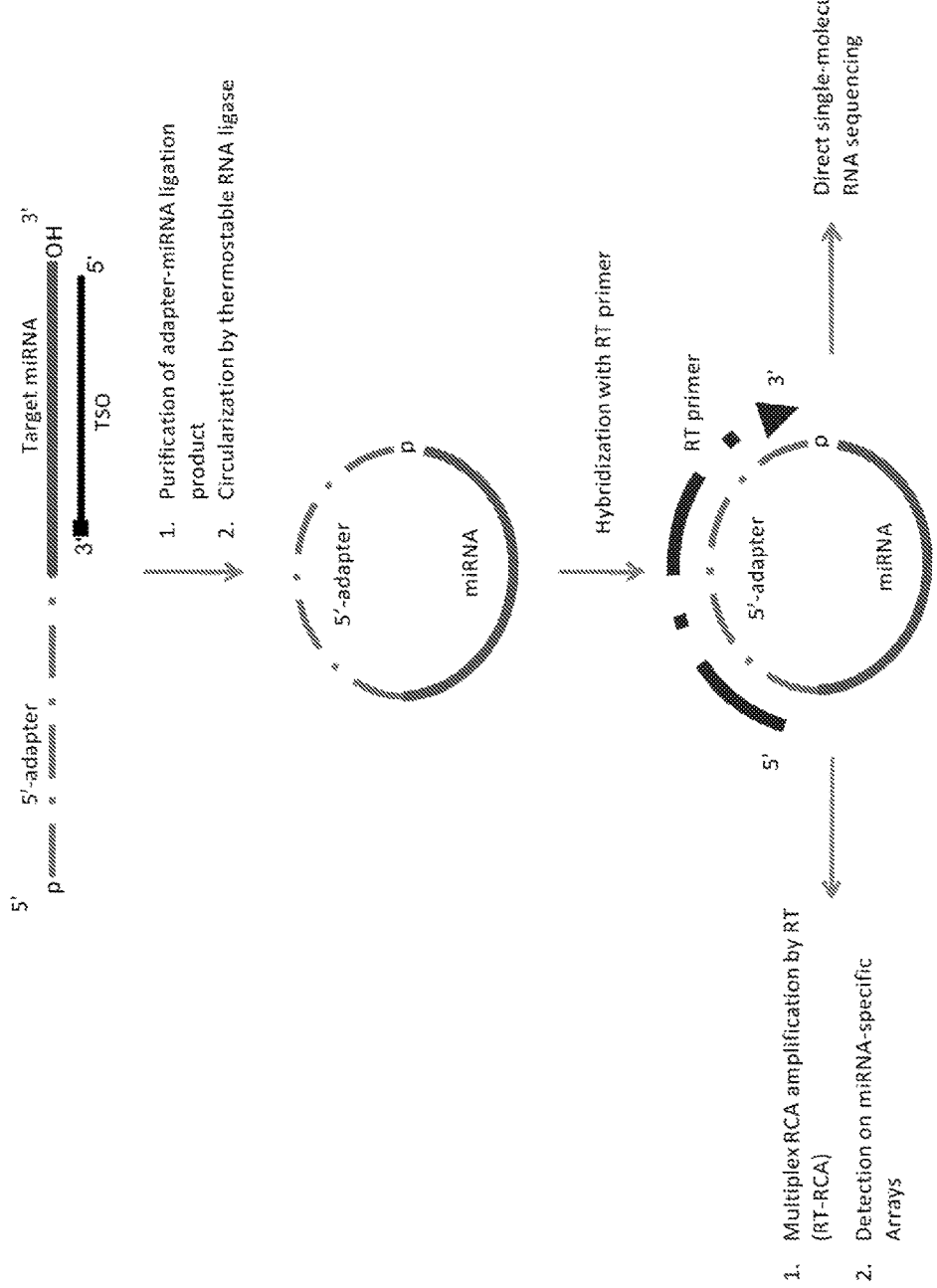

In some aspects of this invention, a single 5'-phosphorylated 5'-adapter (FIGS. 9B and 10A) or 3'-adapter (FIG. 10B) is ligated to the 5' end of miRNAs and the purified ligation product is then circularized by a thermostable bacteriophage RNA ligase homologous to Rnl1 such as CircLigase I or CircLigase II. In some other aspects of this invention, 5'-adapters having 5'-OH are first ligated to the miRNAs, then 5'-phosphorylated by polynucleotide kinase, and then circularized. Purification of 5'-adapter-miRNA ligation products from the excess of 5'-phosphorylated adapters before circularization may be required to separate these products from unwanted/secondary ligation products such as circular adapters or adapter concatamers. In some embodiments of this invention, such purification is performed by gel- or capillary electrophoresis if both adapter ligation and circularization were carried out in solution.

In some embodiments of this invention, Step 1.1 (FIG. 5A) is followed by an additional step (Step 1.1.1) in which the sample is treated by Rnl1 to circularize non-target miRNAs followed (if necessary) by heat inactivation of Rnl1 at 65° C. for 15 min (or by boiling for 2 min) and re-hybridization of target miRNAs with TSO by lowering the temperature, before the ligation of adapters to or extension of target miRNAs.

Figure 10C:
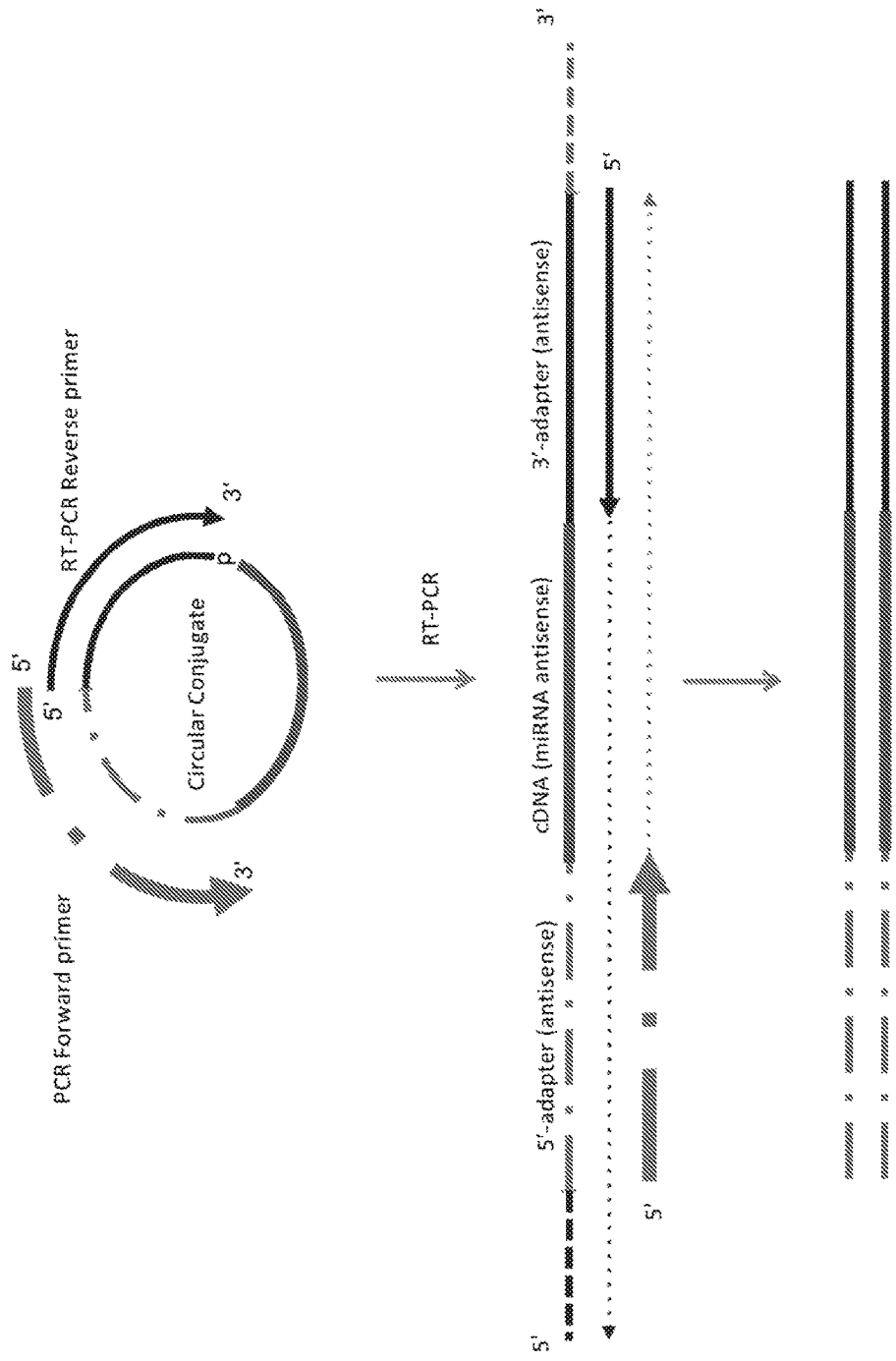

In some other embodiments of the invention, the ligation of adapters to or extension of miRNAs bound to the TSO is followed by reverse transcription (RT) (see examples in FIGS. 5C, 6, 7B and 8B). In some other embodiments of the invention, the circularized ligation products between miRNAs and 5'-adapters are reverse transcribed by an RCA mechanism (RT-RCA) (see examples in FIGS. 9B and 10C). RT-RCA results in multimeric cDNA products comprising tandem repeats of sequences complementary to the target miRNAs together with the adapter or extension sequences.

In some instances, RT primers, which are fully or partially complementary to the adapter or extension sequences, are extended by either an RNA-dependent DNA polymerase (reverse transcriptase) or a DNA-dependent DNA polymerase (DNA polymerase) that can accept DNA and RNA as templates. In some instances, DNA polymerases comprise additional features, thereby minimizing and/or preventing the TSOs hybridized to the target RNA from interfering with the RT primer extension. In some instances, the additional features are selected from a list comprising (a) strand-displacement (helicase) activity allowing displacement of the TSO from the target miRNA in the ligation or extension products; (b) high thermostability, allowing one to perform RT at elevated temperatures that are higher than the melting temperature ($T_m$) of the miRNA-TSO complexes. Examples of appropriate DNA polymerases include but are not limited to: M-MuLV and its mutated versions such SuperScript II and SuperScript III thermostable reverse transcriptases; rTth and Hot Multi-Taq thermostable DNA polymerases; and Klenow Fragment of DNA polymerase I (KF).

In some embodiments of the invention, the RT step is a detection step (e.g., in direct, single-molecule RNA sequencing performed without amplification). In some other embodiments of the invention, the RT step is followed by amplification by PCR (see examples in FIGS. 5C, 6 and 10C). In yet other embodiments of the invention, the RT step consists of an RT-RCAn amplification step followed by detection of the cDNA multimers on arrays (FIG. 10A).

After reverse transcription and before amplification, in some embodiments of the invention the RNA template sequences (miRNA, plus adapters if they are partially or completely RNA) are degraded (see examples in FIGS. 6, 7B and 8B) by one of the following: (a) internal RNase H activity of a reverse transcriptase during the RT; (b) additional RNase H treatment; (c) heating at alkaline pH (pH>10); (d) heating in the presence of metal ions that can degrade RNA such as $Mn^{2+}$, $Zn^{2+}$, or $Pb^{2+}$.

In other embodiments of the invention, the cDNA products of RT are amplified by asymmetric PCR using an excess of any of the forward or reverse PCR primers to produce single stranded amplicons.

With the "solution capture" approach, the intermediate and/or final ligation products, and/or products of reverse transcription, or products of PCR amplification are purified from side/secondary products of these reactions according to the specific size of the products by gel- or capillary-electrophoresis under denaturing conditions following standard protocols for preparation of small RNA sequencing libraries. In other embodiments of this invention, non-denaturing gel-electrophoresis is used to purify duplexes formed by TSO with miRNAs and/or their adapter-ligation or extension products.

In other embodiments of the invention, the "solid-phase capture" function of TSO is exploited. In these embodiments, appropriately modified TSOs (FIGS. 3-4) are immobilized on a solid support and used for affinity capture of miRNA either from total RNA extracts or directly from lysates (cell or tissue), or from bodily fluids. Examples of solid supports include: beads (either non-magnetic or magnetic), membranes, filters, slides, microtiter plates, or microcapillaries made from various materials such as glass/silica, plastic, nitrocellulose, nylon, gold or other metal compounds.

In certain embodiments of this invention, TSOs are immobilized through non-covalent attachment of the modified TSO to a solid support. Examples of modifications that are appropriate for non-covalent immobilization include: (a) a hapten group such as biotin or digoxigenin that is attached to one of the TSO ends or internally, via non-nucleotide or oligonucleotide linkers, and which can bind with high affinity to a surface-bound hapten-specific protein such as streptavidin or a hapten-specific antibody (see examples in FIGS. 3A-C); (b) a 5'- or 3'-end oligonucleotide linker that is complementary to a capture oligonucleotide probe (COP) immobilized on a solid support (see examples in FIGS. 3D-E). In other embodiments of this invention, the modified TSO is immobilized through covalent attachment to an appropriately activated solid-phase material. Examples of TSO modifications appropriate for covalent attachment include anchor groups (such as phosphate, amino or thio) at the ends of non-nucleotide or oligonucleotide linkers that are attached to terminal or internal nucleotides of TSO (see examples in FIGS. 4A-C).

Figure 11A:
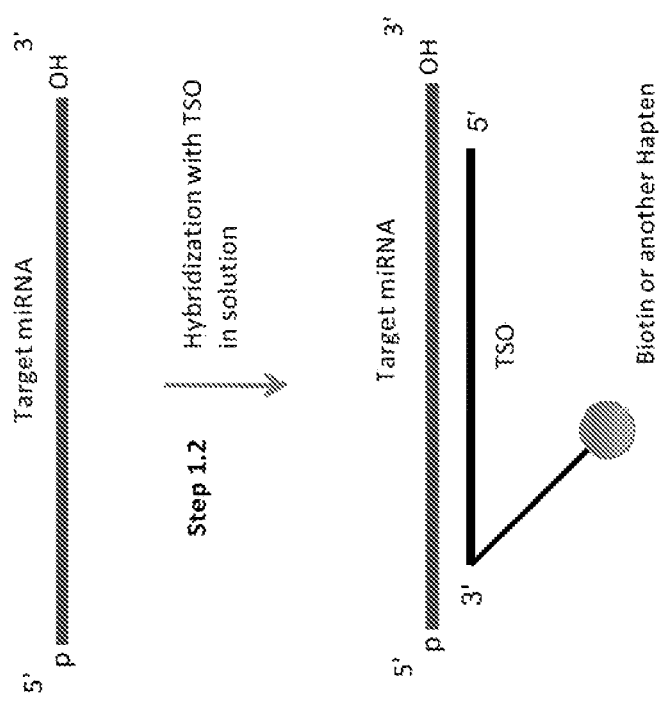
FIG. 11. Scheme of construction of a Solexa- or 454-like "miRNA library" comprising hybridization of target miRNAs with a TSO carrying a hapten group (as described in FIG. 3) in solution (A); sequential ligation of adapters to both ends of miRNAs in solution followed by capture of the final ligation product on a solid phase (B); "solid-phase" reverse transcription and PCR amplification of the released RT products in solution (C).
Figure 11B:
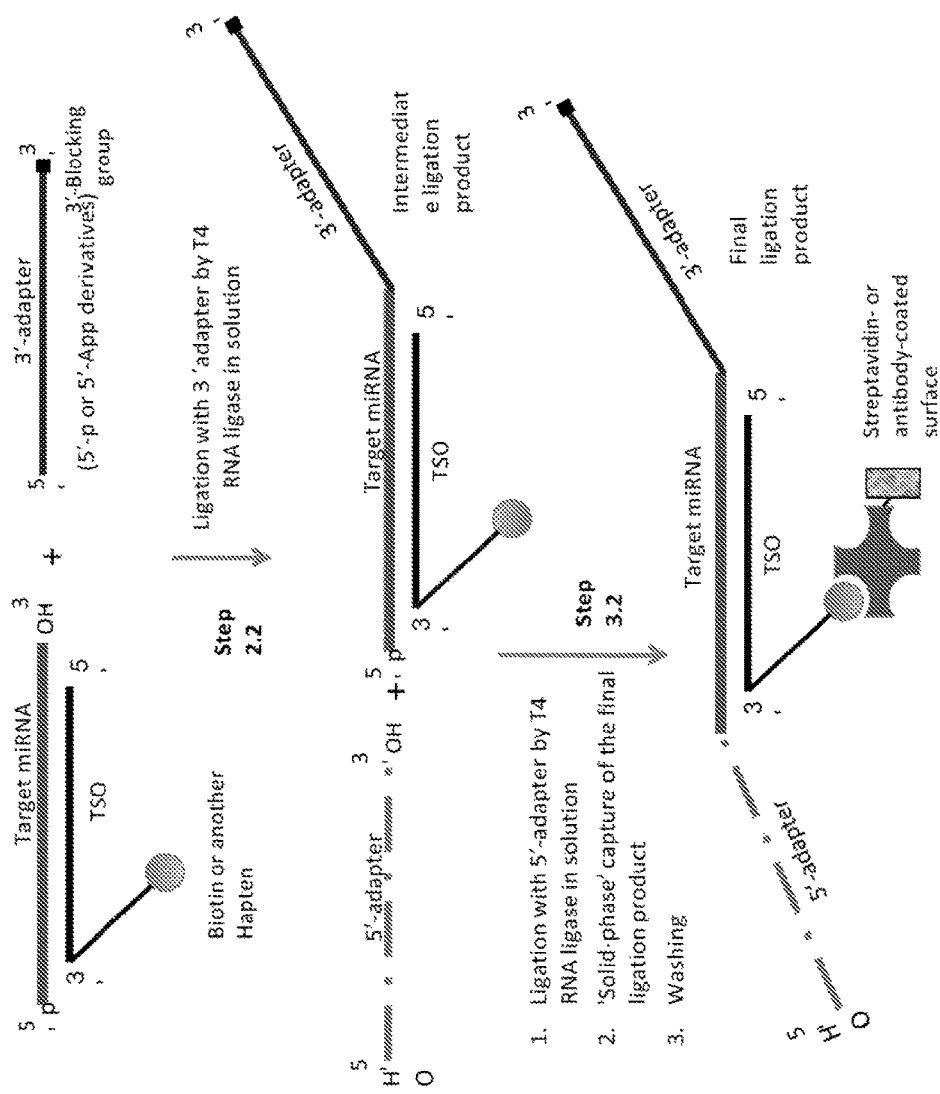
Figure 12A:
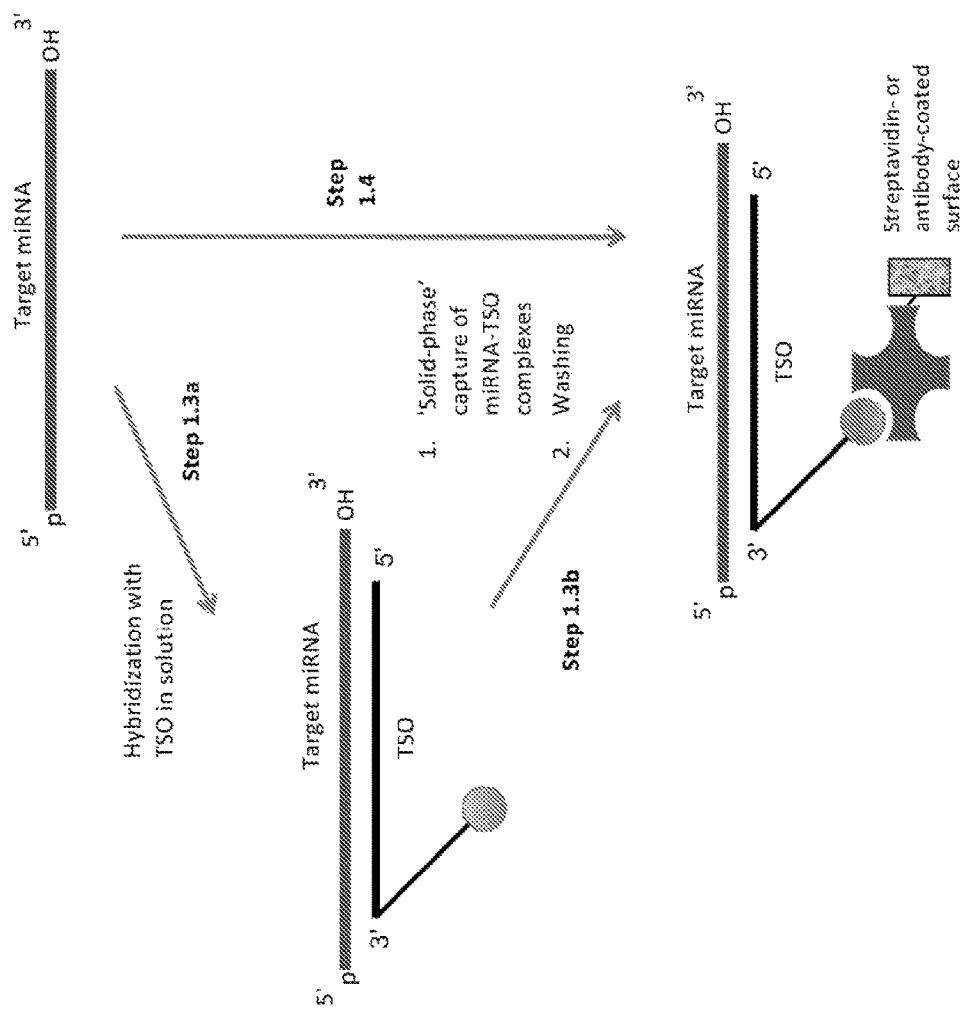
FIG. 12. Scheme of construction of a Solexa- or 454-like "miRNA library" comprising hybridization of target miRNAs with a TSO carrying a hapten group (as described in FIG. 3) either in solution followed by capture of the TSO on a solid support, or hybridization with TSOs already immobilized on a solid support (A); sequential "solid-phase" ligation of adapters to both ends of miRNAs (B). "Solid-phase" reverse transcription and PCR amplification in solution of the resulting released RT products can then be performed as shown in FIG. 11C.

In some embodiments of the invention, TSO are hybridized with miRNAs in solution ("solution hybridization") followed by immobilization on a solid support (Step 1.2, FIG. 11A and Step 1.3a, FIG. 12A). In other embodiments of this invention, both hybridization of miRNAs to a TSO and ligation to adapters and/or extension are performed in solution—similar to the "solution capture approach"—except that the final products of adapter ligation and/or extension are immobilized (or captured) on a solid support (FIG. 11B). Washing of the captured ligation products allows their purification from excess adapters and side products such as adapter dimers (5'-adapter-3'-adapter ligation products) before the RT step.

Figure 12B:
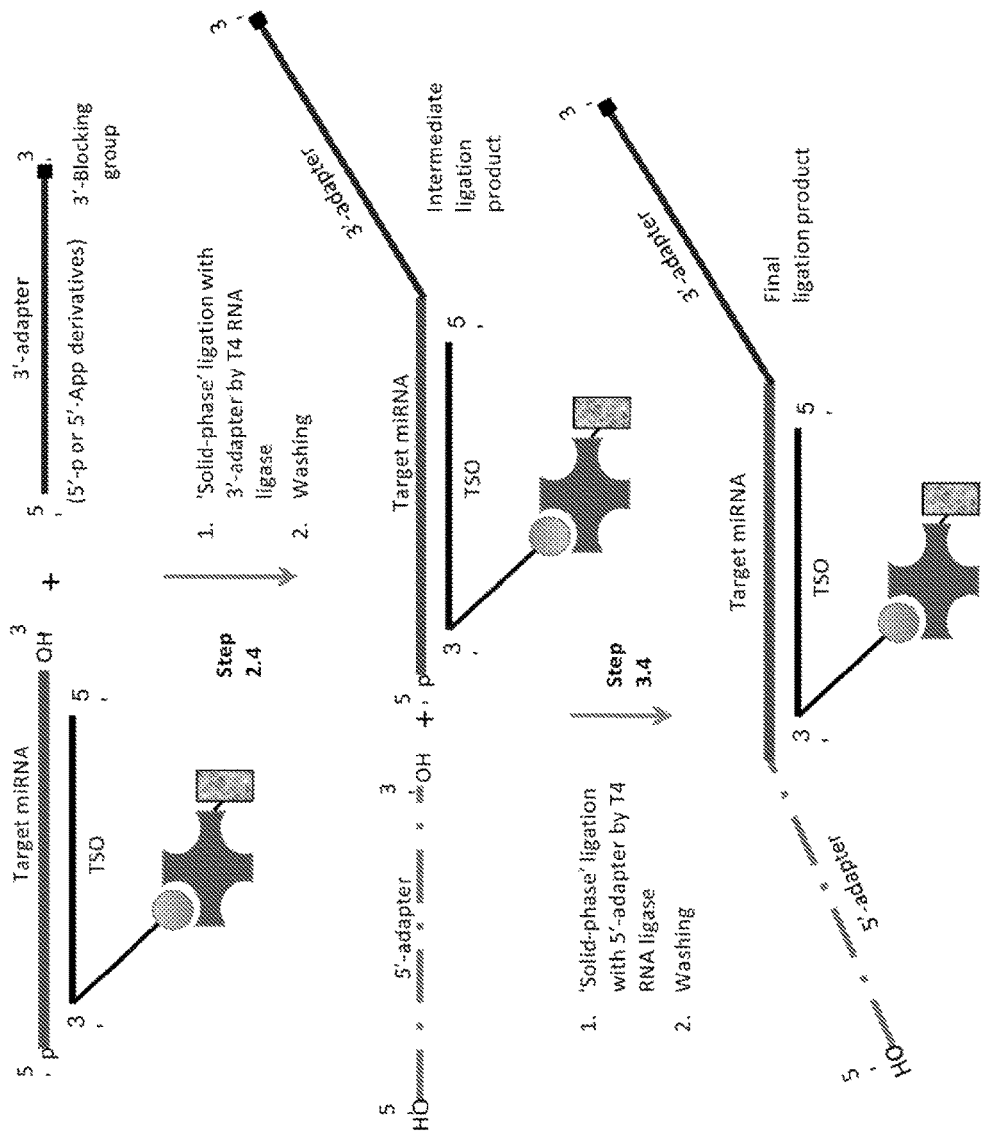
Figure 13A:
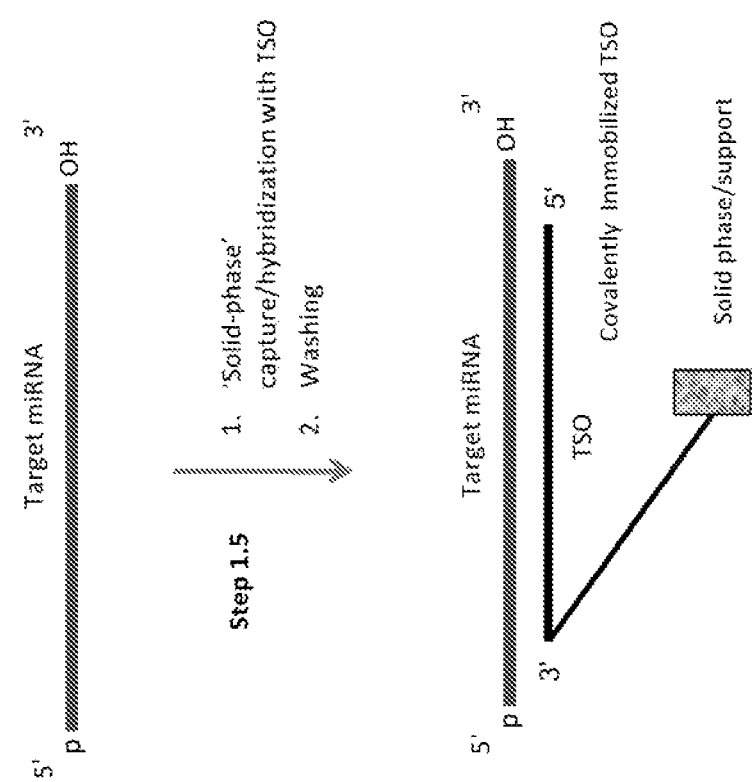
FIG. 13. Scheme of construction of a Solexa- or 454-like "miRNA library" comprising hybridization of target miRNAs with a TSO covalently immobilized on a solid support (see FIG. 4) (A); sequential "solid-phase" ligation of adapters to each end of the miRNAs (B); "solid-phase" reverse transcription and PCR amplification in solution of the resulting released RT products (C).
Figure 13B:
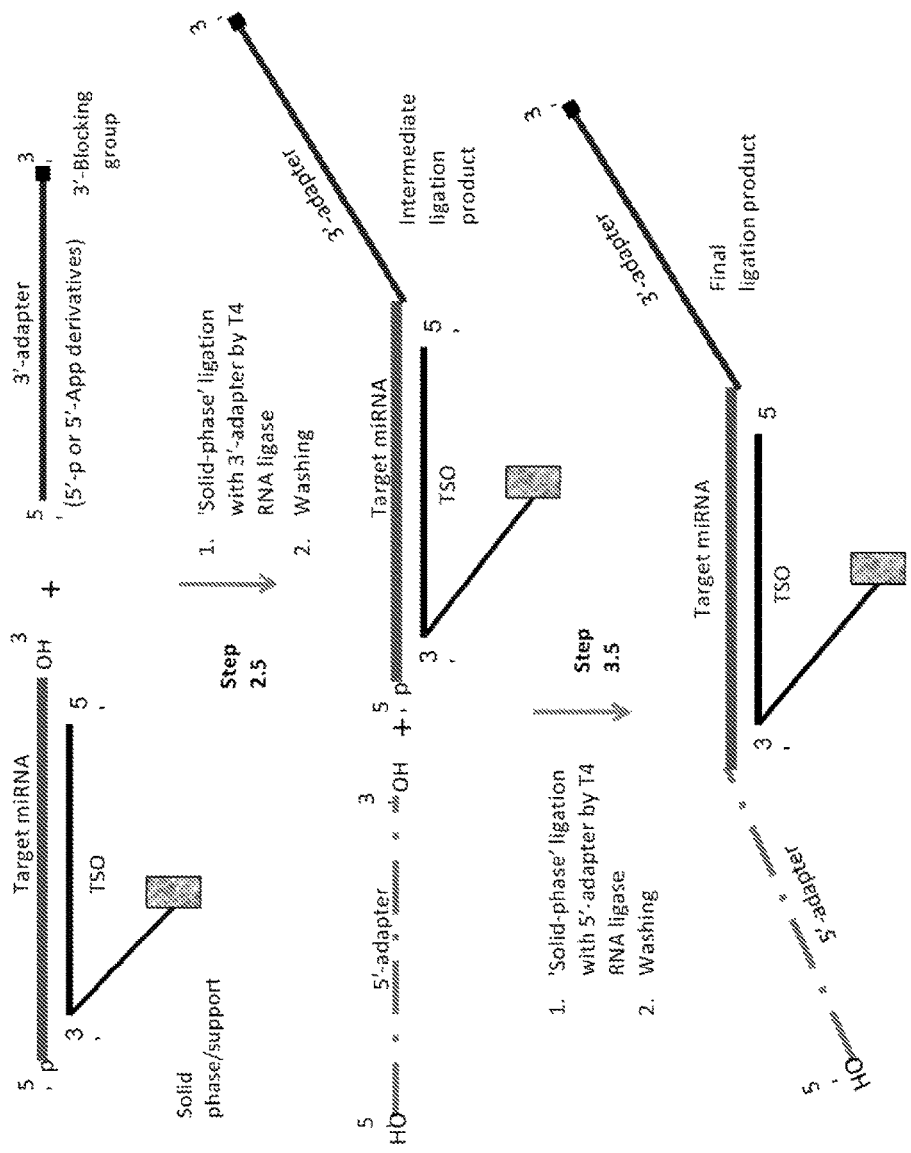

In another embodiment of this invention, miRNAs are directly hybridized with immobilized TSO ("solid-phase hybridization") and washed before subsequent enzymatic steps (FIGS. 12A, 13A). This approach allows "solid-phase"

capture of miRNAs directly from cell or tissue lysates, or from human bodily fluids (such as plasma, serum, saliva, urine)—similar to direct capture of miRNA on arrays. Washing of the captured miRNAs allows their enrichment, concentration, and purification before the next enzymatic steps. The purification step eliminates possible inhibitors of the ligation or extension reactions as well as non-target miRNAs. The captured miRNAs are subjected to "solid-phase" ligation and/or extension reactions (FIGS. 12B, 13B). Washing of the captured ligation products allows their purification from excess of adapters and unwanted/secondary ligation products such as adapter dimers (5'-adapter-3'-adapter ligation products) before the RT step.

Figure 11C:
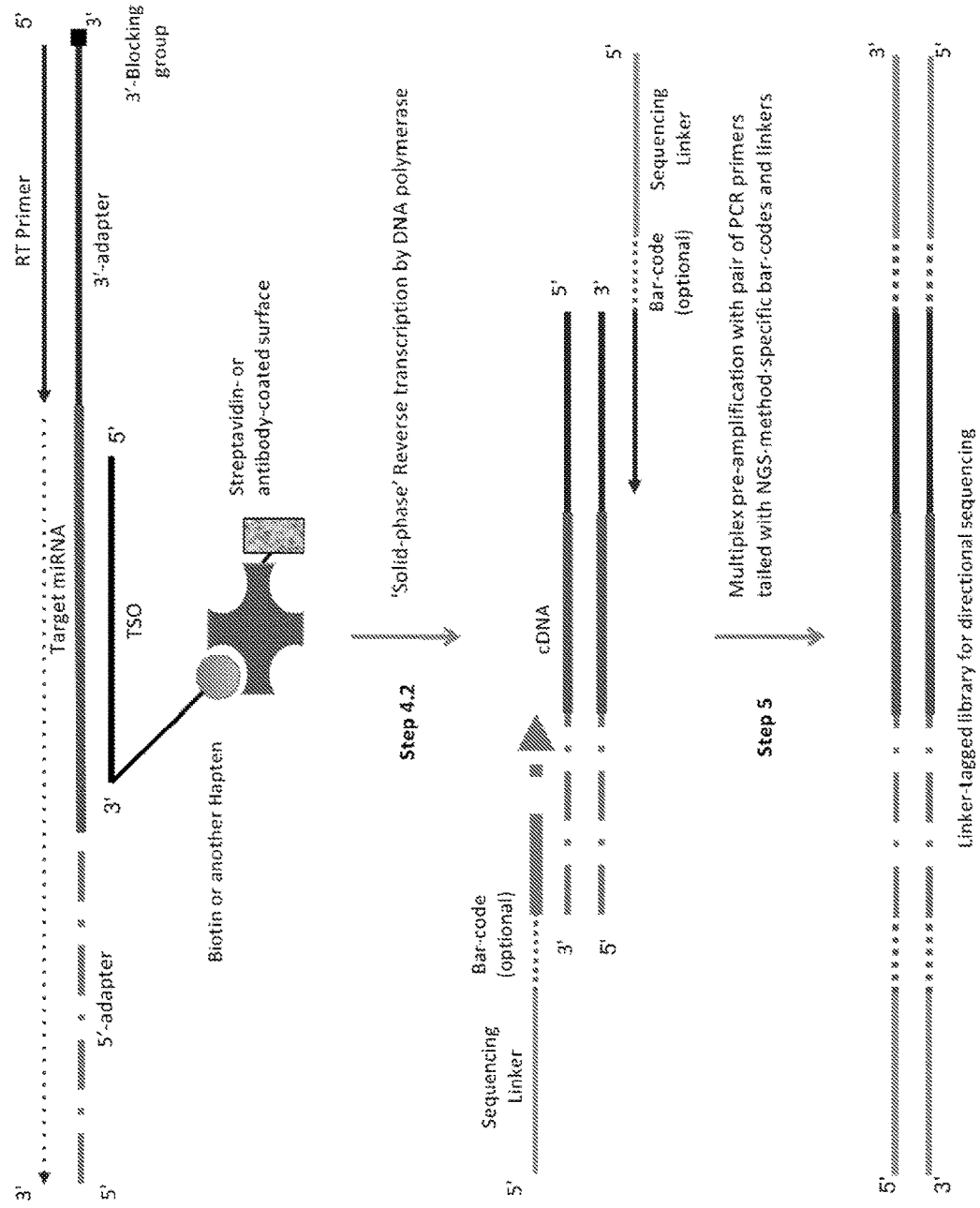
Figure 13C:
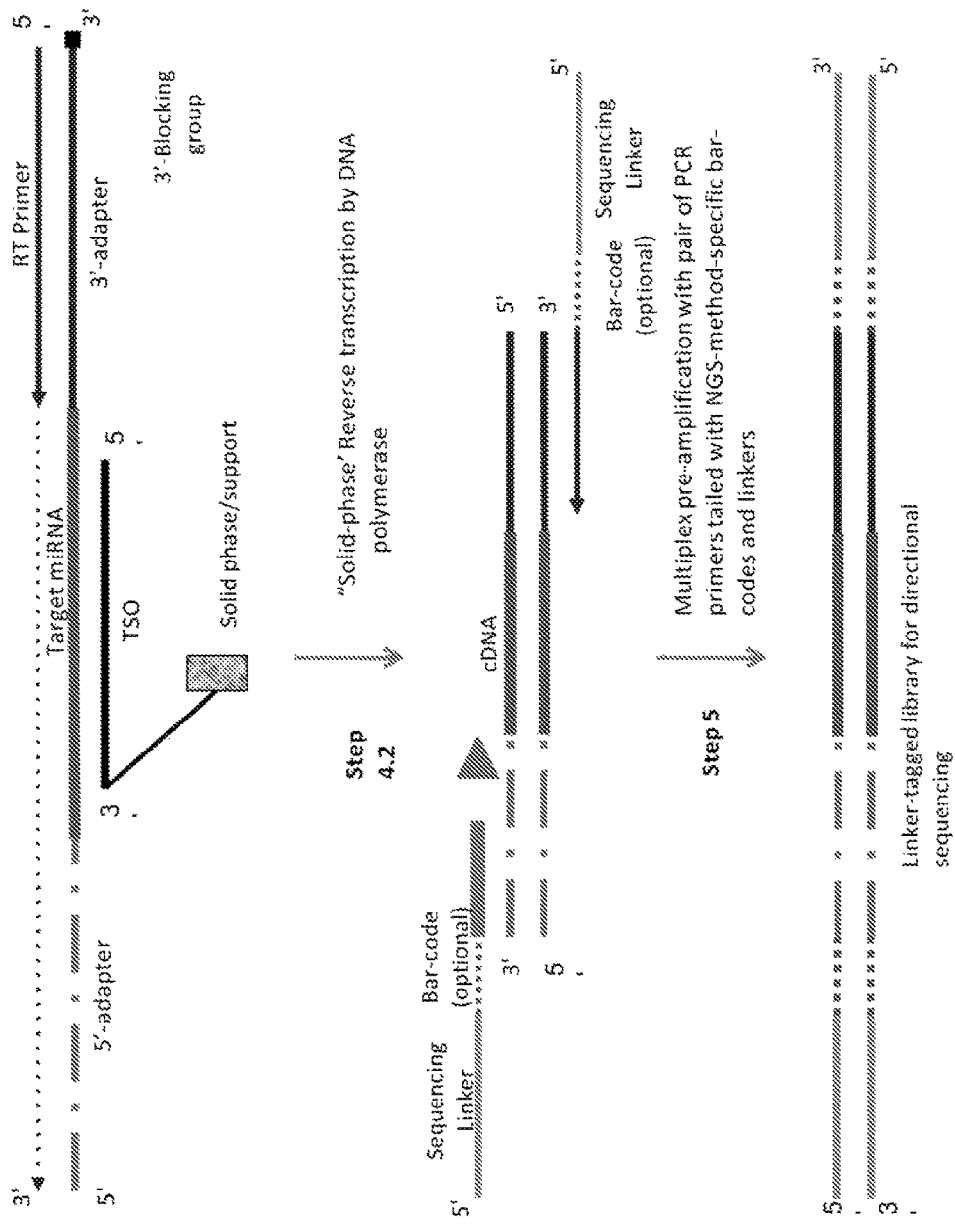

In some embodiments of this invention, the "solid-phase" reverse transcription by DNA polymerase with strand-displacement or 5'-exonuclease activity displaces the TSO and releases the cDNA (products of the primer extension) into solution, whereupon they are amplified by PCR (FIGS. 11C, 13C). In other embodiments of this invention, the ligation or extension products bound to the immobilized TSO are released into solution—e.g., by washing with hot (≥70° C.) $H_2O$ or a low-salt buffer such as 0.1×TE buffer (1 mM Tris-HCl, 0.1 mM EDTA)—and the solution phase is separated from the solid phase before RT or RT-PCR step performed in solution.

In some embodiments of this invention, similar solid-phase formats are applied to the schemes shown in FIGS. 7-10 for capture and purification or enrichment of miRNAs from biological samples or total RNA extracts, which may involve one or more of the following procedures: (a) ligation of a single 3'- or 5'-adapter to miRNAs; (b) extension of miRNAs by nucleotide transferases; (c) circularization of the ligation or extension products; and (d) reverse transcription of the ligation or extension or circularization products. In some embodiments of this invention, the ligation products captured on a solid support are washed to remove excess adapters or unwanted/secondary ligation products such as circular adapters before the RT or detection steps.

Disclosed herein, in some embodiments, is a target-specific oligonucleotide (TSO) for hybridizing a target RNA, wherein (a) the target RNA is a small RNA; and (b) the TSO comprises about 10 nucleotides to about at least 1 fewer nucleotide than the target RNA. In some instances, the target RNA comprises about 15 nucleotides to about 25 nucleotides. In other instances, the target RNA comprises about 17 nucleotides to about 23 nucleotides. Alternatively, the TSO comprises about 13 nucleotides to about 22 nucleotides. The TSO can comprise at least 2 fewer nucleotides than the target RNA. In some instances, the TSO comprises at least 3 fewer nucleotides than the target RNA. In other instances, the TSO comprises at least 4 fewer nucleotides than the target RNA. Alternatively, the TSO comprises at least 5 fewer nucleotides than the target RNA. The TSO can comprise at least 6 fewer nucleotides than the target RNA.

Hybridization of the TSO to the target RNA can produce an overhang on the target RNA. In some instances, the overhang is at the 5' end of the target RNA. In other instances, the overhang is at the 3' end of the target RNA. Alternatively, the overhang is at the 5' end and at the 3' end of the target RNA. In some instances, the overhang is at the 5' end and there is no overhang at the 3' end of the target RNA. In other instances, the overhang is at the 3' end and there is no overhang at the 5' end of the target RNA. The overhang can comprise at least about 1 nucleotide. In some instances, the overhang comprises at least about 2 nucleotides. In other instances, the overhang comprises at least about 3 nucleotides. Alternatively, the overhang comprises at least about 4 nucleotides. The overhang can comprise at least about 5 nucleotides. In some instances, the 5'-overhang comprises about 2 nucleotides and the 3'-overhang comprises about 2 nucleotides. In other instances, the 5'-overhang comprises about 4 nucleotides.

In some instances, the TSO further comprises at least about 1 blocking group. The blocking group can be at the 3' end of the TSO. In some instances, the blocking group is at the 5' end of the TSO. In other instances, the TSO comprises a blocking group at the 3' end of the TSO and a blocking group at the 5' end of the TSO. In some instances, the blocking group is 3'-p, or 3'-amino, or 2',3'-dideoxy nucleoside (ddN), 3'-inverted (3'-3') deoxy nucleoside (idN), or any other modification known in the art that prevents ligation to or extension of the 3' end. The TSO can hybridize to different isoforms and/or isomirs of the target RNA.

In some instances, the sequence of the TSO is at least about 70% complementary to the sequence of the target RNA. In other instances, the sequence of the TSO is at least about 80% complementary to the sequence of the target RNA. Alternatively, the sequence of the TSO is at least about 85% complementary to the sequence of the target RNA. The sequence of the TSO can be at least about 90% complementary to the sequence of the target RNA. In some instances, the sequence of the TSO is at least about 95% complementary to the sequence of the target RNA. In other instances, the sequence of the TSO is at least about 97% complementary to the sequence of the target RNA.

The TSO can comprise RNA, DNA, modified analogs thereof, or combinations thereof. In some instances, the TSO comprises at least about 1 nucleotide that cannot be replicated by a DNA polymerase. In other instances, the TSO comprises at least about 1 nucleotide that cannot be reverse transcribed by a reverse transcriptase. The TSO can comprise one or more hairpins. In some instances, the hairpins cannot be bypassed by a polymerase. In some instances, the polymerase is a reverse transcriptase.

Further disclosed herein, in some embodiments, is a kit comprising: (a) the TSO of any of the above claims; (b) optionally, one or more adapters, and (c) instructions for hybridizing the TSO to a target RNA, wherein the target RNA is a small RNA. In some instances, the target RNA comprises about 15 nucleotides to about 25 nucleotides. In other instances, the target RNA comprises about 17 nucleotides to about 23 nucleotides. The instructions for hybridizing the TSO to the target RNA can comprise instructions for attaching one or more adapters to the target RNA. In some instances, the instructions for hybridizing the TSO to the target RNA comprise instructions for attaching one or more linkers to the target RNA. In other instances, the sequence of the TSO is not complementary to the sequence of the one or more adapters. Alternatively, or additionally, the TSO cannot hybridize to the one or more adapters. In some instances, the sequence of the TSO is not complementary to the sequence of the one or more linkers. In other instances, the TSO cannot hybridize to the one or more linkers. The instructions for hybridizing the TSO to the target RNA can comprise instructions for reverse transcribing and/or amplifying the target RNA. In some instances, reverse transcribing and/or amplifying the target RNA comprises one or more primers. In other instances, the sequence of the TSO is not complementary to the sequence of the one or more primers. In some instances, the TSO cannot hybridize to the one or more primers.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, e.g., any elements developed that perform the same function, regardless of structure. The scope of the present invention, therefore, is not intended to be limited to the exemplary embodiments shown and described herein. Rather, the scope and spirit of the present invention is embodied by the appended claims.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

Example 1

Design miRNA-Specific Probes 63 human (hsa-) miRNAs (Table 1) were selected for designing target-specific oligonucleotides (TSO) probes. These miRNAs are listed in Table 1 and labeled according to the efficiency of detection by Solexa sequencing (Hafner et al. 2011), with bold miRNAs undercounted by factors of 0.001-0.005, italic miRNAs undercounted by factors of 0.01-0.09, and plain font miRNAs undercounted by factors of 0.1-0.6 relative to miRNAs that gave the highest read frequency from an equimolar pool of 770 miRNAs.

TABLE 1

| let-7a | let-7b | let-7c | let-7d | let-7e | let-7g | miR-634 |
|---|---|---|---|---|---|---|
| miR-16 | miR-23a | miR-23b | miR-26a | miR-30c | miR-31 | miR-140-5p |
| miR-34b | miR-92a | miR-92b | miR-96 | miR-99a | miR-100 | miR-199a-3p |
| miR-103 | miR-107 | miR-149 | miR-125b | miR-182 | *miR-141* | *miR-125a-3p* |
| miR-143 | miR-145 | *miR-195* | *miR-181b* | *miR-222* | miR-182* | miR-296-5p |
| miR-183 | miR-184 | miR-210 | *miR-197* | miR-375 | miR-199a-5p | *miR-486-5p* |
| miR-202 | *miR-205* | miR-370 | miR-221 | miR-766 | miR-296-3p | *miR-885-5p* |
| miR-622 | miR-328 | miR-498 | *miR-373* | miR-640 | *miR-485-3p* | miR-574-3p |
| *miR-877* | miR-497 | miR-636 | miR-503 | miR-888 | miR-518a-3p | miR-524-5p |

The miRNA sequences are available at the miRBase site (www.mirbase.org). Target-specific oligodeoxynucleotide probes (TSOs) were designed for each miRNA such that, when hybridized together form TSO-miRNA duplexes, the ends of the miRNAs overhang their respective probes by 0, or 1, or 2, or 3, or 4 nt at each 5'- and/or 3'-end with various combinations of the overhang lengths. These combinations include: [1+0], [1+1], [1+2], [1+3], [1+4]; [2+0], [2+1], [2+2], [2+3], [2+4]; [3+0], [3+1], [3+2], [3+3], [3+4]; [4+0], [4+1], [4+2], [4+3], [4+4], wherein the first and second numbers correspond to the overhang length at the 5'-end and the 3'-end of the miRNAs, respectively. The length of the TSO is kept shorter than the length of target miRNAs by at least 1 nt.

Example 2

"Solid-Phase Capture" of miRNAs by the TSO Probes

For this purpose, miRNAs of the miRXplore Universal Reference pool (Miltenyi Biotec) containing equimolar amounts of 954 synthetic miRNAs, including the 63 miRNAs from Example 1, are 5'-$^{32}$P-labeled by polynucleotide kinase, and then used for multiplex hybridization with a molar excess of the TSO probes. TSO probes specific to the selected miRNAs of a given overhang length (when hybridized to their cognate miRNAs) are pooled, and each TSO pool is hybridized to the miRNA pool. Streptavidin-coated magnetic beads are added to the tube and a magnetic rack (NEB) is used to capture the target miRNAs hybridized to the biotinylated TSOs. The captured miRNAs are washed under conditions providing stability to the immobilized hybrids while allowing all unrelated miRNA species to be washed away (such as at 25° C. by buffer containing 100 mM NaCl, 1 mM EDTA, 40 mM Tris-HCl, pH7.5). The captured miRNAs are then released into solution by heating at 70-95° C. in the presence of 0.1×TE buffer (1 mM Tris-HCl, 0.1 mM EDTA, pH 7 in nuclease-free, ultrapure water) or deionized, nuclease-free water.

Example 3

Ligation of Adapters in Solution

In this example, 3'-adapters comprising SEQ ID NO:1 (pUCGUAUGCCGUCUUCUGCUUGUidT (5'-phosphate form)), or (AppUCGUAUGCCGUCUUCUGCUUGUidT (5'-adenylated form)), where idT is inverted deoxythymidine used to block the 3'-end), are used together with the 5'-adapter comprising SEQ ID NO:2 (GUUCAGAGUUC-UACAGUCCGACGAUC). These standard adapters, commercially available from the Illumina Small RNA Sample Prep protocol (v.1.5), are sequentially ligated in solution to $^{32}$P-labeled miRNAs (from Example 2) that are either free or pre-hybridized to the TSOs. These ligation reactions are performed in the presence or absence of ATP for the 5'-phosphate or 5'-adenylated forms of the 3'-adapter, respectively. For 3'-adapter ligation, the following RNA ligases can be used: Rnl1, Rnl2(1-249), or Rnl2(1-249)K227Q (NEB). These ligases can be used individually or in all pairs of two ligases as a possible approach to balancing out their biases. Rnl1 is used for 5'-adapter ligation. The obtained $^{32}$P-labeled miRNA ligation products are analyzed by denaturing PAGE using a phosphorimager. The improvement in ligation efficiency resulting from pre-hybridizing the miRNAs with complementary TSOs can be seen by comparing the relative amounts of adapter-miRNA ligation products, and unligated or circularized miRNAs. With optimized TSOs, ligation bias for miRNAs pre-hybridized to the TSOs is expected to be greatly reduced (e.g. by at least about 70% to about 90-95%).

Example 4

Ligation of Adapters on a Solid Support

In this Example, we use the $^{32}$P-labeled miRNAs captured on beads from Example 2. The 3'-adapter and 5'-adapter are sequentially ligated to the captured miRNAs as described in Example 3, except that after ligating each adapter to the captured miRNAs, the beads are washed to remove the unligated adapter species and other components of the ligation reaction while keeping the adapter-miRNA ligation products captured on the immobilized TSOs. After both 3'-adapter and 5'-adapter have been ligated, the final ligation products are released into solution and then analyzed by denaturing PAGE.

This procedure can be used to select TSO designs providing the optimal yield of the final ligation products for each target miRNA are selected for both the solution- and solid-phase ligation approaches.

Example 5

RT-PCR of 5'-Adapter-miRNA-3'-Adapter Ligation Products

The final ligation products from Example 4 are released into solution and then reverse transcribed using the DNA primer comprising SEQ ID NO: 3 (CAAGCAGAAGACG-GCATACGA) (Illumina). This can be done either in the presence or absence of beads carrying immobilized TSOs. If TSOs are present, to reduce or prevent TSO interference with RT, reverse transcriptases having strand-displacement activity (e.g., M-MuLV from NEB, SuperScript II and SuperScript III from Life Technologies) or rTth DNA Polymerase, which has both RT and 5'-exonuclease activity (Life Technologies) can be used. Since rTth and SuperScript III polymerases are thermostable enzymes, they can be used at temperatures above the $T_m$s of the TSO-miRNA duplexes. Reverse transcription may also be performed in "solid-phase" where the final ligation products from Example 4 are not released into solution phase before reverse transcription.

The RT products accumulated in the solution phase are amplified by PCR either in the presence of the magnetic beads or after separation of the solution phase from the beads. Ten or twelve cycles of PCR are run using Phusion DNA Polymerase (Thermo Scientific) according to the standard Small RNA Sample Prep protocol (Illumina) with the forward PCR primer (SEQ ID NO: 4: AATGATACGGC-GACCACCGACAGGTTCAGAGTTCTACAGTCCGA) and reverse PCR primer (SEQ ID NO: 5: CAAGCA-GAAGACGGCATACGA). The size and yields of PCR amplicons can be analyzed by non-denaturing PAGE, which can reveal possible secondary products, such as amplicons that lack miRNA inserts or have longer than expected inserts (e.g., miRNA concatamers or pre-miRNAs).

Example 6

Preparation and Sequencing of Custom miRNA Libraries

In this example, custom miRNA libraries were prepared using Library 1-8 preparation protocols as disclosed herein. These libraries were sequenced using the Illumina's small RNA sequencing primer (SEQ ID NO: 6: CGACAGGT-TCAGAGTTCTACAGTCCGACGATC) and the absolute and relative miRNA copy numbers were compared. In this experiment, we used a universal miRNA pool, miRXplore Universal Reference (Miltenyi Biotec), which contains equimolar amounts of 954 synthetic miRNAs (as in Example 2). Because of adapter ligation bias, the relative copy numbers of miRNAs in synthetic pools determined by Illumina sequencing have been found to vary up to 10,000-fold despite equimolar representation in the original pool (Linsen et al. 2009; Hafner et al. 2011). Library 1-8 preparation protocols were used in this Example. The library preparation protocols can vary by including pre-hybridization of the selected miRNAs with complementary TSOs before the ligation of adapters. In some library preparation protocols, the TSOs and the ligation reagents are added simultaneously to the reaction mixture. The pre-hybridization (or pre-annealing) of TSOs to miRNAs can reduce the ligation biases for the selected miRNAs. Preferably, addition of the TSOs does not affect other miRNAs present in the universal pool.

In this example we used the smaller pool of 15 miRNAs representing all three groups from Example 1 as shown in Table 2.

TABLE 2

| hsa-miRNA | miRBase ID | Sequence (5'-3') | SEQ ID NO |
|---|---|---|---|
| miR-296-5p | MIMAT0000690 | AGGGCCCCCCCUCAAUC CUGU | 7 |

TABLE 2-continued

| hsa-miRNA | miRBase ID | Sequence (5'-3') | SEQ ID NO |
|---|---|---|---|
| miR-328 | MIMAT0000752 | CUGGCCCUCUCUGCCCUUCCGU | 8 |
| miR-31-5p | MIMAT0000089 | AGGCAAGAUGCUGGCAUAGCU | 9 |
| miR-145-5p | MIMAT0000437 | GUCCAGUUUUCCCAGGAAUCCCU | 10 |
| miR-524-5p | MIMAT0002849 | CUACAAAGGGAAGCACUUUCUC | 11 |
| miR-16-5p | MIMAT0000069 | UAGCAGCACGUAAAUAUUGGCG | 12 |
| miR-96-5p | MIMAT0000095 | UUUGGCACUAGCACAUUUUUGCU | 13 |
| miR-497-5p | MIMAT0002820 | CAGCAGCACACUGUGGUUUGU | 14 |
| miR-498 | MIMAT0002824 | UUUCAAGCCAGGGGCGUUUUUC | 15 |
| miR-636 | MIMAT0003306 | UGUGCUUGCUCGUCCCGCCCGCA | 16 |
| miR-125b-5p | MIMAT0000423 | UCCCUGAGACCCUAACUUGUGA | 17 |
| miR-182-5p | MIMAT0000259 | UUUGGCAAUGGUAGAACUCACACU | 18 |
| miR-199a-5p | MIMAT0000231 | CCCAGUGUUCAGACUACCUGUUC | 19 |
| miR-634 | MIMAT0003304 | AACCAGCACCCCAACUUUGGAC | 20 |
| miR-140-5p | MIMAT0000431 | CAGUGGUUUUACCCUAUGGUAG | 21 |

Here we used two designs of TSO probes: (i) [2+2], and (ii) [4+0], where the two numbers in brackets correspond respectively to the length of the single-stranded overhangs (in nucleotides, nt) at the 5' and 3' ends of the miRNAs, formed upon hybridization with the TSO. The synthetic TSO probes (IDT) had biotin residues (3BioTeg) at their 3'-ends, which can serve to block extension by a polymerase and/or can serve as a hook for capture by streptavidin-coated beads. All reactions were carried out in solution. The TSO sequences are shown in Table 3:

TABLE 3

| miRNA [1] | TSO sequences (5'-3') | SEQ ID NO | Overhang design [2] | $T_m$ [3] |
|---|---|---|---|---|
| hsa-miR-296-5p | ACAGGATTGAGGGGGGG | 22 | [4 + 0] | 52.8° C. |
| | AGGATTGAGGGGGGGCC | 23 | [2 + 2] | 60.0° C. |
| hsa-miR-328 | ACGGAAGGGCAGAGAGGG | 24 | [4 + 0] | 51.8° C. |
| | GGAAGGGCAGAGAGGGCC | 25 | [2 + 2] | 59.5° C. |
| hsa-miR-31-5p | AGCTATGCCAGCATCTT | 26 | [4 + 0] | 52.9° C. |
| | CTATGCCAGCATCTTGC | 27 | [2 + 2] | 52.8° C. |
| hsa-miR-145-5p | AGGGATTCCTGGGAAAACT | 28 | [4 + 0] | 46.1° C. |
| | GGATTCCTGGGAAAACTGG | 29 | [2 + 2] | 46.2° C. |
| hsa-miR-524-5p | GAGAAAGTGCTTCCCTTT | 30 | [4 + 0] | 48.6° C. |
| | GAAAGTGCTTCCCTTTGT | 31 | [2 + 2] | 50.1° C. |

TABLE 3-continued

| miRNA [1] | TSO sequences (5'-3') | SEQ ID NO | Overhang design [2] | $T_m$ [3] |
|---|---|---|---|---|
| hsa-miR-125b-5p | TCACAAGTTAGGGTCTCA | 32 | [4 + 0] | 48.8° C. |
| | ACAAGTTAGGGTCTCAGG | 33 | [2 + 2] | 49.2° C. |
| hsa-miR-182-5p | AGTGTGAGTTCTACCATTGC | 34 | [4 + 0] | 53.7° C. |
| | TGTGAGTTCTACCATTGCCA | 35 | [2 + 2] | 54.8° C. |
| hsa-miR-199a-5p | GAACAGGTAGTCTGAACAC | 36 | [4 + 0] | 43.9° C. |
| | ACAGGTAGTCTGAACACTG | 37 | [2 + 2] | 46.5° C. |
| hsa-miR-634 | GTCCAAAGTTGGGGTGCT | 38 | [4 + 0] | 55.3° C. |
| | CCAAAGTTGGGGTGCTGG | 39 | [2 + 2] | 53.2° C. |
| hsa-miR-140-5p | CTACCATAGGGTAAAACC | 40 | [4 + 0] | 41.4° C. |
| | ACCATAGGGTAAAACCAC | 41 | [2 + 2] | 41.8° C. |
| hsa-miR-16-5p | CGCCAATATTTACGTGCT | 42 | [4 + 0] | 45.8° C. |
| | CCAATATTTACGTGCTGC | 43 | [2 + 2] | 45.3° C. |
| hsa-miR-96-5p | AGCAAAAATGTGCTAGTGC | 44 | [4 + 0] | 42.4° C. |
| | CAAAAATGTGCTAGTGCCA | 45 | [2 + 2] | 43.1° C. |
| hsa-miR-497-5p | ACAAACCACAGTGTGCT | 46 | [4 + 0] | 45.4° C. |
| | AAACCACAGTGTGCTGC | 47 | [2 + 2] | 48.1° C. |
| hsa-miR-498 | GAAAAACGCCCCCTGGCTT | 48 | [4 + 0] | 52.6° C. |
| | AAAACGCCCCCTGGCTTGA | 49 | [2 + 2] | 54.3° C. |
| hsa-miR-636 | TGCGGGCGGGACGAGCAAG | 50 | [4 + 0] | 56.1° C. |
| | CGGGCGGGACGAGCAAGCA | 51 | [2 + 2] | 57.2° C. |

Notes to Table 3: (1)—see miRNA sequences in Table 2; (2) the two numbers in brackets correspond respectively to the length of the single-stranded overhangs (in nucleotides, nt) at the 5' and 3' ends of the miRNAs, formed upon hybridization with the TSO; (3) $T_m$ for TSO-miRNA duplexes was calculated using a previously described method (Lesnik and Freier 1995).

Control sequencing libraries were prepared as described in the Library 1 (L1) Preparation Protocol (described below). Briefly, this protocol involves mixing the input RNA with the pre-adenylated 3'-adapter, RA3 (SEQ ID NO:52: AppTGGAATTCTCGGGTGCCAAGG), heating to 70° C. for 2 min, chilling on ice then performing ligation using T4 RNA ligase 2 truncated (Rnl2 truncated) in the absence of ATP, followed by ligation with the 5'-adapter, RA5 (SEQ ID NO: 3: GUUCAGAGUUCUACAGUCCGACGAUC) using T4 RNA ligase 1 (Rnl1) in the presence of ATP. The final ligation products are reverse transcribed using the RT primer, RTP (SEQ ID NO: 53: GCCTTGGCACCCGA-GAATTCCA), and then PCR amplified using the universal forward PCR primer and a bar-coded (indexed) reverse PCR primer (RPI) to distinguish the different libraries in cases where they have been pooled together. The sequence information for these primers is available from Illumina. PCR amplicons of the appropriate size (about 147 bp for miRNAs of 21-22 nt) are gel-purified before the Illumina sequencing.

In the miR-ABLE protocols, we pre-hybridized TSO probes of either [2+2] or [4+0] designs with the universal miRNA pool (see L2, L3, L5-L8 preparation protocols). Hybridization of TSOs with the miRNA pool can be done either before adding to the ligation reaction mixture or by simultaneously adding the TSOs and miRNAs into the ligation reaction.

Eight custom sequencing libraries (L1-8) were prepared by the following procedures:

Library 1 (L1) Preparation Protocol

Step 1. Ligate 3'- and 5'-Adapters

Sequential ligation of the RNA 3' and RNA 5' RNA adapters to the sample.

Reagents

Ligation Buffer (HML)
10 mM ATP
RNA 3'-adapter (RA3)
RNA 5'-adapter (RA5)
RNase Inhibitor
T4 RNA Ligase
Ultra Pure Water
T4 RNA Ligase 2, Deletion Mutant Step 1, Part A. Ligate 3'-Adapter 1. Pre-heat the thermal cycler to 70° C. and choose the thermal cycler pre-heat lid option and set to 100° C.

2. Set up the ligation reaction in a sterile, nuclease-free 200 µl PCR tube on ice using Table 4:

TABLE 4

| Reagent | Volume (µl) |
| --- | --- |
| RNA 3'-Adapter (RA3) | 1 |
| 1 µg Total RNA in Nuclease-free Water | 5 |
| Total Volume | 6 |

3. Gently pipette the entire volume up and down 6-8 times to mix thoroughly, then centrifuge briefly.

4. Place the tube on the pre-heated thermal cycler. Close the lid and incubate the tube at 70° C. for 2 minutes and then immediately place the tube on ice.

5. Pre-heat the thermal cycler to 28° C.

6. Prepare the following mix in a separate, sterile, nuclease-free 200 µl PCR tube on ice. Multiply each reagent volume by the number of samples being prepared. Make 10% extra reagent if preparing multiple samples.

TABLE 5

| Reagent | Reagent Volume (µl) |
| --- | --- |
| Ligation Buffer (HML) | 2 |
| RNase Inhibitor | 1 |
| T4 RNA Ligase 2, Deletion Mutant | 1 |
| Total Volume per Sample | 4 |

7. Gently pipette the entire volume up and down 6-8 times to mix thoroughly, then centrifuge briefly.

8. Add 4 µl of the mix to the reaction tube from step 2 and gently pipette the entire volume up and down 6-8 times to mix thoroughly. The total volume of the reaction should be 10 µl.

9. Place the tube on the pre-heated thermal cycler. Close the lid and incubate the tube at 28° C. for 1 hour.

10. With the reaction tube remaining on the thermal cycler, add 1 µl Stop Solution (STP) and gently pipette the entire volume up and down 6-8 times to mix thoroughly. Continue to incubate the reaction tube on the thermal cycler at 28° C. for 15 minutes and then place the tube on ice.

Step 1, Part B. Ligate 5'-Adapter

1. Pre-heat the thermal cycler to 70° C.

2. Aliquot 1.1×N µl of the RNA 5'-adapter (RA5) into a separate, nuclease-free 200 µl PCR tube, with N equal to the number of samples being processed for the current experiment.

3. Place the PCR tube on the pre-heated thermal cycler. Close the lid and incubate the tube at 70° C. for 2 minutes and then immediately place the tube on ice.

4. Pre-heat the thermal cycler to 28° C.

5. Add 1.1×N µl of 10 mM ATP to the aliquoted RNA 5'-adapter tube, with N equal to the number of samples being processed for the current experiment. Gently pipette the entire volume up and down 6-8 times to mix thoroughly.

6. Add 1.1×N µl of T4 RNA Ligase to the aliquoted RNA 5'-adapter tube, with N equal to the number of samples being processed for the current experiment. Gently pipette the entire volume up and down 6-8 times to mix thoroughly.

7. Add 3 µl of the mix from the aliquoted RNA 5'-adapter tube to the reaction from step 10 of Ligate 3'-Adapter. Gently pipette the entire volume up and down 6-8 times to mix thoroughly. The total volume of the reaction should now be 14 µl.

8. Place the tube on the pre-heated thermal cycler. Close the lid and incubate the reaction tube at 28° C. for 1 hour and then place the tube on ice.

Step 2. Reverse Transcribe and Amplify

Reverse transcription followed by PCR is used to create cDNA constructs based on the small RNA ligated with 3' and 5'-adapters. This process selectively enriches those fragments that have adapter molecules on both ends. PCR is performed with two primers that anneal to the ends of the adapters.

Reagents 25 mM dNTP Mix
PCR Mix (PML)
RNA PCR Primer (RP1)
RNA PCR Primer Index (1-48) (RPI1-RPI48) (1 tube of each, depending on the RNA PCR Primer Indices being used)
RNA RT Primer (RTP)
RNase Inhibitor
Ultra Pure Water
5' and 3'-adapter-ligated RNA (6 µl)
5× First Strand Buffer
100 mM DTT
High Sensitivity DNA Chip
SuperScript II Reverse Transcriptase Step 2, Part A. Dilute 25 mM dNTP Mix 1. Pre-heat the thermal cycler to 70° C. and choose the thermal cycler pre-heat lid option and set to 100° C.

2. Dilute the 25 mM dNTPs by premixing the following reagents in a separate, sterile, nuclease-free, 200 µl PCR tube. Multiply each reagent volume by the number of samples being prepared. Make 10% extra reagent if you are preparing multiple samples.

TABLE 6

| Reagent | Volume (µl) |
| --- | --- |
| 25 mM dNTP mix | 0.5 |
| Ultra Pure Water | 0.5 |
| Total Volume | 1.0 |

3. Gently pipette the entire volume up and down 6-8 times to mix thoroughly, then centrifuge briefly.

4. Label the tube "12.5 mM dNTP Mix" and then place it on ice.

Step 2, Part B. Perform Reverse Transcription
1. Combine the following in a separate, sterile, nuclease-free, 200 µl PCR tube.

TABLE 7

| Reagent | Volume (µl) |
| --- | --- |
| 5' and 3'-adapter-ligated RNA | 6 |
| RNA RT Primer (RTP) | 1 |
| Total Volume | 7 |

2. Gently pipette the entire volume up and down 6-8 times to mix thoroughly, then centrifuge briefly.
3. Place the tube on the pre-heated thermal cycler. Close the lid and incubate the tube at 70° C. for 2 minutes and then immediately place the tube on ice.
4. Pre-heat the thermal cycler to 50° C.
5. Prepare the following mix in a separate, sterile, nuclease-free, 200-µl PCR tube placed on ice. Multiply each reagent volume by the number of samples being prepared. Make 10% extra reagent if you are preparing multiple samples.

TABLE 8

| Reagent | Volume (µl) |
| --- | --- |
| 5X First Strand Buffer | 2 |
| 12.5 mM dNTP mix | 0.5 |
| 100 mM DTT | 1 |
| RNase Inhibitor | 1 |
| SuperScript II Reverse Transcriptase | 1 |
| Total Volume per Sample | 5.5 |

6. Gently pipette the entire volume up and down 6-8 times to mix thoroughly, then centrifuge briefly.
7. Add 5.5 µl of the mix to the reaction tube from step 3. Gently pipette the entire volume up and down 6-8 times to mix thoroughly, then centrifuge briefly. The total volume should now be 12.5 µl.
8. Place the tube on the pre-heated thermal cycler. Close the lid and incubate the tube at 50° C. for 1 hour and then place the tube on ice.

Step 2, Part C. Perform PCR Amplification
1. Prepare a separate PCR tube for each index used. Combine the following reagents in a separate, sterile, nuclease-free, 200 µl PCR tube placed on ice. Multiply each reagent volume by the number of samples being prepared. Make 10% extra reagent if you are preparing multiple sample.

TABLE 9

| Reagent | Volume (µl) |
| --- | --- |
| Ultra Pure Water | 8.5 |
| PCR Mix (PML) | 25 |
| RNA PCR Primer (RPI1) | 2 |
| RNA PCR Primer Index (RPIX) | 2 |
| Total Volume per Sample | 37.5 |

2. Gently pipette the entire volume up and down 6-8 times to mix thoroughly, then centrifuge briefly, then place the tube on ice.
3. Add 37.5 µl of PCR master mix to the reaction tube from step 8 of Perform Reverse Transcription.

4. Gently pipette the entire volume up and down 6-8 times to mix thoroughly, then centrifuge briefly and place the tube on ice. The total volume should now be 50 µl.
5. Place the tube on the thermal cycler. Close the lid and amplify the tube on the thermal cycler using the following PCR cycling conditions:
  a. Choose the thermal cycler pre-heat lid option and set to 100° C.
  b. 98° C. for 30 seconds
  c. 11 cycles of: 98° C. for 10 seconds, 60° C. for 30 seconds, and 72° C. for 15 seconds
  d. 72° C. for 10 minutes
  e. 4° C. hold
6. Run each sample on a high sensitivity DNA chip according to the manufacturer's instructions.

Library 2 (L2) Preparation Protocol:
Pre-hybridize [2+2]-TSOs with miRNAs by adding 1 µl of the TSO pool (containing mixture of equimolar amounts of 15 miRNA-specific TSO at 6.7 µM each) to 2 µl of 1 µM Universal miRNA pool (total miRNA input was 2 pmol that is about 2 fmol of each individual miRNA) and heating at 70° C. for 2 min and then slowly cooling (0.1° C./second to 42° C., 42° C. 15', ramp decrease 0.1° C./second to 30° C.) and finally transferring to ice. In a separate tube, add 1 µl of 3'-adapter (RA3) to 2 µl of H$_2$O and incubate at 70° C. for 2 min and immediately transferred to ice. Add entire hybridization mixture (3 µl) to the 3'-adapter solution (3 µl) on ice and continue the rest of the procedure is as described in Step 1, Part A of the L1 Preparation Protocol. Use PCR primer RPI2 is in the library amplification step (see Step 2, Part C of the L1 Preparation Protocol).

Library 3 (L3) Preparation Protocol:
Pre-hybridize [4+0]-TSOs with miRNAs by adding 1 µl of the TSO pool (containing mixture of equimolar amounts of 15 miRNA-specific TSO at 6.7 µM each) to 2 µl of 1 µM Universal miRNA pool (total miRNA input was 2 pmol that is about 2 fmol of each individual miRNA) and heating at 70° C. for 2 min and then slowly cooling (0.1° C./second to 42° C., 42° C. 15', ramp decrease 0.1° C./second to 30° C.) and finally transferring to ice. In a separate tube, add 1 µl of 3'-adapter (RA3) to 2 µl of H$_2$O and incubate at 70° C. for 2 min and immediately transferred to ice. Add entire hybridization mixture (3 µl) to the 3'-adapter solution (3 µl) on ice and continue the rest of the procedure is as described in Step 1, Part A of the L1 Preparation Protocol. Use PCR primer RPI3 in the library amplification step (see Step 2, Part C of the L1 Preparation Protocol).

Library 4 (L4) Preparation Protocol:
Similar protocol as L1, however, Rnl1 is used in both ligation steps (see Step 1, Part A6, the T4 RNA ligase is Rnl1 in the absence ATP; and Step 1, Part B6, the T4 RNA ligase is Rnl1 in the presence of ATP). Use PCR primer RPI4 in the library amplification step (see Step 2, Part C of the L1 Preparation Protocol).

Library 5 (L5) Preparation Protocol:
Pre-hybridize [2+2]-TSOs with miRNAs by adding 1 µl of the TSO pool (containing mixture of equimolar amounts of 15 miRNA-specific TSO at 6.7 µM each) to 2 µl of 1 µM Universal miRNA pool (total miRNA input was 2 pmol that is about 2 fmol of each individual miRNA) and heating at 70° C. for 2 min and then slowly cooling (0.1° C./second to 42° C., 42° C. 15', ramp decrease 0.1° C./second to 30° C.) and finally transferring to ice. In a separate tube, add 1 µl of 3'-adapter (RA3) to 2 µl of H$_2$O and incubate at 70° C. for 2 min and immediately transferred to ice. Add entire hybridization mixture (3 µl) to the 3'-adapter solution (3 µl) on ice and continue the rest of the procedure is as described in Step 1, Part A of the L1 Preparation Protocol, with modifications at the ligation steps (Step 1, Part A6: T4 RNA ligase is Rnl1 in the absence ATP; and Step 1, Part B6, the T4 RNA ligase is Rnl1 in the presence of ATP). Use PCR primer RPI5 in the library amplification step (see Step 2, Part C of the L1 Preparation Protocol).

Library 6 (L6) Preparation Protocol:

Pre-hybridize [4+0]-TSOs with miRNAs by adding 1 µl of the TSO pool (containing mixture of equimolar amounts of 15 miRNA-specific TSO at 6.7 µM each) to 2 µl of 1 µM Universal miRNA pool (total miRNA input was 2 pmol that is about 2 fmol of each individual miRNA) and heating at 70° C. for 2 min and then slowly cooling (0.1° C./second to 42° C., 42° C. 15', ramp decrease 0.1° C./second to 30° C.) and finally transferring to ice. In a separate tube, add 1 µl of 3'-adapter (RA3) to 2 µl of H$_2$O and incubate at 70° C. for 2 min and immediately transferred to ice. Add entire hybridization mixture (3 µl) to the 3'-adapter solution (3 µl) on ice and continue the rest of the procedure is as described in Step 1, Part A of the L1 Preparation Protocol, with modifications at the ligation steps (Step 1, Part A6: T4 RNA ligase is Rnl1 in the absence ATP; and Step 1, Part B6, the T4 RNA ligase is Rnl1 in the presence of ATP). Use PCR primer RPI6 in the library amplification step (see Step 2, Part C of the L1 Preparation Protocol).

Library 7 (L7) Preparation Protocol:

Follow L1 Preparation protocol, with the following modifications:

At Step 1, Part A2: Add [2+2]-TSOs and miRNAs directly into the ligation reaction mixture without pre-hybridization. Continue to Step 1, Part A3 of the L1 Preparation protocol.

At Step 2, Part C: Use PCR primer RPI7 in the library amplification step.

Library 8 (L8) Preparation Protocol:

Follow L1 Preparation protocol, with the following modifications:

At Step 1, Part A2: Add [4+0]-TSOs and miRNAs directly into the ligation reaction mixture without pre-hybridization. Continue to Step 1, Part A3 of the L1 Preparation protocol.

At Step 2, Part C: Use PCR primer RPI8 in the library amplification step.

The PCR products for each library are mixed together and PCR amplicons of the appropriate size (about 147 bp) are gel-purified according to the protocol below.

Purify cDNA Construct Protocol

This process gel purifies the amplified cDNA construct in preparation for subsequent cluster generation. After gel purification, the cDNA is eluted and can be concentrated by ethanol precipitation if desired. Ethanol precipitation will result in a more concentrated final library, at the cost of some yield. Libraries produced without ethanol precipitation may require special handling during denaturation before loading onto a flow cell.

At this point in the protocol, individual libraries with unique indices may be pooled and gel purified together. Combine equal volumes of the library or molar amounts and then load the samples on the gel according to the instructions below. Do not load more than 30 µl of sample per well.

Reagents
Custom Ladder
High Resolution Ladder
Ultra Pure Water
Gel Breaker Tubes
5× Novex TBE Buffer
5 µm Filter Tube
6% Novex TBE PAGE Gel, 1.0 mm, 10 well (1 per 2 sample run)
Amplified cDNA Construct (50 µl)
Razor Blade
DNA Loading Dye
High Sensitivity DNA Chip
Ultra Pure Ethidium Bromide 10 mg/ml
Optional items for ethanol precipitation:
10 mM Tris-HCl, pH 8.5
3 M NaOAc, pH 5.2
70% Ethanol, room temperature
100% Ethanol, −15° to −25° C.
Glycogen
Pellet Paint NF Co-Precipitant
Part A. Dilute Pellet Paint NF Co-Precipitant [Optional, for Ethanol Precipitation Only]

1. Dilute the Pellet Paint NF Co-Precipitant in a separate, sterile, nuclease-free, 200 µl PCR tube. Multiply each reagent volume by the number of samples being prepared, plus 10% extra reagent. Prepare enough pellet paint for a minimum of 10 samples to avoid pipetting small volumes.

TABLE 10

| Reagent | Volume (µl) |
| --- | --- |
| 1X Pellet Paint NF Co-Precipitant | 0.2 |
| Ultra Pure Water | 1.8 |
| Total Volume | 2.0 |

2. Gently pipette the entire volume up and down to mix thoroughly, then centrifuge briefly.

3. Label the tube "0.1× Pellet Paint".

Part B. Run Gel Electrophoresis

1. Determine the volume of 1×TBE Buffer needed. Dilute the 5×TBE Buffer to 1× for use in electrophoresis.

2. Assemble the gel electrophoresis apparatus per the manufacturer's instructions.

3. Mix 2 µl of Custom Ladder with 2 µl of DNA Loading Dye.

4. Mix 1 µl of High Resolution Ladder with 1 µl of DNA Loading Dye.

5. Mix all of the amplified cDNA construct, (typically 48-50 µl) with 10 µl of DNA Loading Dye.

6. Load 2 µl of mixed Custom Ladder and loading dye in two wells on the 6% PAGE Gel.

7. Load 2 µl of High Resolution Ladder and loading dye in a different well.

8. Load two wells with 25 µl each of mixed Amplified cDNA Construct and loading dye on the 6% PAGE Gel. A total volume of 50 µl should be loaded on the gel.

9. Run the gel for 60 minutes at 145 V or until the blue front dye exits the gel. Proceed immediately to the next step.

10. Remove the gel from the apparatus.

Part C. Recover Purified Construct

1. Open the cassette according to the manufacturer's instructions and stain the gel with Ethidium Bromide (0.5 µg/ml in water) in a clean container for 2-3 minutes.

2. Place the gel breaker tube into a sterile, round-bottom, nuclease-free, 2 ml microcentrifuge tube.

3. View the gel on a Dark Reader transilluminator or a UV transilluminator.

4. Using a razor blade, cut out the bands from both lanes that correspond approximately to the adapter-ligated constructs derived from the 22 nt and 30 nt small RNA fragments. Align the razor blade with the top of the 160 bp band of the Custom Ladder, then with the bottom of the 145 bp band of the Custom Ladder. Excise the gel fragment by connecting these cuts on the sides. Both lanes can be combined into one slice.

The band containing the 22 nt RNA fragment with both adapters are a total of 147 nt in length. The band containing the 30 nt RNA fragment with both adapters are 157 nt in length.

5. Place the band of interest into the 0.5 ml Gel Breaker tube from step 2.

6. Centrifuge the stacked tubes to 20,000×g in a microcentrifuge for 2 minutes at room temperature to move the gel through the holes into the 2 ml tube. Ensure that the gel has all moved through the holes into the bottom tube.

7. If precipitating, proceed to Concentrate Final Library by Ethanol Precipitation on page 11. If not precipitating, add 200 µl of Ultra-Pure Water to the gel debris in the 2 ml tube.

8. Elute the DNA by rotating or shaking the tube at room temperature for at least 2 hours. The tube can be rotated or shaken overnight, if desired.

9. Transfer the eluate and the gel debris to the top of a 5 µm filter.

10. Centrifuge the filter for 10 seconds to 600×g.

During cluster generation, this library may need to be denatured using the protocol in the DNA
Template Storage Step 3, Part D. Concentrate Final Library by Ethanol Precipitation

[Optional, for Higher Concentration]

1. Add 300 µl of Ultra Pure Water to the gel debris in the 2 ml tube.

2. Elute the DNA by rotating or shaking the tube at room temperature for at least 2 hours. The tube can be rotated overnight, if desired.

3. Transfer the eluate and the gel debris to the top of a 5 µm filter.

4. Centrifuge the filter for 10 seconds to 600×g.

5. Add 2 µl of Glycogen, 30 µl of 3M NaOAc, 2 µl of 0.1× Pellet Paint (optional) and 975 µl of pre-chilled −15° to −25° C. 100% Ethanol.

6. Immediately centrifuge to 20,000×g for 20 minutes on a benchtop microcentrifuge at 4° C.

7. Remove and discard the supernatant, leaving the pellet intact.

8. Wash the pellet with 500 µl of room temperature 70% Ethanol.

9. Centrifuge to 20,000×g at room temperature for 2 minutes.

10. Remove and discard the supernatant, leaving the pellet intact.

11. Dry the pellet by placing the tube, lid open, in a 37° C. heat block for 5-10 minutes or until dry.

12. Re-suspend the pellet in 10 µl 10 mM Tris-HCl, pH 8.5.

The yield and quality of the amplicons are analyzed using the Nanodrop and Agilent Bioanalyzer 2100. About 1 µg of the DNA amplicons are subjected to Illumina sequencing.

The sequencing data are analyzed using the latest miR-Base (www.mirbase.org/) as the reference library. The copy numbers for each miRNA sequence can be compared to evaluate the accuracy and biases of the tested protocols towards the selected 15 miRNAs. The closer to equimolar the miRNA copy numbers derived from the read frequencies are, the more accurate the method is and has the less bias towards different miRNAs. As described in Example 3, the ligation bias for miRNAs pre-hybridized to the TSOs is expected to be greatly reduced by 90-95%.

Example 7

Expression Profiling of Specific Endogenous miRNAs in Prostate Cancer and Healthy Prostate Samples In this example, we can generate expression profiles of the endogenous miRNAs from Table 1 using samples from prostate cancer and healthy prostate using the library preparation protocols from Example 6. Human plasma specimens from 10 cancer patients and 10 healthy individuals are obtained from a commercial source (e.g., SeraCare). Total RNA is extracted from each specimen and enriched for the small RNA fraction according to the L1 or L4 preparation protocol. Both total RNA and a fraction enriched in small RNAs are assayed using the L2, L3, L5-L8 protocols. The RT-PCR pre-amplification of the sequencing libraries for each clinical sample is performed by 12 rounds of singleplex PCR using PCR primers with bar-codes from the TruSeq Small RNA Sample Prep Kit. Five technical replicates are made for each clinical sample. The resulting PCR amplicons are purified according to the library preparation protocols, and then pooled for simultaneous Illumina sequencing. The miRNA levels (copy numbers) determined by sequencing can be normalized using hsa-miR-130b as an internal reference miRNA (Schaefer et al. 2010). Finally, the absolute and relative expression profiles of the selected 63 miRNAs for both sequencing protocols are analyzed as described in (Hafner et al. 2011).

REFERENCES

Alon, S. et al. 2011. *Genome Res.* 21:1506-11.
Benes, V., Castoldi, M. 2010. *Methods* 50: 244-9.
Bissels, U. et al. 2009. *RNA* 15: 2375-84.
Blow, N. 2009. *Nat. Methods* 6: 231-5.
Chen, J. et al. 2008a. *Nucleic Acids Res.* 36: e87.
Cole, K. B. et al. 2004. *Nucleic Acids Res.* 32: e86.
Cole, K. B. et al. 2009. U.S. Pat. No. 7,504,215B2.
Cole, K. B. et al. 2010. U.S. Pat. No. 7,824,863B2.
Git, A. et al. 2010. *RNA* 16: 991-1006.
Hafner, M. et al. 2008. *Methods* 44: 3-12.
Hafner, M. et al. 2011. *RNA* 17: 1697-712.
Igloi, G. L. 1996. *Anal Biochem.* 233: 124-9.
Knott, T. et al. 2004. United States Patent Application US20040115674A1.
Lamm, A. T. et al. 2011. *Genome Res.* 21: 265-75.
Lee, L. W. et al. 2010. *RNA* 16: 2170-80.
Lesnik, E. A., Freier, S. M. 1995. *Biochemistry* 34: 10807-15.
Lin H. et al. 2006. *J. Am. Chem. Soc.* 128: 3268-72.
Linsen, S. E. et al. 2009. *Nat. Methods.* 6: 474-6.
Mestdagh, P. et al. 2009. *Genome Biol.* 10: R64.
McCormick, K. P. et al. 2011. *Silence* 2: 2.
McDonald, J. S. et al. 2011. *Clin. Chem.* 57: 833-40.
Nelson, P. T. et al. 2008. *Biochim. Biophys. Acta* 1779: 758-65.
Raabe, C. A. et al. 2011. *RNA* 17: 1357-66.
Schaefer, A. et al. 2010. *Exp. Mol. Med.* 42: 749-58.
Stump, M. D. et al. 1999. *Nucleic Acids Res.* 27: 4642-8.
Su, Z. et al. 2011. *Expert Rev. Mol. Diagn.* 11: 333-43.
Sun, G. et al. 2007. *Methods Enzymol.* 427: 123-38.
Thomson, J. M. et al. 2007. *Methods Enzymol.* 427: 107-22.

Tian, G. et al. 2010. *BMC Biotechnol.* 10: 64.
Tuschl, T. et al. 2011. United States Patent Application US20110244523A1.
Vigneault, F. et al. 2008. *Nat. Methods.* 5: 777-9.
Wang, H. et al. 2007. *RNA* 13: 151-9.

Willenbrock, H. et al 2009. *RNA* 15: 2028-34.
Yehudai-Resheff, S., Schuster, G. 2000. *Nucleic Acids Res.* 28: 1139-44.
Zhang, B., Farwell, M. A. 2008. *J. Cell. Mol. Med.* 12: 3-21.

That which is claimed is:

1. A method for detecting and quantifying an amount of a target RNA in a sample, the method comprising:
   a) hybridizing the target RNA with a target-specific oligonucleotide (TSO) to produce a TSO-hybridized target RNA; wherein the TSO is
      (i) shorter than the target RNA, or as long as or shorter than the target RNA wherein the target RNA is a miRNA; and
      (ii) substantially complementary to the target RNA sequence;
   b) ligating a 5' adapter to a 5' end of the TSO-hybridized target RNA and/or ligating a 3' adapter to a 3' end of the TSO-hybridized target RNA, wherein the ligating comprises performing a splint-independent ligation to produce an adapter-ligated TSO-hybridized target RNA, and reverse transcribing the adapter-ligated TSO-hybridized target RNA, or a portion thereof, to produce a reverse transcript thereof;
   c) enzymatically amplifying the reverse transcript, or a portion thereof, to produce an amplified polynucleotide comprising a sequence corresponding to or complementary to the target RNA sequence; and
   d) quantitatively detecting an amount of the amplified polynucleotide, wherein the amount of the amplified polynucleotide correlates with the amount of the target RNA,
   wherein the TSO is not immobilized in any step of the method.

2. The method of claim 1, wherein the hybridizing of the target RNA with the TSO inhibits or promotes ligating oligonucleotide adapter(s) to the ends of the target RNA.

3. The method of claim 1, comprising ligating the 5' adapter to a 5' end of each of a plurality of TSO-hybridized target RNAs to produce a plurality of 5'-end adapter-ligated TSO-hybridized target RNAs.

4. The method of claim 3, wherein the 5' oligonucleotide adaptor comprises a 5'-end group selected from a 5'-phosphate and a 5'-hydroxyl; and wherein the 5' oligonucleotide adaptor is a 5'-hydroxyl, the method further comprises phosphorylating the 5'-hydroxyl after the ligating.

5. The method of claim 1, comprising ligating the 3' adapter to a 3' end of each of a plurality of TSO-hybridized target RNAs to produce a plurality of 3'-end adapter-ligated TSO-hybridized target RNAs.

6. The method of claim 5 wherein the 3' adapter comprises a 5'-end group that is a 5'-phosphate or a 5', 5'-adenyl pyrophosphoryl group.

7. The method of claim 1, comprising ligating the 5' adapter to the 5'-end of the TSO-hybridized target RNA and ligating the 3' adapter to the 3'-end of the TSO-hybridized target RNA to produce a 5'- and 3'-end adapter-ligated TSO-hybridized target RNA, wherein ligating the 5' adapter occurs before ligating the 3' adapter; ligating the 5' adapter occurs after ligating the 3' adapter; or ligating the 5' adapter and ligating the 3' adapter occur simultaneously.

8. The method of claim 1, wherein the 3'- and 5'-adapters are contained within a single oligonucleotide, which is ligated to the 5' or 3' end of the target RNA.

9. The method of claim 1, wherein the ligating comprises adding to the TSO-hybridized target RNA an RNA ligase selected from the group consisting of: T4 RNA ligase 1 (Rnl1), T4 RNA ligase 2 (Rnl2), and a truncated and/or mutated derivative of T4 RNA ligase 2.

10. The method of claim 1, wherein the 3'-adapter and/or the 5'-adapter comprise a sequence used for amplification and/or sequencing.

11. The method of claim 1, further comprising circularizing a non-target RNA in the sample after hybridizing the TSO and the target RNA, but prior to the ligating the TSO-hybridized target RNA, wherein the circularizing prevents ligating of the non-target RNA.

12. The method of claim 1, further comprising circularizing the adapter-ligated TSO-hybridized target RNA prior to the reverse transcribing.

13. The method of claim 1, wherein the quantitatively detecting comprises next generation sequencing.

14. The method of claim 1, comprising purifying the adapter-ligated TSO-hybridized target RNA, the reverse transcript thereof and/or amplified polynucleotide prior to detecting the amplified polynucleotide, wherein the purifying of the products comprises size-dependent separation of at least one of the adapter-ligated TSO-hybridized target RNA, reverse transcript thereof, and the amplified polynucleotide by gel- or capillary electrophoresis.

15. The method of claim 1, wherein the TSO comprises a hapten attached via a non-nucleotide or oligonucleotide linker.

16. The method of claim 1, wherein the target RNA is selected from the group consisting of: a microRNA, a pre-miRNA, a non-coding RNA, fragments of the non-coding RNA, a coding RNA, and fragments of the coding RNA.

17. The method of claim 16, wherein the target RNA is about 15 to 150 nucleotides in length.

18. The method of claim 1, wherein the sample is selected from the group consisting of: a tissue extract, a cell extract, a cell lysate, a tissue lysate, an extracellular bio-fluid extract, and an extracellular bio-fluid lysate.

19. The method of claim 1, wherein the TSO comprises one or more ribonucleotides and/or deoxyribonucleotides, wherein the one or more ribonucleotides and/or deoxyribonucleotides has a modification selected from the group consisting: a 2'-OMe, a 2'-fluoro, a locked nucleic acid (LNA), an abasic site, a non-nucleotide linker, and combinations thereof.

20. The method of claim 1, wherein the TSO comprises a blocking group at (a) its 3'-end, which prevents ligation to or extension of its 3' end, and/or (b) its 5' end, which prevents ligation and/or phosphorylation at its 5' end.

* * * * *

```
                         SEQUENCE LISTING

<160> NUMBER OF SEQ ID NOS: 53

<210> SEQ ID NO 1
<211> LENGTH: 22
<212> TYPE: RNA
<213> ORGANISM: Artificial Sequence
<220> FEATURE:
<223> OTHER INFORMATION: Synthetic Adapter

<400> SEQUENCE: 1
ucguaugccg ucuucugcuu gu                                             22

<210> SEQ ID NO 2
<211> LENGTH: 26
<212> TYPE: RNA
<213> ORGANISM: Artificial Sequence
<220> FEATURE:
<223> OTHER INFORMATION: Synthetic Adapter

<400> SEQUENCE: 2
guucagaguu cuacaguccg acgauc                                         26

<210> SEQ ID NO 3
<211> LENGTH: 21
<212> TYPE: DNA
<213> ORGANISM: Artificial Sequence
<220> FEATURE:
<223> OTHER INFORMATION: Synthetic Primer

<400> SEQUENCE: 3
caagcagaag acggcatacg a                                              21

<210> SEQ ID NO 4
<211> LENGTH: 44
<212> TYPE: DNA
<213> ORGANISM: Artificial Sequence
<220> FEATURE:
<223> OTHER INFORMATION: Synthetic Primer

<400> SEQUENCE: 4
aaggatacgg cgaccaccga caggttcaga gttctacagt ccga                     44

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
caagcagaag acggcatacg a                                              21

<210> SEQ ID NO 6
<211> LENGTH: 32
<212> TYPE: DNA
<213> ORGANISM: Artificial Sequence
<220> FEATURE:
<223> OTHER INFORMATION: Synthetic Primer

<400> SEQUENCE: 6
```

-continued

```
cgacaggttc agagttctac agtccgacga tc                                    32

<210> SEQ ID NO 7
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: miRNA

<400> SEQUENCE: 7
agggcccccc cucaauccug u                                                21

<210> SEQ ID NO 8
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: miRNA

<400> SEQUENCE: 8
cuggcccucu cugcccuucc gu                                               22

<210> SEQ ID NO 9
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: miRNA

<400> SEQUENCE: 9
aggcaagaug cuggcauagc u                                                21

<210> SEQ ID NO 10
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: miRNA

<400> SEQUENCE: 10
guccaguuuu cccaggaauc ccu                                              23

<210> SEQ ID NO 11
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: miRNA

<400> SEQUENCE: 11
cuacaaaggg aagcacuuuc uc                                               22

<210> SEQ ID NO 12
<211> LENGTH: 22
<212> TYPE: RNA
<213> ORGANISM: Homo sapiens
<220> FEATURE:
<221> NAME/KEY: misc_feature
```

```
<222> LOCATION: (1)..(22)
<223> OTHER INFORMATION: miRNA

<400> SEQUENCE: 12
uagcagcacg uaaauauugg cg                                              22

<210> SEQ ID NO 13
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: miRNA

<400> SEQUENCE: 13
uuuggcacua gcacauuuuu gcu                                             23

<210> SEQ ID NO 14
<211> LENGTH: 21
<212> TYPE: RNA
<213> ORGANISM: Homo sapiens
<220> FEATURE:
<221> NAME/KEY: misc_feature
<222> LOCATION: (1)..(21)
<223> OTHER INFORMATION: miRNA

<400> SEQUENCE: 14
cagcagcaca cugugguuug u                                               21

<210> SEQ ID NO 15
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: miRNA

<400> SEQUENCE: 15
uuucaagcca gggggcguuu uuc                                             23

<210> SEQ ID NO 16
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: miRNA

<400> SEQUENCE: 16
ugugcuugcu cgucccgccc gca                                             23

<210> SEQ ID NO 17
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: miRNA

<400> SEQUENCE: 17
ucccugagac ccuaacuugu ga                                              22

<210> SEQ ID NO 18
```

```
<211> LENGTH: 24
<212> TYPE: RNA
<213> ORGANISM: Homo sapiens
<220> FEATURE:
<221> NAME/KEY: misc_feature
<222> LOCATION: (1)..(24)
<223> OTHER INFORMATION: miRNA

<400> SEQUENCE: 18
uuuggcaaug guagaacuca cacu                                              24

<210> SEQ ID NO 19
<211> LENGTH: 23
<212> TYPE: RNA
<213> ORGANISM: Homo sapiens
<220> FEATURE:
<221> NAME/KEY: misc_feature
<222> LOCATION: (1)..(23)
<223> OTHER INFORMATION: miRNA

<400> SEQUENCE: 19
cccaguguuc agacuaccug uuc                                               23

<210> SEQ ID NO 20
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: miRNA

<400> SEQUENCE: 20
aaccagcacc ccaacuuugg ac                                                22

<210> SEQ ID NO 21
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: miRNA

<400> SEQUENCE: 21
cagugguuuu acccuauggu ag                                                22

<210> SEQ ID NO 22
<211> LENGTH: 17
<212> TYPE: DNA
<213> ORGANISM: Artificial Sequence
<220> FEATURE:
<223> OTHER INFORMATION: Synthetic Probe

<400> SEQUENCE: 22
acaggattga ggggggg                                                      17

<210> SEQ ID NO 23
<211> LENGTH: 17
<212> TYPE: DNA
<213> ORGANISM: Artificial Sequence
<220> FEATURE:
<223> OTHER INFORMATION: Synthetic Probe

<400> SEQUENCE: 23
aggattgagg gggggc                                                       17
```

```
<210> SEQ ID NO 24
<211> LENGTH: 18
<212> TYPE: DNA
<213> ORGANISM: Artificial Sequence
<220> FEATURE:
<223> OTHER INFORMATION: Synthetic Probe

<400> SEQUENCE: 24
acggaagggc agagaggg                                                 18

<210> SEQ ID NO 25
<211> LENGTH: 18
<212> TYPE: DNA
<213> ORGANISM: Artificial Sequence
<220> FEATURE:
<223> OTHER INFORMATION: Synthetic Probe

<400> SEQUENCE: 25
ggaagggcag agagggcc                                                 18

<210> SEQ ID NO 26
<211> LENGTH: 17
<212> TYPE: DNA
<213> ORGANISM: Artificial Sequence
<220> FEATURE:
<223> OTHER INFORMATION: Synthetic Probe

<400> SEQUENCE: 26
agctatgcca gcatctt                                                  17

<210> SEQ ID NO 27
<211> LENGTH: 17
<212> TYPE: DNA
<213> ORGANISM: Artificial Sequence
<220> FEATURE:
<223> OTHER INFORMATION: Synthetic Probe

<400> SEQUENCE: 27
ctatgccagc atcttgc                                                  17

<210> SEQ ID NO 28
<211> LENGTH: 19
<212> TYPE: DNA
<213> ORGANISM: Artificial Sequence
<220> FEATURE:
<223> OTHER INFORMATION: Synthetic Probe

<400> SEQUENCE: 28
agggattcct gggaaaact                                                19

<210> SEQ ID NO 29
<211> LENGTH: 19
<212> TYPE: DNA
<213> ORGANISM: Artificial Sequence
<220> FEATURE:
<223> OTHER INFORMATION: Synthetic Probe

<400> SEQUENCE: 29
ggattcctgg gaaaactgg                                                19

<210> SEQ ID NO 30
<211> LENGTH: 18
<212> TYPE: DNA
<213> ORGANISM: Artificial Sequence
<220> FEATURE:
<223> OTHER INFORMATION: Synthetic Probe
```

<400> SEQUENCE: 30
gagaaagtgc ttcccttt                                                 18

<210> SEQ ID NO 31
<211> LENGTH: 18
<212> TYPE: DNA
<213> ORGANISM: Artificial Sequence
<220> FEATURE:
<223> OTHER INFORMATION: Synthetic Probe

<400> SEQUENCE: 31
gaaagtgctt ccctttgt                                                 18

<210> SEQ ID NO 32
<211> LENGTH: 18
<212> TYPE: DNA
<213> ORGANISM: Artificial Sequence
<220> FEATURE:
<223> OTHER INFORMATION: Synthetic Probe

<400> SEQUENCE: 32
tcacaagtta gggtctca                                                 18

<210> SEQ ID NO 33
<211> LENGTH: 18
<212> TYPE: DNA
<213> ORGANISM: Artificial Sequence
<220> FEATURE:
<223> OTHER INFORMATION: Synthetic Probe

<400> SEQUENCE: 33
acaagttagg gtctcagg                                                 18

<210> SEQ ID NO 34
<211> LENGTH: 20
<212> TYPE: DNA
<213> ORGANISM: Artificial Sequence
<220> FEATURE:
<223> OTHER INFORMATION: Synthetic Probe

<400> SEQUENCE: 34
agtgtgagtt ctaccattgc                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic Probe

<400> SEQUENCE: 35
tgtgagttct accattgcca                                               20

<210> SEQ ID NO 36
<211> LENGTH: 19
<212> TYPE: DNA
<213> ORGANISM: Artificial Sequence
<220> FEATURE:
<223> OTHER INFORMATION: Synthetic Probe

<400> SEQUENCE: 36
gaacaggtag tctgaacac                                                19

<210> SEQ ID NO 37
<211> LENGTH: 19

```
<212> TYPE: DNA
<213> ORGANISM: Artificial Sequence
<220> FEATURE:
<223> OTHER INFORMATION: Synthetic Probe

<400> SEQUENCE: 37
acaggtagtc tgaacactg                                                    19

<210> SEQ ID NO 38
<211> LENGTH: 18
<212> TYPE: DNA
<213> ORGANISM: Artificial Sequence
<220> FEATURE:
<223> OTHER INFORMATION: Synthetic Probe

<400> SEQUENCE: 38
gtccaaagtt ggggtgct                                                     18

<210> SEQ ID NO 39
<211> LENGTH: 18
<212> TYPE: DNA
<213> ORGANISM: Artificial Sequence
<220> FEATURE:
<223> OTHER INFORMATION: Synthetic Probe

<400> SEQUENCE: 39
ccaaagttgg ggtgctgg                                                     18

<210> SEQ ID NO 40
<211> LENGTH: 18
<212> TYPE: DNA
<213> ORGANISM: Artificial Sequence
<220> FEATURE:
<223> OTHER INFORMATION: Synthetic Probe

<400> SEQUENCE: 40
ctaccatagg gtaaaacc                                                     18

<210> SEQ ID NO 41
<211> LENGTH: 18
<212> TYPE: DNA
<213> ORGANISM: Artificial Sequence
<220> FEATURE:
<223> OTHER INFORMATION: Synthetic Probe

<400> SEQUENCE: 41
accatagggt aaaaccac                                                     18

<210> SEQ ID NO 42
<211> LENGTH: 18
<212> TYPE: DNA
<213> ORGANISM: Artificial Sequence
<220> FEATURE:
<223> OTHER INFORMATION: Synthetic Probe

<400> SEQUENCE: 42
cgccaatatt tacgtgct                                                     18

<210> SEQ ID NO 43
<211> LENGTH: 18
<212> TYPE: DNA
<213> ORGANISM: Artificial Sequence
<220> FEATURE:
<223> OTHER INFORMATION: Synthetic Probe

<400> SEQUENCE: 43
```

```
ccaatattta cgtgctgc                                                   18
```

<210> SEQ ID NO 44
<211> LENGTH: 19
<212> TYPE: DNA
<213> ORGANISM: Artificial Sequence
<220> FEATURE:
<223> OTHER INFORMATION: Synthetic Probe

<400> SEQUENCE: 44

```
agcaaaaatg tgctagtgc                                                  19
```

<210> SEQ ID NO 45
<211> LENGTH: 19
<212> TYPE: DNA
<213> ORGANISM: Artificial Sequence
<220> FEATURE:
<223> OTHER INFORMATION: Synthetic Probe

<400> SEQUENCE: 45

```
caaaaatgtg ctagtgcca                                                  19
```

<210> SEQ ID NO 46
<211> LENGTH: 17
<212> TYPE: DNA
<213> ORGANISM: Artificial Sequence
<220> FEATURE:
<223> OTHER INFORMATION: Synthetic Probe

<400> SEQUENCE: 46

```
acaaaccaca gtgtgct                                                    17
```

<210> SEQ ID NO 47
<211> LENGTH: 17
<212> TYPE: DNA
<213> ORGANISM: Artificial Sequence
<220> FEATURE:
<223> OTHER INFORMATION: Synthetic Probe

<400> SEQUENCE: 47

```
aaaccacagt gtgctgc                                                    17
```

<210> SEQ ID NO 48
<211> LENGTH: 19
<212> TYPE: DNA
<213> ORGANISM: Artificial Sequence
<220> FEATURE:
<223> OTHER INFORMATION: Synthetic Probe

<400> SEQUENCE: 48

```
gaaaaacgcc ccctggctt                                                  19
```

<210> SEQ ID NO 49
<211> LENGTH: 19
<212> TYPE: DNA
<213> ORGANISM: Artificial Sequence
<220> FEATURE:
<223> OTHER INFORMATION: Synthetic Probe

<400> SEQUENCE: 49

```
aaacgccccc tggcttga                                                   19
```

<210> SEQ ID NO 50
<211> LENGTH: 19
<212> TYPE: DNA
<213> ORGANISM: Artificial Sequence

```
<220> FEATURE:
<223> OTHER INFORMATION: Synthetic Probe

<400> SEQUENCE: 50
tgcgggcggg acgagcaag                                                    19

<210> SEQ ID NO 51
<211> LENGTH: 19
<212> TYPE: DNA
<213> ORGANISM: Artificial Sequence
<220> FEATURE:
<223> OTHER INFORMATION: Synthetic Probe

<400> SEQUENCE: 51
cgggcgggac gagcaagca                                                    19

<210> SEQ ID NO 52
<211> LENGTH: 21
<212> TYPE: DNA
<213> ORGANISM: Artificial Sequence
<220> FEATURE:
<223> OTHER INFORMATION: Synthetic Adapter

<400> SEQUENCE: 52
tggaattctc gggtgccaag g                                                 21

<210> SEQ ID NO 53
<211> LENGTH: 22
<212> TYPE: DNA
<213> ORGANISM: Artificial Sequence
<220> FEATURE:
<223> OTHER INFORMATION: Synthetic Primer

<400> SEQUENCE: 53
gccttggcac ccgagaattc ca                                                22
```